(12) United States Patent
Schaffer

(10) Patent No.: US 8,840,735 B2
(45) Date of Patent: Sep. 23, 2014

(54) FATIGUE DAMAGE RESISTANT WIRE AND METHOD OF PRODUCTION THEREOF

(75) Inventor: Jeremy E. Schaffer, Leo, IN (US)

(73) Assignee: Fort Wayne Metals Research Products Corp, Fort Wayne, IN (US)

( * ) Notice: Subject to any disclaimer, the term of this patent is extended or adjusted under 35 U.S.C. 154(b) by 124 days.

(21) Appl. No.: 12/563,062

(22) Filed: Sep. 18, 2009

(65) Prior Publication Data

US 2010/0075168 A1    Mar. 25, 2010

Related U.S. Application Data

(60) Provisional application No. 61/098,427, filed on Sep. 19, 2008, provisional application No. 61/110,084, filed on Oct. 31, 2008, provisional application No. 61/179,558, filed on May 19, 2009, provisional application No. 61/228,677, filed on Jul. 27, 2009.

(51) Int. Cl.

| | |
|---|---|
| *C22C 38/18* | (2006.01) |
| *C22C 38/40* | (2006.01) |
| *C22C 19/00* | (2006.01) |
| *C22C 19/05* | (2006.01) |
| *C22C 19/07* | (2006.01) |
| *C21D 8/06* | (2006.01) |
| *A61L 31/14* | (2006.01) |
| *A61L 31/02* | (2006.01) |
| *A61N 1/05* | (2006.01) |
| *A61F 2/86* | (2013.01) |

(52) U.S. Cl.
CPC . *C22C 19/00* (2013.01); *A61N 1/05* (2013.01); *A61L 31/022* (2013.01); *A61F 2/86* (2013.01); *A61L 31/14* (2013.01)
USPC ........... 148/325; 148/327; 148/425; 148/426; 148/427; 148/595; 148/597; 148/598; 148/599; 148/677; 428/606; 623/23.71; 623/23.7; 623/1.11; 623/1.15

(58) Field of Classification Search
CPC ...... C22C 19/00; C22C 19/05; C22C 19/051; C22C 19/07; C22C 38/18; C22C 38/40; C21D 8/0468; C21D 8/0436; C21D 8/525; C21D 8/06; C21D 8/065
USPC ................. 148/320, 408–410, 425–429, 442, 148/595–600, 325, 326, 327, 674–677; 428/606
See application file for complete search history.

(56) References Cited

U.S. PATENT DOCUMENTS

| | | |
|---|---|---|
| 3,948,688 A | 4/1976 | Clark |
| 4,881,981 A | 11/1989 | Thoma et al. |

(Continued)

FOREIGN PATENT DOCUMENTS

| | | |
|---|---|---|
| CN | 1410561 A | 4/2003 |
| CN | 1966735 A | 5/2007 |

(Continued)

OTHER PUBLICATIONS

The Written Opinion and Internal Search Report mailed Jan. 4, 2010 in related International Application No. PCT/US2009/057586.

(Continued)

*Primary Examiner* — Deborah Yee
(74) *Attorney, Agent, or Firm* — Faegre Baker Daniels LLP

(57) ABSTRACT

Fatigue damage resistant metal or metal alloy wires have a submicron-scale or nanograin microstructure that demonstrates improved fatigue damage resistance properties, and methods for manufacturing such wires. The present method may be used to form a wire having a nanograin microstructure characterized by a mean grain size that is 500 nm or less, in which the wire demonstrates improved fatigue damage resistance. Wire manufactured in accordance with the present process may show improvement in one or more other material properties, such as ultimate strength, unloading plateau strength, permanent set, ductility, and recoverable strain, for example. Wire manufactured in accordance with the present process is suitable for use in a medical device, or other high end application.

70 Claims, 26 Drawing Sheets

(56) References Cited

U.S. PATENT DOCUMENTS

| | | | |
|---|---|---|---|
| 5,238,004 | A | 8/1993 | Sahatjian et al. |
| 5,836,066 | A | 11/1998 | Ingram |
| 5,843,244 | A | 12/1998 | Pelton et al. |
| 6,399,215 | B1 * | 6/2002 | Zhu et al. ............ 428/544 |
| 6,508,803 | B1 | 1/2003 | Horikawa et al. |
| 6,565,683 | B1 | 5/2003 | Utyashev et al. |
| 7,241,328 | B2 | 7/2007 | Keener |
| 7,455,738 | B2 | 11/2008 | Patel et al. |
| 8,070,888 | B2 * | 12/2011 | Torizuka et al. ............ 148/320 |
| 8,246,762 | B2 * | 8/2012 | Janko et al. ............ 148/320 |
| 2005/0051243 | A1 | 3/2005 | Forbes-Jones et al. |
| 2005/0059994 | A1 | 3/2005 | Walak et al. |
| 2005/0090844 | A1 | 4/2005 | Patel et al. |
| 2006/0021878 | A1 | 2/2006 | Lu et al. |
| 2006/0130942 | A1 | 6/2006 | Ishikawa et al. |
| 2006/0193742 | A1 | 8/2006 | Miura et al. |
| 2006/0248980 | A1 | 11/2006 | Mann et al. |
| 2007/0072147 | A1 | 3/2007 | Berendt |
| 2007/0255387 | A1 * | 11/2007 | Kramer et al. ............ 623/1.11 |
| 2008/0015683 | A1 * | 1/2008 | Kramer-Brown et al. ... 623/1.15 |
| 2008/0041503 | A1 * | 2/2008 | Torizuka et al. ............ 148/599 |
| 2008/0135140 | A1 | 6/2008 | Torizuka et al. |
| 2010/0076556 | A1 * | 3/2010 | Tomantschger et al. ... 623/11.11 |

FOREIGN PATENT DOCUMENTS

| | | |
|---|---|---|
| JP | 10265919 A | 10/1998 |
| JP | 2001-107164 A | 4/2001 |
| JP | 2003-049249 A | 2/2003 |
| JP | 2003201549 A | 7/2003 |
| JP | 2004124227 A | 4/2004 |
| JP | 2008-184643 A | 8/2008 |
| WO | WO2005/045087 A1 | 5/2005 |
| WO | WO2005/087963 A1 | 9/2005 |
| WO | WO2006104823 A2 | 10/2006 |

OTHER PUBLICATIONS

Article "An examination of total fatigue life and life variability in fine medical grade wire," Medical Device Materials IV, Proceedings of the Materials and Processes for Medical Devices Conference, 4th, Palm Beach, California, Sep. 23-25, 2007, Jan. 1, 2008, pp. 73-81, Jeremy E. Schaffer (Schaffer1).

Article "An examination of fatigue initation mechanism in thin 35Co—35Ni—20Cr—10Mo medical grade wires," Jul. 18, 2008, ASTM International, Journal ASTM International, West Conshohocken, Pennsylvania Jeremy E. Schaffer (Schaffer2).

Article "Crack initiation and propagation in 50.9 At. pct Ni—Ti pseudoelastic shape-memory wires in bending-rotation fatigue,", Dec. 1, 2003, Mettalurgical and Materials Transactions A, vol. 34A, Dec. 2003, Takahiro Sawaguchi (Sawaguchi).

Article "The influence of temperature on the evoluation of functional properties during psuedoelastic cycling of ultra fine grained NiTi,", Materials Scienec and Engineering, pp. 142-145, 2008, J. Olbricht et al. (Olbricht).

Article Processing and property assessment of NiTi and NiTiCu shape memory actuator springs, Jan. 1, 2008 Wiley-VCH Verlag GmbH & Co., Ch. Grossmann et al. (Grossmann).

Article "Influence of heat treatment on the fatigue life of a laser-welded NiTI alloy wire," Materials Characterization 58, 2007, 262-266, X.J. Yan et al. (Yan).

Article "A Hierarchical Initiation Mechanism Approach to Modeling Fatigue Life Variability in 35co—35ni—20cr—10mo Alloy Medical Grade Fine Wire," Jeremy E. Schaffer (Purdue University), Aug. 2007 (A_Hierarchical . . . ).

Article "Nucleation of Recrystallization Observed In-Situ in the Bulk of a Deformed Metal," A.W. Larsen, date unknown (Larsen).

Article "Effect of annealing on cold-rolled Ni—Ti alloys," Arvind Srivastava, Materials Science and Engineering A 481-482 (2008) pp. 594-597 (Srivastava).

Article "Phase transformation in superelastic NiTi polycrystalline micro-tubes under tension and torsion—from localization to homogeneous deformation," Qing-Ping Sun et al., International Journal of Solids and Structures 39 (2002) pp. 3797-3809 (Sun).

Article "Alloy composition, deformation temperature, pressure and post-deformation annealing effects in severely deformed Ti—Ni baed shape memory alloys," S.D. Prokoshkin et al., Acta Materialia 53 (2005) pp. 2703-2714 (Proskoshkin).

Article "Martensitic transformation of NiTi nanocrystals embedded in an amorphous matrix," T. Waitz et al., Acta Materialia 52 (2004) pp. 5461-5469 (Waitz1).

Article "Martensitic phase transformations in nanocrystalline NiTi studied by TEM," T. Waitz et al., Acta Materialia 52 (2004) pp. 137-147 (Waitz2).

The International Preliminary Report on Patentability mailed Mar. 15, 2011 in related International Application No. PCT/US2009/057586.

Abstract from the International Conference on Shape Memory and Superelastic Technologies, May 7-11, 2006, C.J. Berendt et al.

European Office Action mailed Mar. 20, 2013 from the EPO in related European Application No. 09741508.7.

Japanese Office Action mailed Apr. 9, 2013 in related Japanese Patent Application No. 2011-527075.

Article—An overview: Fatigue behaviour of ultrafine-grained metals and alloys, Hoppel et al., International Journal of Fatigue 28 (2006) pp. 1001-1010.

* cited by examiner

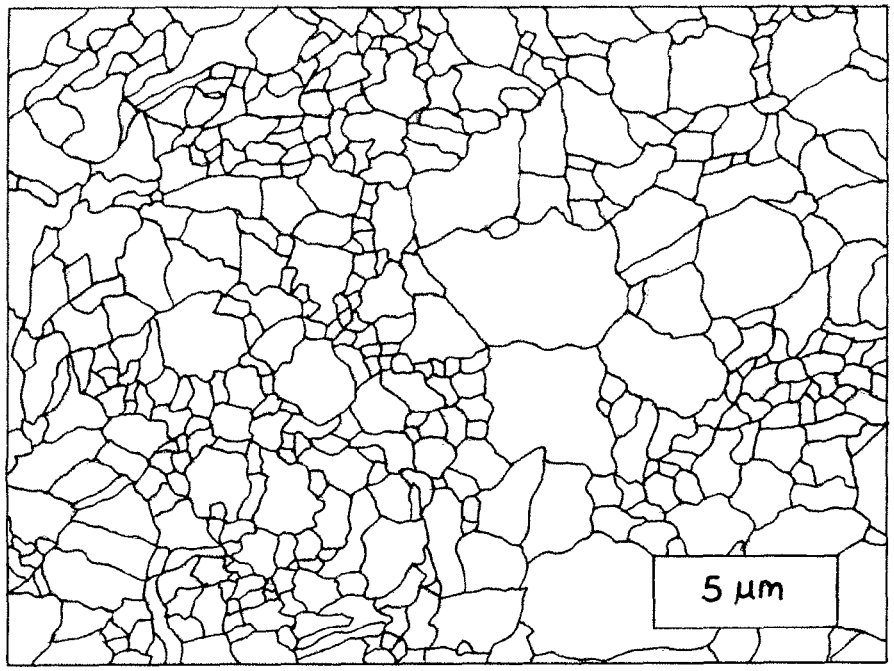
FIG_1
PRIOR ART
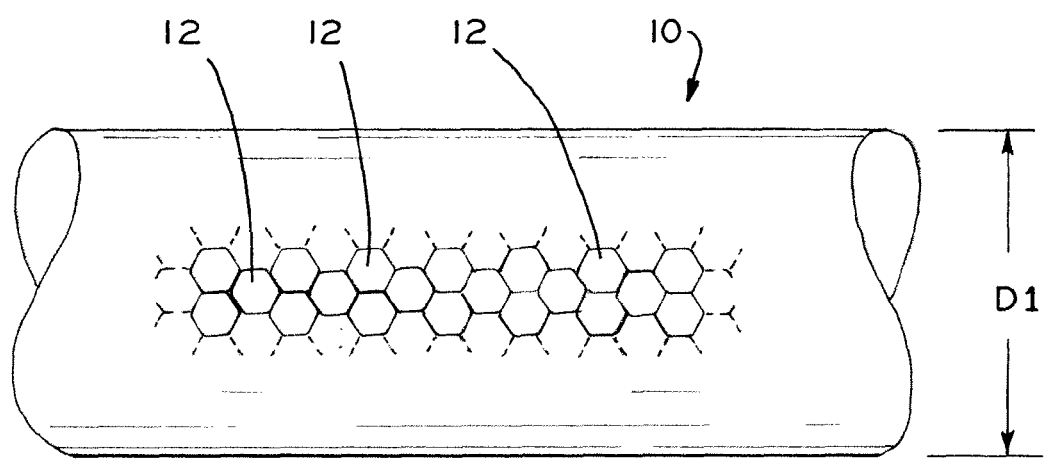
FIG_2

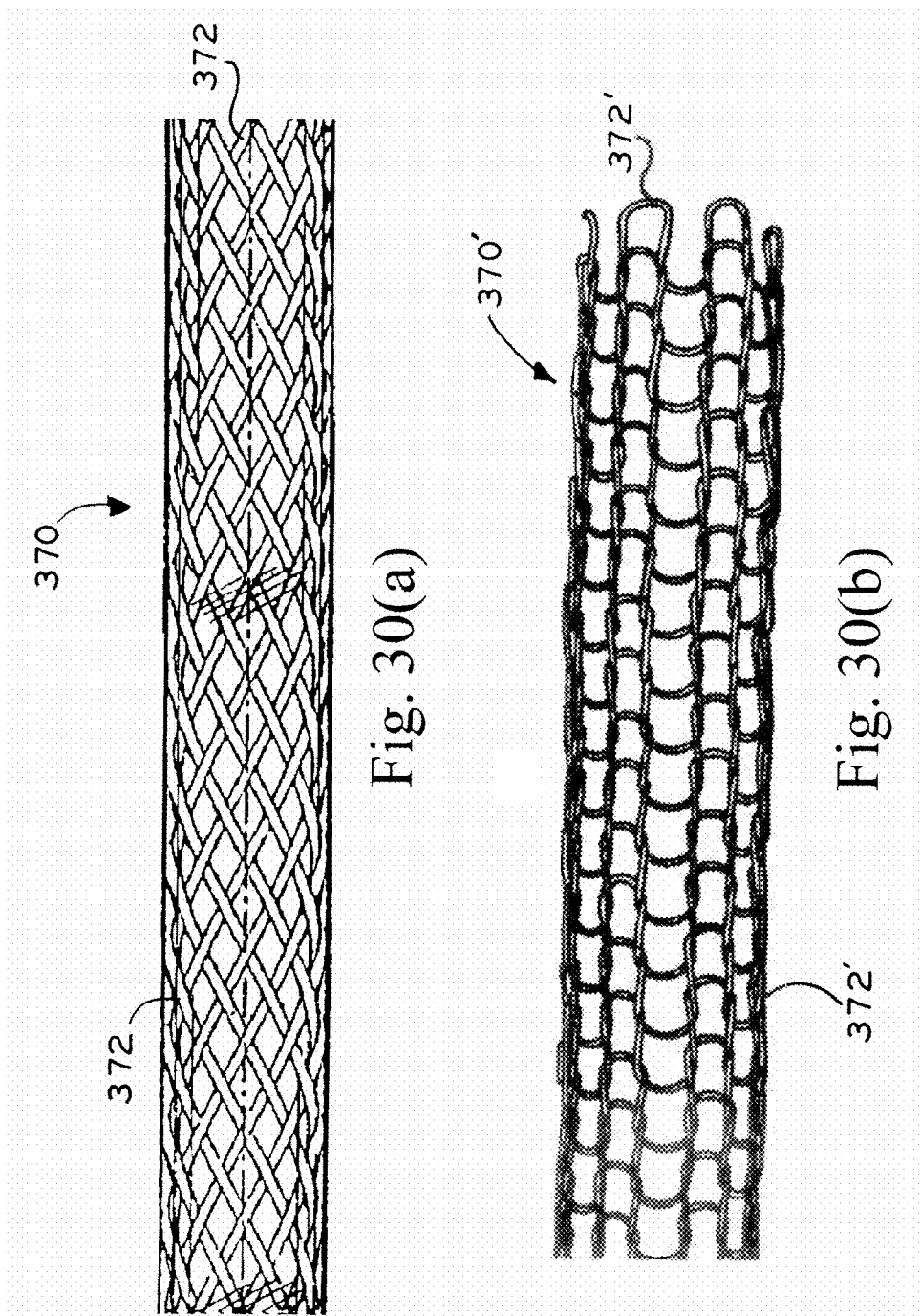

FATIGUE DAMAGE RESISTANT WIRE AND METHOD OF PRODUCTION THEREOF

CROSS REFERENCE TO RELATED APPLICATIONS

This application claims the benefit under Title 35, U.S.C. §119 (e) of U.S. Provisional Patent Application Ser. No. 61/098,427, entitled NANOGRAIN DAMAGE RESISTANT WIRE, filed on Sep. 19, 2008; U.S. Provisional Patent Application Ser. No. 61/110,084, entitled NANOGRAIN DAMAGE RESISTANT WIRE, filed on Oct. 31, 2008; U.S. Provisional Patent Application Ser. No. 61/179,558, entitled NANOGRAIN DAMAGE RESISTANT WIRE, filed on May 19, 2009; and U.S. Provisional Patent Application Ser. No. 61/228,677, entitled NANOGRAIN DAMAGE RESISTANT WIRE, filed on Jul. 27, 2009, the entire disclosures of which are expressly incorporated herein by reference.

BACKGROUND

1. Field of the Invention

The present process relates to fatigue damage resistant wire and, in particular, relates to a method of manufacturing a metal or metal alloy wire that demonstrates improved fatigue damage resistance properties, and metal or metal alloy wires made in accordance with such method.

2. Description of the Related Art

It is well known that most of the transition metals tend to be anisotropic, whereby the rheological, tribological, mechanical, and electrical properties vary with crystal direction. It follows that such properties of a metallic material are all dependent on the presence of crystallographic texture (or lack of texture) in the atomic lattice, or crystal arrangement, of the metallic material.

Grain size has been known as an important variable in defining material strength, fracture toughness and fatigue strength for the majority of the twentieth century. For example, gas turbine engines use rotors comprising single metal crystals or large directionally grown crystals to engineer strength in desirable application-specific orientations, such as to create a turbine blade with high strength along the radial direction to prevent or minimize damage during high speed spinning in which high stress is found along the radial direction.

Conventional wire materials have a microstructural cell size (often referred to as crystal size or grain size) that, after processing, is on the order of microns (μm) through millimeters. A micrograph is shown in FIG. 1 of a representative conventional implant grade wire made of 35N LT® alloy (35N LT® is a registered trademark of Fort Wayne Metals Research Products Corporation of Fort Wayne, Ind.), having a grain size on the order of 3 to 12 μm.

Typical medical grade wires are made of biocompatible implant grade materials, including alloys complying with the chemical compositional requirements of ASTM F562. Such wire materials include Co/Cr/Ni/Mo materials including 35 wt % Co-35 wt % Ni-20 wt % Cr-10 wt % Mo, and MP35N® alloy (MP35N® is a registered trademark of SPS Technologies, Inc. of Jenkintown, Pa.). Other biocompatible implant grade materials include nickel-titanium (NiTi), binary shape memory material including Nitinol, as well as Nitinol tertiary alloys (nickel-titanium with additions such as chromium, tantalum, palladium, platinum, iron, cobalt, tungsten, iridium and gold), as well as platinum and alloys of platinum, titanium and alloys of titanium, 300 series stainless steel, and other materials.

Significant research has been dedicated to understanding how alloys such as NiTi behave in the body from the viewpoint of a biological host response, but much less has been published that quantitatively correlates structure with mechanical properties.

These materials may be manufactured by forming a relatively thick piece of hot-worked rod stock from a melt process, and are further processed into wires by drawing the rod stock down to a thin diameter wire.

During each drawing process, often referred to as a "cold working" process, the wire is pulled through a lubricated die to reduce its diameter. The deformation associated with wire drawing increases the internal stress, or stored energy, in the material and tends to decrease ductility. The internal stress eventually must be relieved by various methods of heat treatment or annealing at elevated temperatures to restore ductility, thus enabling the material to be further cold worked to a smaller diameter. Conventional wire annealing typically results in several stages of stress relief, such as: dislocation annihilation, grain nucleation, and grain growth and a generally random crystal orientation distribution. The various material or fiber "textures" that are generated during cold wire drawing are mostly eliminated during conventional annealing and recrystallization. These iterative processes of cold working and annealing may be repeated several times before a wire of a desired diameter is produced and processing is completed.

Although wires made in accordance with foregoing process typically demonstrate excellent fatigue damage resistance properties, further improvements in fatigue damage resistance properties are desired.

Various methods of forming submicron or nano-grained metallic materials are known. In some methods, nanoscale metal powders are formed by hot isostatic pressing (HIPing) to consolidate the powders into a desired shape.

Several additional methods are versions of severe plastic deformation (SPD), in which a metallic material is subjected to plastic strains of more than 600% to 800%. Each of these methods is characterized by the cross-section of the work piece remaining constant before and after the SPD. In high pressure torsion (HPT), a continuous shear is applied to a work piece, such as by placing the work piece between two anvils that are rotated with respect to each other to generate the shear via frictional traction forces. In equal channel angular pressing (ECAP), a special tool having intersecting channels is used to subject a work piece to simple shear while maintaining the cross section of the work piece, and the work piece may be subjected to several ECAP steps to reach a desired degree of plastic deformation. In cyclic channel die compression (CCDC), a work piece is deformed in a special die that corresponds in shape to the work piece, wherein the work piece is first oriented 90° in the die with respect to the nominal shape of the die that corresponds to the shape of the work piece. The work piece is deformed in the die to change to the shape of the die, followed by rotating the work piece 90° and repeating to reach a desired degree of severe plastic deformation.

Although these methods may be suitable in certain applications for materials of certain shapes, these methods are not suitable for the production of metal or high surface quality continuous metal alloy wires of fine diameters such as less than 1.0 mm, for example.

What is needed is a method of manufacturing a metal or metal alloy wire that demonstrates improved fatigue damage resistance properties, and metal or metal alloy wires made in accordance with such method.

SUMMARY

The present disclosure relates to fatigue damage resistant metal or metal alloy wires having a submicron-scale or nanograin microstructure that demonstrates improved fatigue damage resistance properties, and methods for manufacturing such wires. The present method may be used to form a wire having a nanograin microstructure characterized by a mean grain size that is 500 nm or less, in which the wire demonstrates improved fatigue damage resistance. Wire manufactured in accordance with the present process may show improvement in one or more other material properties, such as ultimate strength, unloading plateau strength, permanent set, ductility, and recoverable strain, for example. Wire manufactured in accordance with the present process is suitable for use in medical devices, or other high end applications.

In one form thereof, the present process provides a metallic wire comprising an implant grade, metal or non-shape memory metal alloy having one of a diameter and a thickness less than 1.0 mm, and a mean grain size of less than 500 nanometers. The wire may have a fatigue endurance exceeding 0.35% strain amplitude at one million cycles.

In one embodiment, the wire may comprise a Co/Ni/Cr/Mo metal alloy having a fatigue endurance selected from the group consisting of: exceeding 0.45% strain amplitude at greater than $10^6$ cycles; exceeding 0.45% strain amplitude at greater than $10^7$ cycles; and exceeding 0.45% strain amplitude at greater than $10^8$ cycles. In another embodiment, the wire may comprise a 304L stainless steel having a fatigue endurance selected from the group consisting of: exceeding 0.4% strain amplitude at greater than $10^6$ cycles; exceeding 0.4% strain amplitude at greater than $10^7$ cycles; and exceeding 0.4% strain amplitude at greater than $10^8$ cycles. In a further embodiment, the wire may comprise a 316L stainless steel having a fatigue endurance selected from the group consisting of: exceeding 0.35% strain amplitude at greater than $10^6$ cycles; exceeding 0.35% strain amplitude at greater than $10^7$ cycles; and exceeding 0.35% strain amplitude at greater than $10^8$ cycles. In a still further embodiment, the wire may comprise a Co/Cr/Fe/Ni/Mo metal alloy having a fatigue endurance selected from the group consisting of: exceeding 0.4% strain amplitude at greater than $10^6$ cycles; exceeding 0.4% strain amplitude at greater than $10^7$ cycles; and exceeding 0.4% strain amplitude at greater than $10^8$ cycles.

In another embodiment, the wire has one of a diameter and a thickness, and an axial ductility of greater than 6% strain to rupture, as measured by a monotonic tensile test with a gauge length exceeding 250× the diameter or thickness of the wire at a temperature of 298±5K. In a further embodiment, the wire may comprise a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of at least 0.85.

In a further embodiment, the wire has one of a diameter and a thickness, and an axial ductility of greater than 10% strain to rupture, as measured by a monotonic tensile test with a gauge length exceeding 250× the diameter or thickness of the wire at a temperature of 298±5K. In a further embodiment, the wire may comprise a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of at least 0.85.

In another form thereof, the present process provides a method of forming a wire made of an implant grade, metal or non-shape memory metal alloy, comprising the steps of: providing a wire having a relatively larger diameter $D_1$; subjecting the wire to cold work conditioning to impart one of: i) 50% and 99.9% cold work and ii) 0.69 and 6.91 units of true strain by drawing the wire to a relatively smaller diameter $D_2$, wherein % cold work is determined by the following formula:

$$cw = 1 - \left(\frac{D_2}{D_1}\right)^2$$

and true strain is determined by the following formula:

$$ts = \ln\left(\left(\frac{D_1}{D_2}\right)^2\right); \text{ and}$$

annealing the wire to create a crystal structure having a mean grain size of less than 500 nanometers.

The wire may comprise a metal alloy selected from the group consisting of: i) a Co/Ni/Cr/Mo metal alloy; ii) a 304L stainless steel; iii) a 316L stainless steel; and iv) a Co/Cr/Fe/Ni/Mo metal alloy.

In one embodiment, the annealing step may further comprise annealing the wire at a temperature of between 600° C. and 950° C. for a dwell time of between 0.1 and 3600 seconds. In another embodiment, the annealing step further comprises annealing the wire at a temperature of between 750° C. and 900° C. for a dwell time of between 0.2 and 120 seconds. Further, the method may further comprise the additional step, following the annealing step, of subjecting the wire to additional cold work.

In a further form thereof, the present process provides a wire made of nickel-titanium shape memory material, having an average grain size of less than 300 nm, and being substantially free of $Ti_xNi_y$ precipitates that exceed 5 nanometers in size. The wire may have a diameter less than 1.0 mm. Also, the wire may exhibit a total isothermally recoverable strain of greater than 9%, as measured by a uniaxial tensile test at a temperature of 298±5K, and may exhibiting a loading plateau length greater than 9.5% axial engineering strain, as measured by a uniaxial tensile test at a temperature of 298±5K.

In another embodiment, the wire may have one or more of: an ultimate tensile strength exceeding 1100 MPa; an average grain size of less than 100 nanometers; an active austenitic finish temperature ($A_f$) below 325K; and an axial engineering strain to rupture exceeding 10% engineering strain.

In a still further form thereof, the present process provides a method of forming a wire made of nickel-titanium shape memory material, comprising the steps of: providing a wire having a relatively larger diameter $D_1$; subjecting the wire to cold work conditioning to impart between 15% and 45% cold work by drawing the wire to a relatively smaller diameter $D_2$, wherein the percent cold work is determined by the following formula:

$$cw = 1 - \left(\frac{D_2}{D_1}\right)^2; \text{ and}$$

annealing the wire at a temperature of between 300° C. and 600° C. for a dwell time of between 0.2 and 900 seconds, wherein the annealing creates a crystal structure having an average grain size of less than 500 nanometers.

BRIEF DESCRIPTION OF THE DRAWINGS

The above-mentioned and other features and advantages of this invention, and the manner of attaining them, will become more apparent and the invention itself will be better understood by reference to the following descriptions of embodiments of the invention taken in conjunction with the accompanying drawings, wherein:

FIG. 1 is a micrograph, taken using scanning electron microscopy (SEM) in a backscattered electron imaging (BEI) mode, of a prior art implant grade wire made of MP35N® alloy, the wire having an mean grain size on the order of 3 μm;

FIG. 2 is a schematic view of a portion of wire having an equiaxed grain structure;

FIG. 8 corresponds to Example 1, wherein:

FIG. 8 is a graphical depiction of cyclic strain amplitude versus fatigue cycle life which compares two 35N LT® alloy wires manufactured in accordance with the present process, namely nanocrystalline 75 μm wire (depicted as X-shaped marks) and nanocrystalline 177 μm wire (depicted as filled square-shaped marks), with conventional microcrystalline MP35N® and 35N LT® alloy wires, which are represented by diamonds, triangles and unfilled squares;

FIGS. 9(a)-16(b) correspond to Example 2, wherein:

FIG. 9(a) is a schematic of dual beam SEM/FIB equipment used for thin foil TEM sample preparation in which a gallium ion source for milling is targeted at a common eucentric height shared by the electron beam for imaging, wherein gallium ions are accelerated using a 30 kV potential and electromagnetically focused to an area which can be controlled by feedback image data gathered from the far less damaging scanning electron beam;

FIG. 9(b) depicts cross section "rough" cuts that expose lift out foil at a nominal thickness of 1000 nm;

FIG. 9(c) depicts a foil lift out using a 2 μm tungsten probe;

FIG. 9(d) depicts the foil after attachment to a SEM grid post upon which the sample is thinned at reduced ion current to a thickness of about 100 nm or less;

FIG. 12 depicts, at left, a Nitinol oxide layer and, at right, a SADP taken from the area surrounded by the circle to the left showing powder diffraction of very fine oxide nanostructure;

FIG. 13 depicts a cumulative distribution function representation of grain size distributions for various mean grain sizes, which, from left to right, are 50 nm, 100 nm, 2000 nm, 5000 nm, and 10000 nm, respectively;

FIG. 14 depicts digital vision bend and free recovery (BFR) test data for five distinct grain sizes, wherein it is postulated that active austenitic finish temperature shift is due to a combination of: transformation shift associated with high grain boundary content in nanocrystalline material and slight matrix Ni loss due to Ni-rich precipitation;

FIG. 16(a) is a graphical strain-life representation of rotary beam fatigue data under the following test conditions: R=−1, T=298 K, f=60 s$^{-1}$; environment: quiescent air, N=5 at each strain level;

FIG. 16(b) is a graphical representation of strain limit at $10^7$ cycles, with a maximum strain level error of ±3% and a cycle count error of <0.1%;

FIGS. 17(a)-17(c) correspond to Example 3, wherein:

FIG. 17(a) is a graphical depiction of true strain versus true stress for a 35N LT® alloy wire made in accordance with the present process having a diameter of 0.007-in (0.18 mm);

FIG. 17(b) is a graphical depiction of true strain versus true stress for a 35N LT® alloy wire made in accordance with the present process having a diameter of 0.0042-in (0.107 mm);

FIG. 17(c) is a graphical depiction of true strain versus true stress for a 35N LT® alloy ribbon made in accordance with the present process having cross sectional thickness of 0.005-in (0.127 mm) in the minor dimension with a 0.009-in (0.229 mm) major dimension orthogonal to the minor dimension;

FIGS. 18(a)-18(b) correspond to Example 4, wherein:

FIG. 18(a) is a graphical depiction of true strain versus true stress for a 35N LT® alloy wire made with additional cold work, in accordance with the present process, the wire having a diameter of 0.0035-in (0.089 mm);

FIG. 18(b) is a graphical depiction of true strain versus true stress for a 35N LT® alloy wire made with additional cold work, in accordance with the present process, the wire having a diameter of 0.003-in (0.076 mm);

FIGS. 19(a)-19(c) correspond to Example 5, wherein:

FIG. 19(a) is a graphical depiction of true strain versus true stress for a 304L wire with a standard microstructure having a diameter of 0.007-in (0.18 mm);

FIG. 19(b) is a graphical depiction of true strain versus true stress for a 304L wire made in accordance with the present process having a diameter of 0.007-in (0.18 mm);

FIG. 19(c) is a graphical strain-life representation of rotary beam fatigue data for 304L wire under the following test conditions: R=−1, T=298 K, f=60 s$^{-1}$; environment: quiescent air;

FIGS. 20(a)-20(c) correspond to Example 7, wherein:

FIG. 20(a) is a graphical depiction of true strain versus true stress for a 316L wire with a standard microstructure having a diameter of 0.007-in (0.18 mm);

FIG. 20(b) is a graphical depiction of true strain versus true stress for a 316L wire made in accordance with the present process having a diameter of 0.007-in (0.18 mm);

FIG. 20(c) is a graphical strain-life representation of rotary beam fatigue data for 316L wire under the following test conditions: R=−1, T=298 K, f=60 s$^{-1}$; environment: quiescent air;

FIGS. 21(a)-21(b) correspond to Example 7, wherein:

FIG. 21(a) is a graphical depiction of true strain versus true stress for an alloy wire complying with the chemical compositional requirements of ASTM F1058, and made in accordance with the present process having a diameter of 0.0089-in (0.23 mm);

FIG. 21(b) is a graphical strain-life representation of rotary beam fatigue data for an alloy wire complying with the chemical compositional requirements of ASTM F1058 under the following test conditions: R=−1, T=298 K, f=60 s$^{-1}$; and environment: quiescent air;

FIG. 30(a) is an elevation view of a braided tissue scaffold or stent including a wire made in accordance with the present process; and FIG. 30(b) is an elevation view of a knitted tissue scaffold or stent including a wire made in accordance with the present process.

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 3:
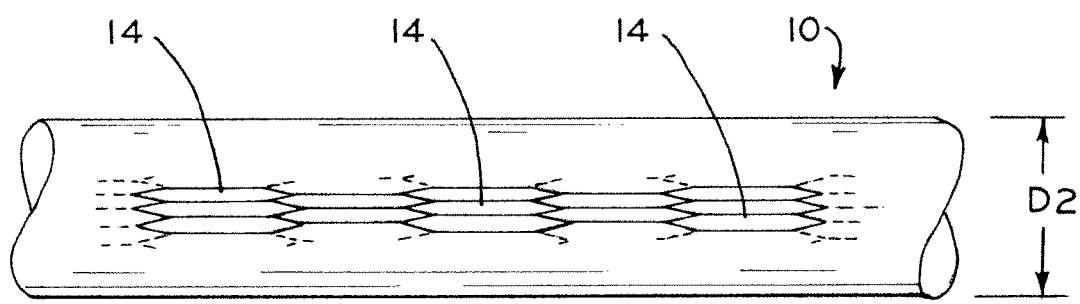
FIG. 3 is a schematic view of the portion of wire of FIG. 2 having an elongated grain structure after cold work conditioning in accordance with an embodiment of the present process.

The present disclosure relates to fatigue damage resistant metal or metal alloy wires having a submicron-scale or nanograin microstructure that demonstrates improved fatigue damage resistance properties, and methods for manufacturing such wires.

Exemplary manufacturing processes by which wires may be made in accordance with the present process are set forth in Section I below, and general descriptions of the resulting physical characteristics of wires made in accordance with the present process are set forth in Section II below. Working Examples are set forth in Section III below. Exemplary applications using wires made in accordance with the present process are set forth in Section IV below.

Various pure state metal materials and metal alloy materials may be subjected to the present manufacturing process to achieve improved physical characteristics substantially similar to the improved physical characteristics demonstrated by materials identified in the discussion below and in the corresponding Examples.

Suitable pure state metals that may be used for forming wires according to the present process include biocompatible, implant-grade metals, such as titanium, tantalum, platinum and palladium, as well as other metals that are not considered biocompatible or implant-grade, such as copper, aluminum, nickel, rhenium, iron, lanthanum and molybdenum.

Suitable biocompatible, implant-grade metal alloy materials that may be used for forming wires according to the present process include non-shape memory metal alloys of the above-listed metals, as well as specialty alloys including Co/Cr/Ni/Mo alloys, and such alloys conforming to the chemical compositional requirements of ASTM F562 (nominally 35 wt % Co-35 wt % Ni-20 wt % Cr-10 wt % Mo). Suitable ASTM F562 alloys include MP35N® and 35N LT® alloy. 35N LT® alloy is available from Fort Wayne Metals Research Products Corporation of Fort Wayne, Ind. A 35N LT® alloy suitable for use in the present process, in which titanium-based inclusions are reduced or eliminated, is described in U.S. patent application Ser. No. 10/656,918, published as U.S. Patent Application Publication No. 2005/0051243, filed Sep. 5, 2003, entitled COBALT-NICKEL-CHROMIUM-MOLYBDENUM ALLOYS WITH REDUCED LEVEL OF TITANIUM NITRIDE INCLUSIONS, assigned in part to the assignee of the present process, the disclosure of which is hereby expressly incorporated by reference herein in its entirety Implant grade specialty alloys including Co/Cr/Ni/Mo/Fe and such alloys conforming to the compositional requirements ASTM F1058 (nominally 40 wt % Co-20 wt % Cr-16 wt % Fe-15 wt % Ni-7 wt % Mo) are other suitable biocompatible metal alloys that may be used for forming wires according to the present process, such as Conichrome, Elgiloy® (Elgiloy® is a registered trademark of Combined Metals of Chicago, LLC of Elk Grove Village, Ill.) and Phynox. One suitable ASTM F1058 alloy is FWM 1058 alloy available from Fort Wayne Metals Research Products Corporation of Fort Wayne, Indiana. Other biocompatible materials suitable for forming wires in accordance with the present process include stainless steel such as 304L and 316L stainless steel and other 300- and 400-series stainless steels, L605 alloy, titanium-6 wt % Aluminum-4 wt % Vanadium, other stabilized-beta-phase titanium alloys such as Beta C (which comprises primarily the beta phase at room temperature), and others.

Additionally, various shape-memory alloys having either a one-way memory effect or a two-way memory effect may be subjected to the present manufacturing process to achieve physical characteristics substantially similar to the physical characteristics of Nitinol identified in the discussion below and in the corresponding Working Examples. Such shape-memory alloys include Nitinol (a nickel-titanium, binary shape memory material); Nitinol tertiary or quaternary alloys (Nitinol with additive metals such as chromium, tantalum, palladium, platinum, iron, cobalt, tungsten, iridium, gold), and others.

As described in detail in Section IV, fatigue damage resistant metal or metal alloy wires made in accordance with the present process may be used in medical devices such as, for example, implantable cardiac pacing, shocking and/or sensing leads, implantable neurological stimulating and/or sensing leads, guidewires, and implantable wire-based gastric, vascular or esophageal stents or other high performance application such as fatigue resistant wires and cables for automotive or aerospace actuators.

I. Description of the Present Manufacturing Process

A. Non-shape Memory Biocompatible Metal Alloys

Exemplary non-shape memory biocompatible metal alloys discussed below include alloys conforming to the chemical compositional requirements of ASTM F562 (MP35N® and 35N LT® alloys), stainless steels (304L and 316L stainless steels) and alloys conforming to the chemical compositional requirements of ASTM F1058 (such as FWM 1058, Conichrome, Elgiloy® and Phynox).

One exemplary method of manufacturing a wire having the properties and advantages set forth herein involves first forming a piece of rod stock, for example, based on conventional melt processing techniques, followed by one or more iterations of conventional cold working and annealing. Referring to FIG. 2, a schematic or exaggerated view of a portion of wire 10 manufactured in accordance with conventional cold working and annealing techniques is shown. Wire 10 has been subjected to one or more, perhaps several or a very large number of, iterations of conventional cold working and annealing, as described above, to form a ductile and generally equiaxed crystal structure within the material of wire 10. Representative equiaxed crystals 12 are depicted in wire 10. As used herein, "equiaxed" refers to a crystal structure in which the individual crystals 12 have approximately the same dimension along both transverse and longitudinal material axes, or any arbitrarily defined axis. After conventional processing which results in a suitably ductile material, wire 10 is ready for processing according to the present process. However, it is within the scope of the invention that the crystals 12 of wire 10 need not be completely equiaxed, i.e., may be substantially equiaxed, in order for wire 10 to be ready for processing described below.

1. Cold Work Conditioning

Thereafter, wire 10 is subjected to a cold work conditioning step. As used herein, "cold work conditioning" means imparting a relatively large amount of cold work to a material with concomitant reduction in the cross-sectional area of the material, for example, by drawing a wire to impart a high degree of cold deformation which is more than would be typical in a conventional iteration of cold working of the wire based on the metal or metal alloy of which the wire is made. The total cold work imparted to the material during the cold work conditioning step is on the order of at least 50% and as much as 99.999% according to the following formula (I):

$$cw = 1 - \left(\frac{D_2}{D_1}\right)^2 \qquad (I)$$

wherein "cw" is cold work defined by reduction of the original material area, "$D_2$" is the diameter of the wire after the cold work conditioning draw or draws, and "$D_1$" is the diameter of the wire prior to the same cold work conditioning draw or draws.

At high levels of cold work, true strain imparted during deformation can provide a better representation of total deformation. In this alternative expression of total imparted cold work, the cold work conditioning step imparts total true strain on the order of greater than 0.6 units and less than 12 units true strain according to the following formula (II):

$$ts = \ln\left(\left(\frac{D_1}{D_2}\right)^2\right) \qquad (II)$$

wherein "ts" is cold work defined by true strain, "ln" is the natural logarithm operator, and $D_1$ and $D_2$ are the diameter prior to cold work conditioning and after cold work conditioning respectively.

Figure 4:
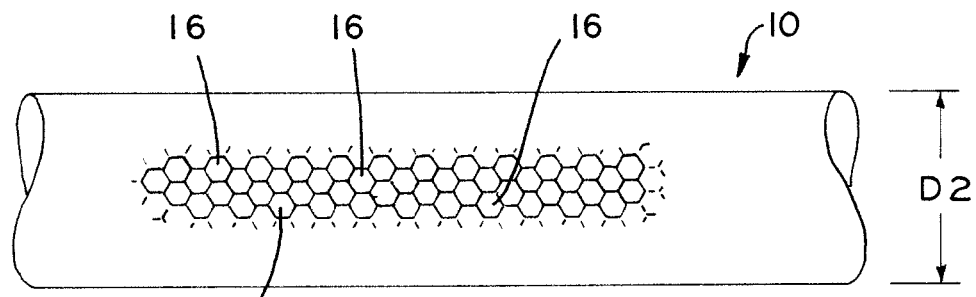
FIG. 4 is a schematic view of the portion of wire of FIG. 3 having an equiaxed grain structure with smaller grains than the equiaxed grain structure of the wire in FIG. 2 after nanorecrystallization in accordance with an embodiment of the present process.

Referring to FIGS. 2-4, the cold work conditioning step is performed by drawing wire 10 through a lubricated die 18 (FIG. 5) having a an output diameter $D_2$, which is substantially less than diameter $D_1$ of the undrawn wire 10 shown in FIG. 2. Alternatively, wire 10 may be cold-swaged, rolled flat or into other shapes which result in the net accumulation of cold work. Cold work conditioning may also employ any combination of techniques including the techniques described here, for example, cold-swaging followed by drawing through a lubricated die finished by cold rolling into a ribbon or sheet form or other shaped wire forms. In one exemplary embodiment, the cold work conditioning step by which the diameter of wire 10 is reduced from $D_1$ to $D_2$ is performed in a single draw and, in another embodiment, the cold work conditioning step by which the diameter of wire 10 is reduced from $D_1$ to $D_2$ is performed in multiple draws which are performed sequentially without any annealing step therebetween.

For non-shape memory biocompatible metal alloy materials, such as those discussed below, the cold work conditioning step imparts between 50% and 99.999% cold work (0.69 to 11.51 units true strain).

For example, for materials conforming to the chemical compositional requirements of ASTM F562, an exemplary cold work conditioning step may impart a cold work (or true strain) of as little as 50% (0.69 units), 65% (1.05 units) or 92% (2.53 units) and as much as 99.0% (4.61 units), 99.9% (6.91 units) or 99.99% (9.21 units), or within any range defined between any pair of the foregoing values. These materials include, but are not limited to: MP35N® wire having a diameter of less than 500 µm; 35N LT® wire having a diameter of less than 500 µm; and 35N LT® ribbon having a cross sectional thickness in the minor dimension of less than 500 µm. As used in connection with ribbon, the term "thickness" as used herein refers to the cross sectional thickness in the minor dimension. with the major dimension orthogonal to the minor dimension.

For one form of 304 stainless steel, such as 304L stainless steel wire having a diameter of less than 500 µm, an exemplary cold work conditioning steps may impart a cold work (or true strain) of as little as 50% (0.69 units), 70% (1.20 units) or 94% (2.81 units) and as much as 99.99% (9.21 units), or within any range defined between any pair of the foregoing values.

For another form of 304 stainless steel, such as 304L stainless steel ribbon having a thickness in the minor dimension of less than 500 µm, an exemplary cold work conditioning steps may impart a cold work (or true strain) of as little as 60% (0.92 units), 85% (1.90 units) or 94% (2.81 units) and as much as 99.99% (9.21 units) or 99.999% (11.51 units), or within any range defined between any pair of the foregoing values.

For one form of 316L stainless steel, such as 316L stainless steel wire having a diameter of less than 500 µm, an exemplary cold work conditioning steps may impart a cold work (or true strain) of as little as 60% (0.92 units), 80% (1.61 units) or 90% (2.30 units) and as much as 99.9% (6.91 units) or 99.999% (11.51 units), or within any range defined between any pair of the foregoing values.

For another form of 316L stainless steel, such as 316L stainless steel ribbon having a thickness in the minor dimension of less than 500 µm, an exemplary cold work conditioning steps may impart a cold work (or true strain) of as little as 60% (0.92 units), 85% (1.90 units) or 92% (2.53 units) and as much as 99.95% (7.60 units) or 99.999% (11.51 units), or within any range defined between any pair of the foregoing values.

For materials conforming to the chemical compositional requirements of ASTM F1058, an exemplary cold work conditioning steps may impart a cold work (or true strain) of as little as 50% (0.69 units), 65% (1.05 units) or 92% (2.53 units) and as much as 99.0% (4.61 units), 99.9% (6.91 units) or 99.95% (7.60 units), or within any range defined between any pair of the foregoing values. These materials include, but are not limited to: FWM 1058 wire having a diameter of less than 500 µm; FWM 1058 ribbon having a thickness in the minor dimension of less than 500 µm; Conichrome wire having a diameter of less than 500 µm; Elgiloy® wire having a diameter of less than 500 µm; and Phynox wire having a diameter of less than 500 µm.

The cold work conditioning step by which the diameter of wire 10 is reduced significantly increases the crystallographic defect density via mechanisms including dislocations, stacking faults and deformation twins dependent upon the specific material system within wire 10 and creates an elongated crystal structure schematically shown at 14 in FIG. 3. The creation of the elongated crystal structure shown in FIG. 3 results from the individual crystals deforming plastically along material-intrinsic slip planes resulting in multi-axial strain, crystal rotation, and ultimately in an axially extended or elongated microstructure along the cold working direction. While a significant amount of the energy imparted during cold working is lost to heat generation, the amount of stored energy within each of the crystals or grains is substantially increased with increasing cold work deformation. This stored energy, and the defects which may act as grain nucleation sites, facilitate the process of recrystallizaton, as described in detail below.

2. Nano-recrystallization

After the cold work conditioning step, wire 10 is subjected to nano-recrystallization. Nano-recrystallization is the dynamic process of forming nanograins in a material and, as used herein, "nano-recrystallization" means a thermal treatment that is conducted under controlled time and temperature conditions to result in the formation of a submicron-scale grain structure as defined herein. In one exemplary embodiment, nano-recrystallization is achieved by annealing the cold work conditioned wire 10 to achieve a recrystallized, equiaxed crystal structure. In this embodiment, wire 10 is subjected to nano-recrystallization by heating wire 10 in a furnace, for example, to a nano-recrystallization temperature. As shown in FIG. 4, the nano-recrystallization step generates formation of submicron-scale, equiaxed crystals 16 in wire 10.

The nano-recrystallization is readily achieved due to the increase in the stored energy of each elongated crystal or grain formed in the cold work conditioning step, which allows a nanograin crystal structure to be quickly formed in wire 10 by the input of a relatively small amount of energy into wire 10 via the nano-recrystallization step. Cold work also creates a high density of grain-nucleation sites, such as stacking faults, dislocations, and other high-energy features, and increases the propensity of the material to form an ultrafine nanostructure.

Thus, in one exemplary embodiment, the nano-recrystallization temperature is substantially lower than conventional annealing temperatures for a given metal or metal alloy. The annealing dwell time of the nano-recrystallization step can range from a fraction of a second to minutes or hours. Shorter times of less than 1 second may be used at higher temperatures. Depending on the alloy being used, it may not be necessary that the material be quickly quenched following the nanorecrystallization or annealing step.

For example, for materials conforming to the chemical compositional requirements of ASTM F562, the nano-recrystallization temperature suitable to form a nanograin microstructure in accordance with the present process may be as low as 600° C., 750° C. or 810° C. and as high as 890° C., 900° C. or 950° C., with an anneal time of as short as 0.1 s, 0.2 s or 0.8 s and as long as 15 s, 120 s or 3600 s, or within any range defined between any pair of the foregoing values. These materials include, but are not limited to: MP35N® wire having a diameter of less than 500 µm; 35N LT® wire having a diameter of less than 500 µm; and 35N LT® ribbon having a thickness in the minor dimension of less than 500 µm.

For 304 stainless steel, the nano-recrystallization temperature suitable to form a nanograin microstructure in accordance with the present process may be as low as 600° C., 640° C. or 680° C. and as high as 760° C., 850° C. or 950° C., with an anneal time of as short as 0.1 s, 0.2 s or 0.8 s and as long as 8 s, 120 s or 3600 s, or within any range defined between any pair of the foregoing values. These materials include, but are not limited to 304L stainless steel wire having a diameter of less than 500 μm and 304L stainless steel ribbon having a thickness in the minor dimension of less than 500 μm.

For 316L stainless steel, the nano-recrystallization temperature suitable to form a nanograin microstructure in accordance with the present process may be as low as 600° C., 680° C. or 740° C. and as high as 820° C., 875° C. or 950° C., with an anneal time of as short as 0.1 s, 0.2 s or 0.8 s and as long as 8 s, 120 s or 3600 s, or within any range defined between any pair of the foregoing values. These materials include, but are not limited to 316L stainless steel wire having a diameter of less than 500 μm and 316L stainless steel ribbon having a thickness in the minor dimension of less than 500 μm.

For materials conforming to the chemical compositional requirements of ASTM F1058, the nano-recrystallization temperature suitable to form a nanograin microstructure in accordance with the present process may be as low as 600° C., 750° C. or 810° C. and as high as 890° C., 900° C. or 950° C., with an anneal time of as short as 0.1 s, 0.2 s or 0.5 s and as long as 12 s, 120 s or 3600 s, or within any range defined between any pair of the foregoing values. These materials include, but are not limited to: FWM 1058 wire having a diameter of less than 500 μm; FWM 1058 in the minor dimension having a thickness of less than 500 μm; Conichrome wire having a diameter of less than 500 μm; Elgiloy® wire having a diameter of less than 500 μm; and Phynox wire having a diameter of less than 500 μm.

The nano-recrystallization step may be conducted in any environment in which conventional metal processing is performed, such as in air, or optionally, may be conducted in an inert atmosphere such as nitrogen, a halogen gas, or a noble gas.

Figure 7:
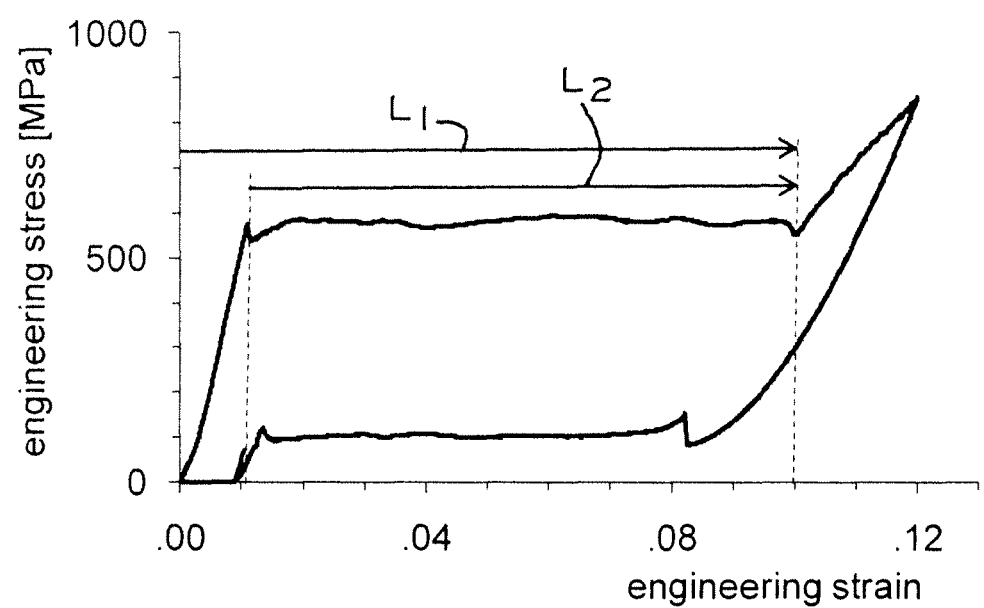
FIG. 7 is a graphical representation of engineering stress-strain data compiled in a cyclic uniaxial tension test.
Figure 23A:
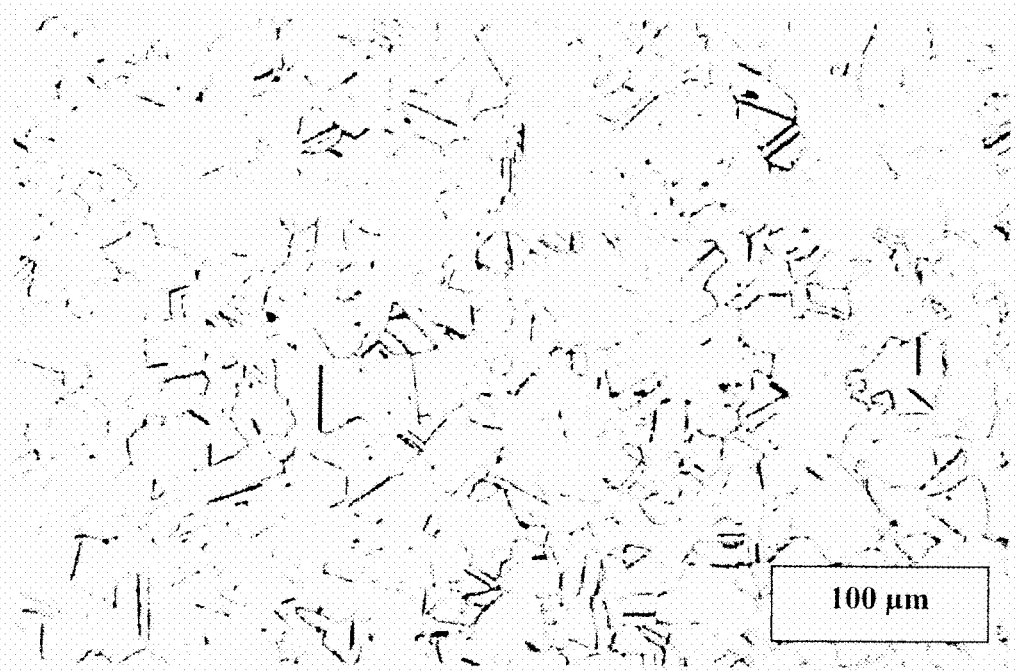
FIG. 23(a) is a micrograph of a cross-section of control 304L stainless steel alloy wire.

Advantageously, the cold work conditioning described in detail herein creates many more grain nucleation, or grain formation, sites than would typically be present in a standard material and requires less thermal energy to initiate a recrystallization process. As a result, recrystallization nuclei are formed which are spatially within nanometers of other recrystallization nuclei. Due to the recrystallization nuclei density and low thermal energy barrier, quenching just after heating to initiate recrystallization yields a consistent and nearly homogeneous nanograin structure, as shown in FIGS. 7 and 23(a) for 35N LT® alloy and Nitinol, respectively.

3. Additional Cold Working

Additionally, in some exemplary embodiments, the wire may be subjected to additional cold working. For example, MP35N® alloy or 35N LT® alloy may be drawn to achieve an area reduction, or cold work level, of as little as 5%, 10% or 15%, and as much as 60%, 70% or 99%, or within any range defined between any pair of the foregoing values, in order to increase the mechanical strength of the alloy while maintaining an exemplary level of resistance to fatigue damage.

4. Other Processing Parameters

Table 1 (shown below) lists exemplary processing parameters for various materials prepared in accordance with embodiments of the present process, as well as for "control" materials. As used herein, "control" materials are materials which have not received processing in accordance with the present process.

With reference the above discussion of manufacturing processes for non-shape memory biocompatible metal alloys, "intermediate strain" in Table 1 refers to the strain after the wire is drawn to the intermediate size and before the final draw and anneal. For materials prepared as described above, this "intermediate strain" is the strain after the cold work conditioning step.

"Final strain" is the strain after the final draw and anneal, when the wire has the diameter tabulated. The "final anneal temp" and "final anneal dwell" are for the final annealing process for the listed examples of Table 1. For materials prepared as described above, these exemplary parameters are descriptive of a nano-recrystallization step. In examples where the final strain is zero, this "final anneal" is the last thermomechanical step in the process, i.e., no additional cold work was applied. In examples where the final strain is greater than zero, the material underwent further processing after the final anneal, i.e. additional cold work was applied.

For example, Line 2 of Table 1 (35N LT® control material) refers to a wire made of 35N LT® which was drawn to 0.695 true strain, annealed at 1066° C. for less than 10 seconds, then drawn to 0.48 true strain for a finished diameter of 177 μm. Line 3 (35N LT®) refers to a wire made of 35N LT® which was drawn to 3.270 true strain (a cold-work conditioning step), annealed at 850° C. for less than 5 seconds (a nano-recrystallization step), and not drawn again after the annealing step (for a final strain of zero). Line 4 (35N LT®-HS) refers to a wire made of 35N LT® which was drawn to 3.100 true strain (a cold-work conditioning step), annealed at 850° C. for less than 3 seconds (a nano-recrystallization step), and a second draw after the annealing step (an additional cold work conditioning step) for a final true strain of 0.473 and a finished diameter of 177 μm. The additional cold work imparts an improved yield strength, as discussed below.

In Table 1, "HS" denotes a high strength material which has been subjected to additional cold work as described above; "F" denotes a flat ribbon or strip material (as opposed to a wire); and "FWM 1058" denotes a material made in accordance with the chemical compositional requirements of ASTM F1058 and available from Fort Wayne Metals Research Products Corporation of Fort Wayne, Ind. Properties of the materials shown in Table 1 are similarly tabulated in Table 3 (shown below in Section II). The materials of Table 1 are discussed in detail in Working Examples 1 and 3-8 in Section III below.

TABLE 1

Processing parameters for preparation of various example materials

| Material | Finished Diameter, μm (inch) | Intermediate strain (true strain) | Final strain (true strain) | Final anneal temp (° C.) | Final anneal dwell (s) |
|---|---|---|---|---|---|
| MP35N ® (control) | 177 (0.0070) | 0.695 | 0.480 | 1066 | <10 |
| 35N LT ® (control) | 177 (0.0070) | 0.695 | 0.480 | 1066 | <10 |
| 35N LT ® | 177 (0.0070) | 3.270 | 0.000 | 850 | <5 |
| 35N LT ® - HS | 76 (0.0030) | 3.100 | 0.473 | 850 | <3 |
| 35N LT ® - HS | 89 (0.0035) | 3.131 | 0.365 | 850 | <3 |
| 35N LT ® - F | 127 (0.0050) | 3.159 | 0.784 | 850 | <5 |
| FWM 1058 (control) | 225 (0.0089) | 1.152 | 0.478 | 1177 | <10 |
| FWM 1058 | 225 (0.0089) | 3.255 | 0.000 | 850 | <10 |
| 304L (control) | 177 (0.0070) | 2.095 | 0.713 | 1066 | <5 |
| 304L | 177 (0.0070) | 5.216 | 0.000 | 720 | <10 |
| 316L (control) | 177 (0.0070) | 2.095 | 0.713 | 1066 | <5 |
| 316L | 177 (0.0070) | 4.662 | 0.000 | 780 | <10 |

B. Shape Memory Materials

Various shape-memory materials may be made into a nanocystalline material via methods in accordance with the present process. Examples of shape-memory materials suitable for use with embodiments of the present process include Nitinol (a nickel-titanium, binary shape memory material), Nitinol tertiary or quaternary alloys (Nitinol with additive metals such as chromium, tantalum, palladium, platinum, iron, cobalt, tungsten, iridium, gold), and others.

In an exemplary method of manufacturing a shape-memory alloy wire having the properties and advantages set forth herein, Nitinol is first melted using any known method capable of generating an ingot that is suitable for subsequent hot, warm, and cold working into wire form. A combination of hot, warm, and cold working is used to generate Nitinol wire feed stock having a diameter of about 2 to 5 mm, for example. This feed stock is then oxidized and repetitively cold drawn and annealed using conventional wire drawing practices to an intermediate diameter as a suitable starting point for finished wire production.

Once drawn to the intermediate size, the wire is then continuously annealed under constant tension of 50-500 MPa (7-70 ksi) at any temperature between 450° C. (723 K) and 850° C. (1123 K), or within any range defined between any pair of values between the foregoing values.

The intermediate size of the wire is typically chosen to yield a finish retained cold work level that is as little as 15% or 25%, and as much as 50%, or 60%, or within any range defined between any pair of cold work values between the foregoing values, meaning that in the final finishing steps, the wire is drawn through one or more dies to impart between 15% and 45% cold work to the wire before the final annealing.

Figure 5:
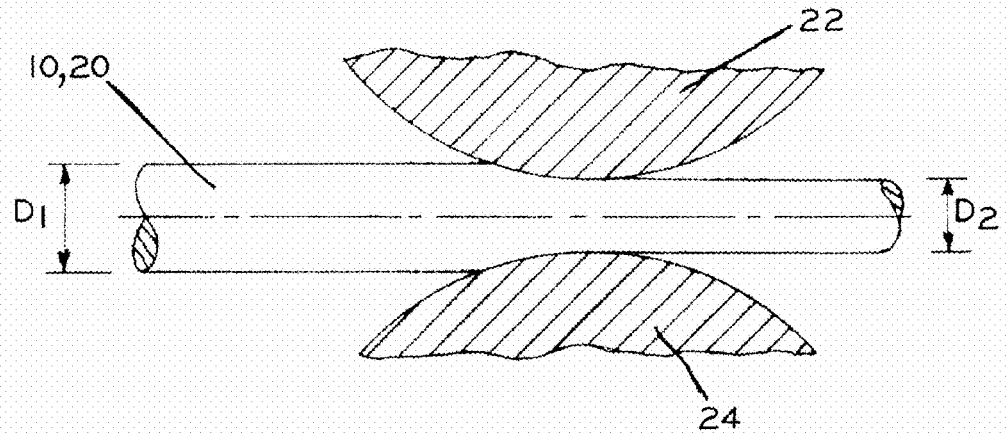
FIG. 5 is a schematic view illustrating an exemplary forming process of monolithic wire using a lubricated drawing die.

Final sizing is accomplished by pulling the intermediate wire through a series of diamond drawing dies. Referring to FIG. 5, wire 20 may be drawn or pulled through opposing diamond discs 22, 24 that are separated by a distance $D_2$, or otherwise drawn through any type of wire drawing die. Distance $D_2$ is smaller than the starting diameter $D_1$ of wire 20. As a result, as wire 20 exits from between discs 22, 24, is has a finish diameter that is substantially equal to distance $D_2$. Alternatively, final sizing of wire 20 may be accomplished by drawing wire 10 through a lubricated die, similar to wire 10 shown in FIG. 5 and discussed above.

The cold work (or true strain) imparted to a Nitinol material by the final sizing may range from 20% to 99.95% (0.22 units to 7.60 units). For example, exemplary cold work conditioning steps may impart a cold work (or true strain) of as little as 20% (0.22 units), 30% (0.36 units) or 35% (0.43 units) and as much as 95.0% (3.00 units), 99.0% (4.61 units) or 99.95% (7.60 units), or within any range defined between any pair of the foregoing values. Nitinol materials susceptible to this range of final cold work include, but are not limited to: Nitinol wire having a diameter of less than 500 µm; Nitinol ribbon or strip material having a thickness of less than 2 mm in the minor dimension; Nitinol tubing material having a wall thickness of less than 2 mm; and Nitinol rod materials having a diameter of less than 5 mm.

The final thermal treatment, or nano-recrystallization step, is an annealing step used to create the submicron-scale grain size. This annealing step drives a nano-recrystallization process without promoting nickel-rich precipitation and/or precipitate growth.

For most Nitinol alloys, the nano-recrystallization temperature suitable to form a nanograin microstructure in accordance with the present process may be as low as 300° C., 375° C. or 475° C. and as high as 510° C., 550° C. or 600° C., or within any range defined between any pair of the foregoing values. These alloys include, but are not limited to: Nitinol wire having a diameter of less than 500 µm; Nitinol ribbon or strip material having a thickness of less than 2 mm in the minor dimension; and Nitinol tubing material having a wall thickness of less than 2 mm.

For other Nitinol materials, such as Nitinol rod materials having a diameter of less than 5 mm, the nano-recrystallization temperature suitable to form a nanograin microstructure in accordance with the present process may be as low as 300° C., 375° C. or 450° C. and as high as 530° C., 550° C. or 600° C., or within any range defined between any pair of the foregoing values.

The annealing step is performed as a continuous annealing for a dwell time that may be as short as 0.1 s, 0.2 s or 2 s and as long as 90 s, 900 s or 5400 s, or within any range defined between any pair of the foregoing values, in order to limit the formation of precipitates. Nitinol materials susceptible to this range of dwell times at the above mentioned temperatures include, but are not limited to: Nitinol wire having a diameter of less than 500 µm; Nitinol ribbon or strip material having a thickness of less than 2 mm in the minor dimension; Nitinol tubing material having a wall thickness of less than 2 mm; and Nitinol rod materials having a diameter of less than 5 mm.

II. Description of Properties of Wires made in Accordance with the Present Manufacturing Process

A. Non-Shape Memory Biocompatible Metal Alloys

As discussed below, metallic and metallic alloy wires made in accordance with the present process exhibit several novel physical characteristics and/or novel combinations of physical characteristics, including the following:

1. Nanograin Microstructure.

Wires made in accordance with the present process, such as the process described in Section I-A above, exhibit a submicron-scale, or nanograin, microstructure. As used herein, "submicron-scale", "nanocrystalline" and "nanograin" refer to a crystal structure wherein the crystals, i.e., grains, have a mean crystal size of 500 nm or less, with "crystal size" referring to the greatest planar dimension across any given crystal across an arbitrary cross-section plane. In exemplary embodiments, such as depicted in FIG. 4, crystals 16 may have mean crystal or grain size as small as 10 nm, 50 nm, 75 nm, or 100 nm, or as great as 300 nm, 350 nm, 400 nm, 450 nm, or 500 nm, for example, or within any range defined between any pair of the foregoing values. Grain size may be determined by any suitable means for measuring grain size, including ASTM E112 and averaging the grain sizes.

In one exemplary method, electron microscopy is used to determine the mean crystal or grain size of a sample of material. Specifically, field emission scanning electron microscopy or transmission electron microscopy (TEM) is used to gather an image containing, for example, several hundred crystals or grains exhibiting strong grain boundary contrast. Examples of images gathered using TEM can be found in FIGS. 7, 10(*a*), and 11(*a*)-(*c*), for example. Next, the image is converted to a binary format suitable for particle measurement (as seen in FIG. 10(*b*)) using, for example, ImageJ software freely available online from the National Institutes of Health of Washington, D.C. Resolvable grains are modeled with ellipsoids (see FIG. 10(*c*)) and subsequently measured digitally yielding statistics regarding the crystal or grain size, such as the mean size, maximum size, and minimum size. The resulting mean crystal size is taken to be the mean crystal size for the material from which the sample was taken.

2. High-Cycle Fatigue Strength.

The submicron-scale crystal or grain size of material made in accordance with the present process results in significantly improved high cycle fatigue strength of the nanocrystalline material, as determined by rotary beam fatigue testing, as described in "A Hierarchical Initiation Mechanism Approach to Modeling Fatigue Life Variability in 35co-35ni-20cr-10mo Alloy Medical Grade Fine Wire" by Jeremy E. Schaffer (Purdue University), published August 2007 and in "Characterizing Fatigue Response of Nickel-Titanium Alloys by Rotary Beam Testing" by Mitesh Patel published in the Journal of ASTM International, Vol. 4, No. 6. The term "high cycle fatigue strength" as used herein refers to, for example, the fatigue strength or alternating stress level at greater than 1 million cycles to failure.

This improvement is believed to result from two interdependent phenomena, including an increased energy requirement for dislocation propagation through the grain-boundary-constrained matrix, since dislocations are mediators of permanent plastic damage in crystalline materials, and due to texture-effects, where texture-effects are associated with non-random crystallographic orientation distribution driven by the nano-recrystallization process after cold work conditioning, which increase the compliance of the material in the load-bearing axial direction. For example, in conventional MP35N® alloy wire with grain sizes exceeding 1000 nm (1 μm), primary fatigue damage results from formation of dislocation-mediated micro-cracks near or around surface or sub-surface stress concentrations. In nanograin MP35N® alloy wire, such as wire with a mean 200 nm grain size for example, it is much more difficult for these types of dislocations to move or propagate because the dislocations are hindered by stress fields associated with the higher content or incidence of grain boundaries, and the resolved shear stress forcing the dislocations is reduced due to texture-effects as discussed in the next section. Consequently, the high cycle fatigue strength and material yield strength is increased for a given ultimate tensile strength level.

3. Crystal Orientation.

The present process has been shown to enhance crystallographic texture and has been shown to generate a non-random, process-specific, crystal orientation distribution, or texture. As discussed below, powder electron diffraction patterns show evidence of a non-random crystal orientation distribution. For example, referring to the powder electron diffraction pattern shown in the upper right hand corner of FIG. 6, what would typically appear as randomly dispersed dotted rings in a known equiaxed microcrystalline material instead appear as a pattern including high intensity spots 40 that primarily evidence a [100] zone axis, i.e., an axis normal to the transverse wire orientation.

The unique characteristic of preferred orientation is metal and/or metal alloy specific, and also process specific, and may or may not be present in all embodiments of wire manufactured in accordance with the present process. For example, as shown herein, a non-random crystal orientation distribution has been observed in wires produced from MP35N® alloy according to the present process, while more random nanograin distributions have been observed in wires produced from binary Nitinol (nickel-titanium) shape memory alloy according to the present process.

This texture phenomenon is believed to be related to the tendency for MP35N® alloy to undergo fiber texturization during cold wire drawing due to crystal rotation effects associated with plastic deformation along specific slip systems, where slip systems are defined as specific directions within the crystal along which crystal deformation or slip occurs, and to some degree even after recrystallization. The cold work conditioning step of the present process creates preferred grain nucleation sites that fall along non-randomly deformed slip planes, twin boundaries, or other crystallographic features.

The strength and sense of texture can be analyzed by electron microscopy using various techniques including TEM and electron backscatter diffraction (EBSD) techniques. In EBSD a 10 to 40 keV electron beam is used to probe a polished surface, such as a transverse wire cross-section, and the scattered beam is collected as an image and geometrically analyzed to determine crystal orientations throughout the section for many crystals. The end result of successful EBSD analysis is statistical quantification of crystal orientation throughout the specimen in question, which can be displayed as an orientation map in a technique called orientation imaging microscopy (OIM). Conventional annealing practice significantly overcomes the initial orientation set by the nucleating feature due to high diffusion associated with increased thermal energy and effectively yields a random orientation. By contrast, exemplary processes described herein for preparing MP35N® alloy preserve texture, resulting in unique material anisotropy controllable by pre-anneal deformation and thermal processing parameters.

4. Fatigue Endurance.

Conventional metallic wires made of medical grade materials possess an alternating fatigue strain limit, hereinafter referred to as an endurance limit, below which the material will last for tens of millions of fatigue cycles before experiencing fatigue failure. Specifically, conventional metallic wires having a micrograin crystalline structure and a modulus exceeding $25 \times 10^6$ psi have an endurance limit near or below 0.35% alternating strain as measured by rotary beam fatigue testing of smooth specimens in accordance with the methods discussed in "A Hierarchical Initiation Mechanism Approach to Modeling Fatigue Life Variability in 35co-35ni-20cr-10mo Alloy Medical Grade Fine Wire" by Jeremy E. Schaffer, published August 2007.

By contrast, metallic wires having a nanocrystalline structure and made in accordance with the present process have an endurance limit that is 20% to 130% above the endurance limit of conventional metallic wires having a micrograin crystalline structure, as shown, for example, in FIG. 8 and discussed in Examples 1 and 3-7 below.

For example, as shown in Table 2 below, an improvement in fatigue load capability has been demonstrated in wires made in accordance with the present process as compared with experimental control materials, with some nanograin materials showing a 100% increase in high-cycle (i.e., $10^8$ cycles) strain tolerance. The materials of Table 2 are discussed in detail in Examples 1 and 5-7 in Section III below.

TABLE 2

Fatigue load capability of various materials.

| Material | Fatigue load capability (strain at 10 8 cycles) | Percentage difference |
|---|---|---|
| MP35N ® (control) | 0.266% | 0% |
| 35N LT ® (control) | 0.355% | 33% |
| 35N LT ® | 0.600% | 125% |
| FWM 1058 (control) | 0.305% | 0% |
| FWM 1058 | 0.450% | 48% |
| 304L (control) | 0.350% | 0% |
| 304L | 0.450% | 29% |
| 316L (control) | 0.250% | 0% |
| 316L | 0.350% | 40% |

5. Ductility, Fatigue Strength, and Yield Strength.

Axial wire ductility is an important metric in the determination of the suitability of a metallic material for various forming applications such as, for example, coiling for pacemaker lead components, and cabling for biostimulation leads. Axial wire ductility is also important in determining the toughness of a wire and the ability of a wire to withstand stress in the human body. Conventional wire manufacturing practices reduce material ductility while increasing material high cycle fatigue strength and yield strength. Conventionally, ductility is restored through annealing with concomitant recrystallization, grain growth, and reductions in yield strength and high cycle fatigue strength.

One measure of the stiffness of a material in a given loading direction is known as Young's Modulus of elasticity, hereinafter referred to as the axial wire direction or simply as modulus. Materials possessing high modulus will resist deformation with greater force for a given increment of elastic axial deformation than materials with relatively low modulus. In this case, the material with relatively low modulus is more compliant and stores less internal elastic energy for a given elastic strain increment resulting in less internal stress and potential fatigue-crack driving force. This is believed to be another phenomenon responsible for the improved strain-controlled fatigue performance of wire made according to the present process.

The present process has been found to impart a high relative degree of ductility, such as greater than about 2%, 4% or 8% axial engineering strain to failure for a monofilament wire, and greater than about 1.5%, 3% or 6% axial engineering strain to failure for a cabled or braided product, while enhancing fatigue strength and preserving a high yield strength and a high yield to ultimate strength ratio. For example, as shown and discussed below in the Examples for wires made from biocompatible materials according to the present process, combined properties of greater than 8% axial engineering strain to rupture and a yield to ultimate strength ratio exceeding 90% are observed for some wire materials. This unique and favorable combination of ductility, high fatigue threshold/damage tolerance, and yield strength is advantageous for a variety of applications. Table 3 below includes illustrates fatigue and strength characteristics of control and exemplary wire materials made in accordance with the present process.

B. Biocompatible Metal Alloys with Additional Cold Work

As discussed above, a wire made of materials complying with the chemical compositional requirements of ASTM F562, for example, may optionally be subjected to additional cold working following nano-recrystallization. When further cold work is performed, the wire may demonstrate novel physical characteristics and/or novel combinations of physical characteristics, including the following:

1. Increased Ultimate Strength.

Nanocrystalline wire made in accordance with the present process, such as the wire described above, may exhibit additional ultimate rupture strength. This additional strength may help the wire resist overload in some devices, such as medical devices including cardiac pacing leads or defibrillation lead wires, as discussed in detail below in Section IV. For example, additional cold working (as discussed in detail herein) in an alloy conforming to the chemical compositional requirements of ASTM F562 and prepared in accordance with the present process has demonstrated ultimate strength values of up to 1900 MPa compared to strength levels of 1400 to 1500 MPa for similar nanocrystalline alloy materials without any further cold working. This cold worked material may be further thermally treated at temperatures as low as 300° C. or as high as 800° C. in order to increase the ultimate strength to as high as 2200 to 2500 MPa.

2. Shape Stabilization.

In some applications, shape stabilization through a post-forming thermal treatment may be desired. Some such applications, as discussed in Section IV, include coronary lead manufacture, coil manufacture, or cable manufacture, for example. In these cases, nanocrystalline material manufactured in accordance with the embodiments of the present process, when subsequently subjected to additional cold working, can provide further benefits due to stored microstructural energy. For example, materials such as MP35N® alloy require stored energy in order to substantially react at low temperatures, e.g., temperatures as low as 550° C., 625° C. or 750° C. or as high as 870° C., 900° C. or 950° C., or within any range defined between any pair of the foregoing values. Without additional cold working as described herein, the nanorecrystallized material may not react as advantageously to stabilize the target part shape.

In addition, materials made in accordance with the present process demonstrate improved tensile properties as compared with control materials. For example, Table 3 below shows improvements in wire made in accordance with the present process, such as high strength and/or the ability to withstand greater strain before rupturing. For example, Table 3 below shows improvement in wire made in accordance with the present process, such as high strength and/or the ability to withstand greater strain before rupturing and/or increased yield to ultimate strength ration indicative of a relatively small residual stress gradient in a material. In Table 3, "HS" denotes a high strength material which has been subjected to additional cold work as described above; "F" denotes a flat ribbon or strip material (as opposed to a round wire); and "FWM 1058" denotes a material made in accordance with the chemical compositional requirements of the chemical compositional requirements of ASTM F1058 as discussed above. The materials of Table 3 are discussed in detail in Working Examples 1 and 3-8 in Section III below.

TABLE 3

Tensile properties of various control and nanograin materials

| Material | Diameter μm (inch) | Yield strength MPa (ksi) | Ultimate tensile strength MPa (ksi) | Strain to rupture | YS/UTS |
|---|---|---|---|---|---|
| MP35N ® (control) | 177 (0.0070) | 1680 (243.6) | 1931 (280.0) | 3.0% | 0.87 |
| 35N LT ® (control) | 177 (0.0070) | 1680 (243.6) | 1931 (280.0) | 3.0% | 0.87 |
| 35N LT ® | 177 (0.0070) | 1393 (202.0) | 1462 (212.0) | 13.5% | 0.95 |
| 35N LT ® - HS | 76 (0.0030) | 1637 (237.4) | 1916 (277.9) | 3.0% | 0.85 |
| 35N LT ® - HS | 89 (0.0035) | 1646 (238.7) | 1896 (275.0) | 2.9% | 0.87 |
| 35N LT ® - F | 127 (0.0050) | 1437 (208.4) | 1476 (214.1) | 15.1% | 0.97 |
| FWM 1058 (control) | 225 (0.0089) | 1669 (242.0) | 1862 (270.0) | 3.5% | 0.90 |
| FWM 1058 | 225 (0.0089) | 1314 (190.5) | 1409 (204.3) | 17.9% | 0.93 |
| 304L (control) | 177 (0.0070) | 1256 (182.1) | 1426 (206.8) | 2.7% | 0.88 |
| 304L | 177 (0.0070) | 924 (134.0) | 1242 (180.1) | 11.9% | 0.74 |
| 316L (control) | 177 (0.0070) | 1218 (176.7) | 1360 (197.3) | 2.9% | 0.90 |
| 316L | 177 (0.0070) | 861 (124.9) | 952 (138.1) | 12.3% | 0.90 |

Shape-Memory Material

The use of a manufacturing process in accordance with the present process, such as the process described in Section I-B above, can be applied to NiTi shape memory alloys including Nitinol, to result in the creation of a NiTi wire having a grain size as small as less than 1 nm, 10 nm, or 25 nm, and as large as 75 nm, 150 nm or 350 nm, or within any range defined between any pair of the foregoing values. In addition, metallic and metallic alloy wires made in accordance with the present process exhibit several novel physical characteristics and/or novel combinations of physical characteristics, including the following:

1. Lack of Precipitates.

Equiaxed and homogeneous microstructure was generated in Nitinol wire having a diameter of 177 μm, with mean grain sizes ranging from 50 nm to 10 μm. Evidence demonstrates that all of the materials were free of Ni-rich lenticular precipitates. In one exemplary embodiment, the materials were substantially free of $Ti_xNi_y$ precipitates which were visible in standard bright field tem analysis. In another exemplary embodiment, the materials were free of $Ti_xNi_y$ precipitates which exceeded 5 nm in size. As a result of the nanocrystalline, precipitate-free microstructure, the total transformation strain capability, depicted by plateau length $L_2$ in FIG. 7 of the material is improved.

2. Active Austenitic Transformation Temperature.

Figure 14:
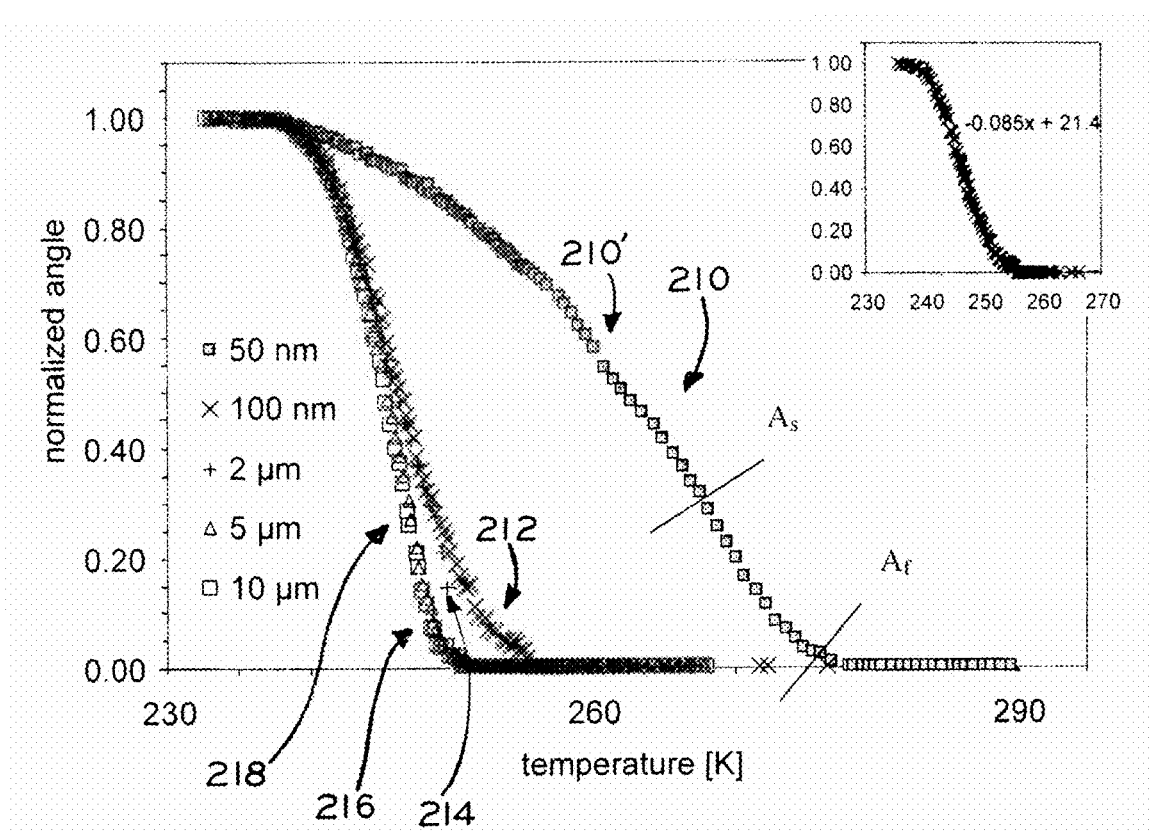

An extended bend and stress-free strain recovery with possible multistage character was found in samples with a mean grain size less than about 100 nm. This increase in the active austenitic transformation finish temperature ($A_f$), shown in FIG. 14 and discussed in more detail below, is postulated to result primarily from the high grain boundary energy density and to grain constraint effects in the nanocrystalline wire. A concomitant rise in the austenitic start temperature ($A_s$), also shown in FIG. 14, was not observed in these samples, suggesting a lack of matrix Ni deficiency as would be expected from the various Ni-rich precipitation reactions. In exemplary embodiments, the resulting material had an $A_f$ that was below 325 K.

3. Unloading Plateau Strength and Ultimate Tensile Strength.

Reduction in grain size was accompanied by significant increases in both unloading plateau strength (schematically represented by the lower approximately zero-slope portion of the curve shown FIG. 7) and ultimate tensile strength combined with the extinction of permanent set. In one exemplary embodiment, shown in FIG. 14 and discussed in detail below, the material had an ultimate tensile strength of greater than 1100 MPa.

4. Strength Properties.

Figures 15A, 15B, 15C, 15D:
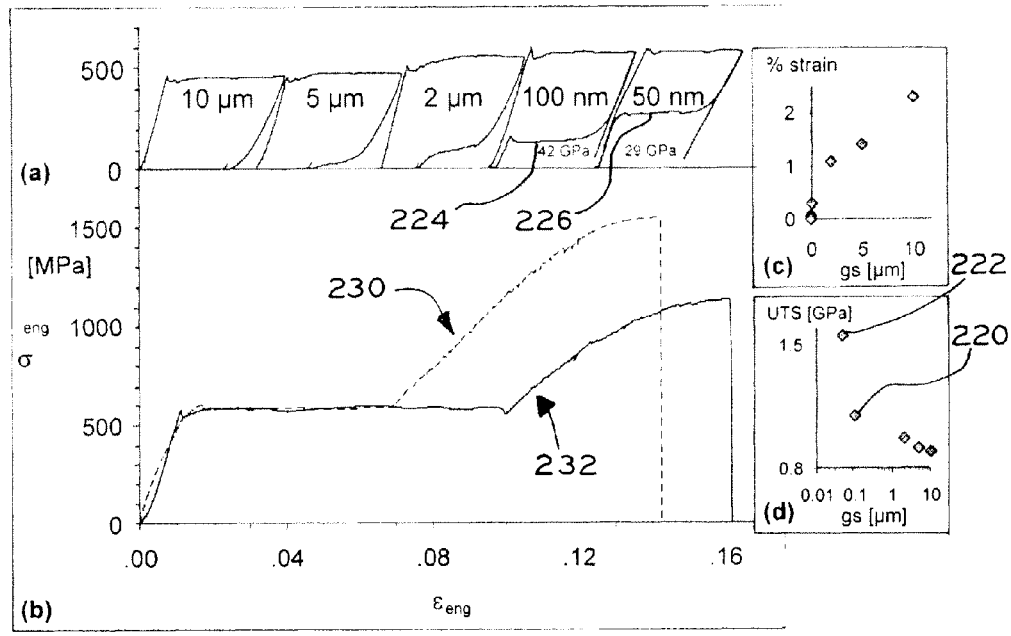
FIG. 15(a) is a graphical representation of engineering stress-strain data ran at a temperature of 298 K in quiescent air at a strain rate of $10^{-3}$ s$^{-1}$, showing 4% hysteresis loops as a function of equiaxed grain size with unloading moduli and values provided.
FIG. 15(b) is a graphical representation of a monotonic loading curves for standard superelastic material and wire with a homogeneous 100 nm, precipitate-free matrix.
FIG. 15(c) is a graphical representation of permanent set strain as a function of grain size.
FIG. 15(d) is a graphical representation of ultimate tensile strength as a function of grain size.

A 40% increase in strength properties occurred between grain sizes of 100 and 50 nm, as shown in FIG. 15(d). It is possible that these effects may be related to martensite variant activity and subsequent elastic loading of the fully accommodated microstructure in combination with classical fine grain strengthening effects.

5. Zero Permanent Set in a 4% Strain Cycle.

Zero permanent set in a 4% strain cycle was demonstrated in an equiaxed, precipitate-free and untrained material with a mean 50 nm grain size, as shown in FIG. 15(c) and discussed in detail below.

6. Recoverable Strain.

Referring to FIG. 7, isothermal Nitinol recoverable engineering strains of 9.6%, which are shown as $L_1$ in FIG. 7 and are greater than 90% of the theoretical limit in the [123] orientation, were demonstrated in nanocrystalline Nitinol wire. This testing was performed as a uniaxial tensile test at a temperature T equal to 298±5K, or $A_f$+10K. In the precipitate-free structure with a 100 nm equiaxed grain size, the transformation plateau extended to greater than 10% axial engineering strain and terminated at 10.1% axial engineering strain, providing an axial engineering strain to rupture of greater than 10% strain with less than 1% non-recoverable strain. Thus, the total recoverable strain without thermal perturbation was in excess of 9%. Further, the long-plateau behavior was attributed to preferential conditions for homogeneous transformation including a reduced defect density state, yielding greater available transformation volume and possible texture effects.

7. Correlation of Unloading Stiffness with Grain Size.

The unloading stiffness was found to decrease, stepwise, from 42 GPa to 29 GPa moving from 100 nm to the 50 nm grain size, as shown in FIG. 15(a). This behavior may be the result of energetic competition between single and compound martensite variants. The mechanistic description of stiffness modification may facilitate the design of devices, such as Nitinol stents, where loading and unloading stiffness are dynamically important in both the device function and vessel response.

8. Combination of Resilience, Strain Transformation, Mechanical Strength and Fatigue Strain Threshold.

Typical Nitinol products which are designed for pseudoelasticity are generally heated to approximately 773K for greater than 60 s. This typical process results in a material with good resilience and a plateau length ($L_1$ in FIG. 7) that is less than about 7.1% strain. Conventional wisdom suggests that equiaxed, annealed Nitinol should show poor elastic resilience and a high level of plastic flow during strain cycling. However, as discussed above, materials made in accordance with the present process yield a nanocrystalline, equiaxed, Nitinol wire with good resilience, an extended strain transformation plateau (due to combined effects of low precipitate density and texture), and good mechanical strength (>1199 MPa UTS), as well as a fatigue strain threshold exceeding 0.9% at $10^6$ cycles.

III. EXAMPLES

The following non-limiting Examples illustrate various features and characteristics of the present process, which are not to be construed as limited thereto.

Example 1

Manufacturing of Alloy Wires Conforming to the Chemical Composition Requirements ASTM F562 having a Nanograin Crystal Structure, and Characterization of the Physical Properties of Such Wires In this Example exemplary wires made in accordance with the chemical compositional requirements of ASTM F562 in the form of 35N LT® wires having a diameters ranging from 0.0030-in (0.076 mm) to 0.0070-in (0.18 mm) were produced and tested. The wires exhibited wire properties and characteristics in accordance with an embodiment of the present process.

1. Experimental Technique

The process started with a VIM (vacuum induction melted)/VAR (vacuum arc remelted) 35N LT® ingot that was processed by hot rolling into rod stock. The material was then iteratively cold worked and annealed in a conventional manner to a diameter of 1.6 mm. A conventional anneal step at 1.6 mm was followed by cold drawing the material through round diamond dies to 0.91 mm. Then, the material was conventionally annealed to produce an equiaxed grain structure with a mean grain size of about 1 to 5 μm.

With respect to the cold work conditioning and nano-recrystallization steps of the present process, it has been found that preparation of 35N LT® alloy for nano-recrystallization entails a relatively high amount of deformation in the cold work conditioning step.

In the present example, annealed wires having diameters ranging 0.45-0.91 mm were subjected to a cold work conditioning steps by drawing to a diameter as low as 0.0030-in (0.076 mm) and as large as 0.0070 (0.18 mm) in preparation for nanorecrystallization. According to Formula I above, the cold work conditioning steps therefore imparted up to 98% cold work to the material.

2. Results

Figure 6:
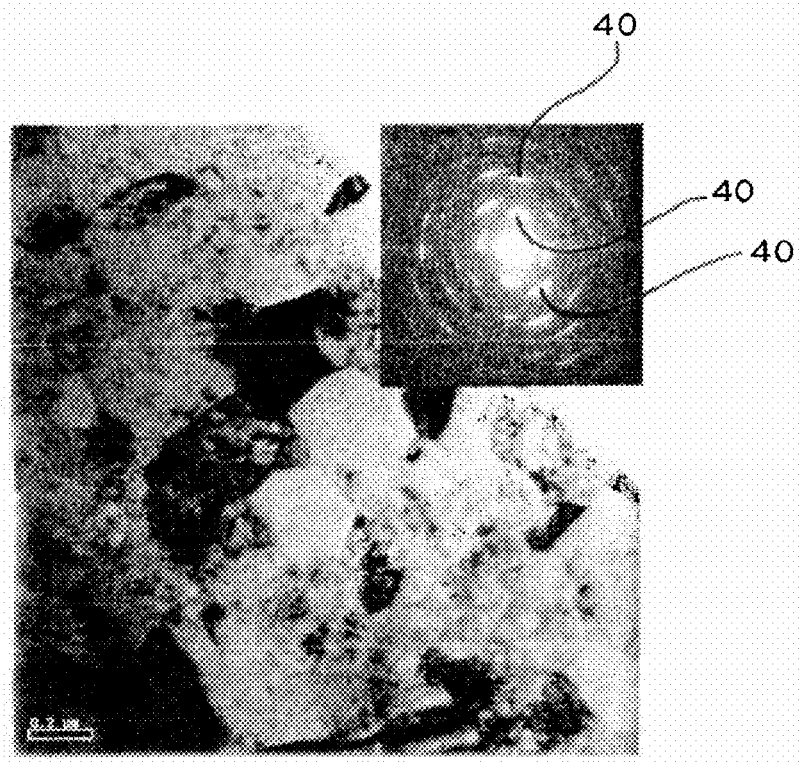
FIG. 6 is a micrograph of a cross-section of nanocrystalline 35N LT® alloy wire manufactured in accordance with an exemplary embodiment of the present process taken using bright field transmission electron microscopy (BFTEM) imaging and a diffraction pattern of the same.

The nano-recrystallization step was performed at 850° C. at a dwell time of about 2-3 seconds. The resultant nanograin crystal structure is shown in FIG. 6 and, referring to the powder electron diffraction pattern shown in the upper right hand corner of FIG. 6, the non-random crystal orientation distribution is shown. Specifically, what would typically appear as randomly spaced dotted rings in a known equiaxed microcrystalline material instead appear as a pattern including high intensity spots 40 that primarily evidence a [100] zone axis, i.e., an axis normal to the transverse wire orientation.

Figure 8:
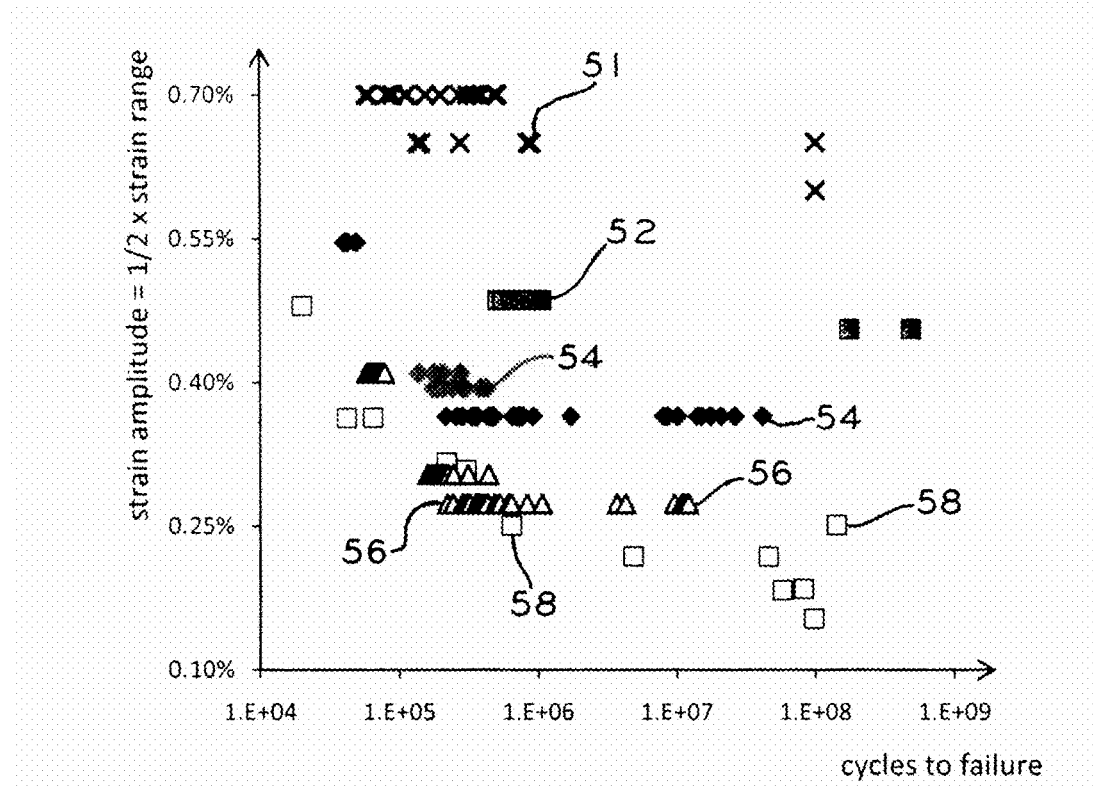
Figures 9A, 9B, 9C, 9D:
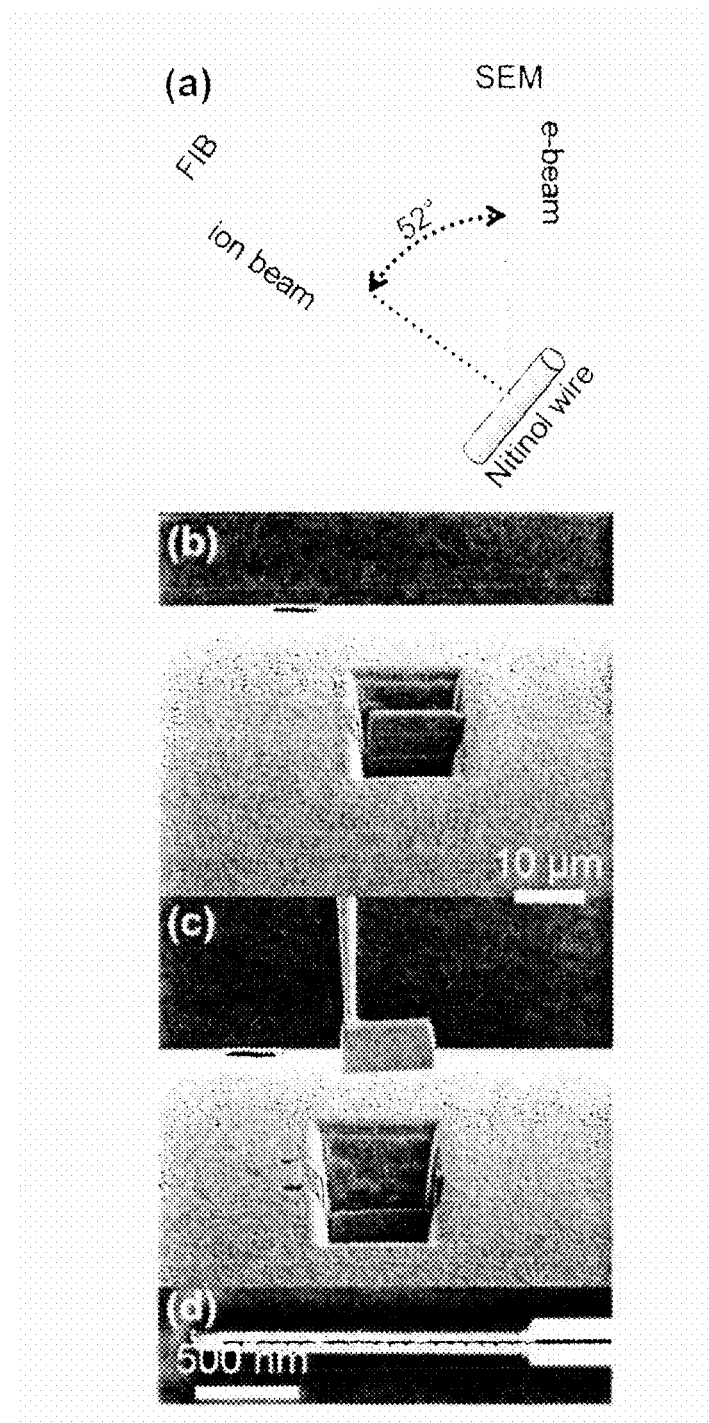

Referring to FIG. 8, a comparison of the endurance limit, as determined by rotary beam fatigue testing, for various wires manufactured in accordance with exemplary embodiments of the present process to conventional wire designs is graphically depicted and discussed below.

Data points 51, illustrated as x-shaped marks in FIG. 8 and tabulated below in Table 4A, were generated using 0.0030-in (0.076 mm) diameter 35N LT® alloy wire manufactured in accordance with the present process (discussed in detail below in Example 4 herein). As shown by data points 51 in FIG. 8 and Table 4A, this wire was shown to withstand a stress amplitude in excess of 1350 MPa and an engineering strain of at least 0.60.

TABLE 4A

Fatigue data, 35N LT ® alloy NANOGRAIN wire, dia. 76 μm

| Lifetime (cycles) | Stress (Mpa) | Strain (mm/mm) | Wire Dia. (μm) |
| --- | --- | --- | --- |
| 1.000E+08 | 1362 | 0.6 | 75 |
| 1.000E+08 | 1362 | 0.6 | 75 |
| 1.000E+08 | 1362 | 0.6 | 75 |
| 1.000E+08 | 1362 | 0.6 | 75 |
| 1.000E+08 | 1362 | 0.6 | 75 |
| 1.000E+08 | 1362 | 0.6 | 75 |
| 1.000E+08 | 1362 | 0.6 | 75 |
| 1.000E+08 | 1475.5 | 0.65 | 75 |
| 1.000E+08 | 1475.5 | 0.65 | 75 |
| 1.457E+05 | 1475.5 | 0.65 | 75 |
| 1.381E+05 | 1475.5 | 0.65 | 75 |
| 2.771E+05 | 1475.5 | 0.65 | 75 |
| 1.000E+08 | 1475.5 | 0.65 | 75 |
| 8.928E+05 | 1475.5 | 0.65 | 75 |
| 9.130E+04 | 1589 | 0.7 | 75 |
| 1.576E+05 | 1589 | 0.7 | 75 |
| 5.821E+04 | 1589 | 0.7 | 75 |
| 1.153E+05 | 1589 | 0.7 | 75 |
| 6.070E+04 | 1589 | 0.7 | 75 |
| 8.262E+04 | 1589 | 0.7 | 75 |
| 1.133E+05 | 1589 | 0.7 | 75 |
| 4.852E+05 | 1589 | 0.7 | 75 |

TABLE 4A-continued

Fatigue data, 35N LT ® alloy NANOGRAIN wire, dia. 76 μm

| Lifetime (cycles) | Stress (Mpa) | Strain (mm/mm) | Wire Dia. (μm) |
| --- | --- | --- | --- |
| 5.079E+05 | 1589 | 0.7 | 75 |
| 3.484E+05 | 1589 | 0.7 | 75 |
| 3.924E+05 | 1589 | 0.7 | 75 |
| 2.736E+05 | 1589 | 0.7 | 75 |
| 3.147E+05 | 1589 | 0.7 | 75 |
| 2.005E+05 | 1589 | 0.7 | 75 |
| 1.000E+08 | 1475.5 | 0.65 | 75 |
| 8.412E+05 | 1475.5 | 0.65 | 75 |
| 1.000E+08 | 1475.5 | 0.65 | 75 |

Data points 52, illustrated as filled square-shaped marks in FIG. 8 and tabulated below in Table 4B, were generated using 0.0070-in (0.18 mm) diameter 35N LT® alloy wire manufactured in accordance with the present process. As shown by data points 52 in FIG. 8, this wire was shown to withstand a stress amplitude in excess of 1000 MPa and an engineering strain of greater than 0.450.

TABLE 4B

Fatigue data, 35N LT ® alloy NANOGRAIN wire, dia. 177 μm

| Lifetime (cycles) | Stress (Mpa) | Strain (mm/mm) | Wire Diameter (μm) |
| --- | --- | --- | --- |
| 6.378E+05 | 1103 | 0.486 | 177 |
| 5.089E+05 | 1103 | 0.486 | 177 |
| 6.319E+05 | 1103 | 0.486 | 177 |
| 8.068E+05 | 1103 | 0.486 | 177 |
| 6.330E+05 | 1103 | 0.486 | 177 |
| 6.070E+05 | 1103 | 0.486 | 177 |
| 7.168E+05 | 1103 | 0.486 | 177 |
| 5.582E+05 | 1103 | 0.486 | 177 |
| 1.053E+06 | 1103 | 0.486 | 177 |
| 8.205E+05 | 1103 | 0.486 | 177 |
| 1.750E+08 | 1034 | 0.456 | 177 |
| 4.860E+08 | 1034 | 0.456 | 177 |

In contrast, the other, traditional wires plotted on the chart failed at a stress amplitude of less than about 900 MPa and a strain amplitude of less than 0.400. For example, a standard micro-crystalline wire made of MP35N® with a diameter of 177 μm and a mean grain size of approximately 3 μm generated data points 54, shown as diamond shaped marks in FIG. 8 and tabulated below in Table 4C, demonstrating failure at less than 900 MPa and an engineering strain of less than 0.400.

TABLE 4C

Fatigue data, MP35N ® standard wire, dia. 177 μm, 3 μm mean grain size

| Lifetime (cycles) | Stress (Mpa) | Strain (mm/mm) | Wire Dia. (μm) |
| --- | --- | --- | --- |
| 2.173E+05 | 828 | 0.365 | 177 |
| 2.583E+05 | 828 | 0.365 | 177 |
| 2.849E+05 | 828 | 0.365 | 177 |
| 3.345E+05 | 828 | 0.365 | 177 |
| 3.530E+05 | 828 | 0.365 | 177 |
| 3.642E+05 | 828 | 0.365 | 177 |
| 4.398E+05 | 828 | 0.365 | 177 |
| 4.507E+05 | 828 | 0.365 | 177 |
| 4.614E+05 | 828 | 0.365 | 177 |
| 4.764E+05 | 828 | 0.365 | 177 |
| 6.513E+05 | 828 | 0.365 | 177 |
| 6.567E+05 | 828 | 0.365 | 177 |

TABLE 4C-continued

Fatigue data, MP35N ® standard wire, dia. 177 μm, 3 μm mean grain size

| Lifetime (cycles) | Stress (Mpa) | Strain (mm/mm) | Wire Dia. (μm) |
|---|---|---|---|
| 7.052E+05 | 828 | 0.365 | 177 |
| 7.292E+05 | 828 | 0.365 | 177 |
| 7.473E+05 | 828 | 0.365 | 177 |
| 7.699E+05 | 828 | 0.365 | 177 |
| 7.717E+05 | 828 | 0.365 | 177 |
| 9.174E+05 | 828 | 0.365 | 177 |
| 1.725E+06 | 828 | 0.365 | 177 |
| 8.027E+06 | 828 | 0.365 | 177 |
| 8.568E+06 | 828 | 0.365 | 177 |
| 1.009E+07 | 828 | 0.365 | 177 |
| 1.401E+07 | 828 | 0.365 | 177 |
| 1.511E+07 | 828 | 0.365 | 177 |
| 1.747E+07 | 828 | 0.365 | 177 |
| 1.751E+07 | 828 | 0.365 | 177 |
| 2.093E+07 | 828 | 0.365 | 177 |
| 2.634E+07 | 828 | 0.365 | 177 |
| 4.155E+07 | 828 | 0.365 | 177 |
| 1.747E+05 | 896 | 0.395 | 177 |
| 1.844E+05 | 896 | 0.395 | 177 |
| 1.894E+05 | 896 | 0.395 | 177 |
| 2.079E+05 | 896 | 0.395 | 177 |
| 2.411E+05 | 896 | 0.395 | 177 |
| 2.832E+05 | 896 | 0.395 | 177 |
| 2.852E+05 | 896 | 0.395 | 177 |
| 2.964E+05 | 896 | 0.395 | 177 |
| 3.799E+05 | 896 | 0.395 | 177 |
| 4.185E+05 | 896 | 0.395 | 177 |
| 1.380E+05 | 931 | 0.410 | 177 |
| 1.766E+05 | 931 | 0.410 | 177 |
| 2.043E+05 | 931 | 0.410 | 177 |
| 2.722E+05 | 931 | 0.410 | 177 |
| 4.007E+04 | 1241 | 0.547 | 177 |
| 4.165E+04 | 1241 | 0.547 | 177 |
| 4.295E+04 | 1241 | 0.547 | 177 |
| 4.943E+04 | 1241 | 0.547 | 177 |

A micro-crystalline wire generated data points 56, shown as trianglular marks in FIG. 8 and tabulated below in Table 4D, demonstrating failure at less than 700 MPa and an engineering strain of less than 0.310.

TABLE 4D

Fatigue data for MP35N ® standard wire, dia. 177 μm

| Lifetime (cycles) | Stress (Mpa) | Strain (mm/mm) | Wire Dia. (μm) |
|---|---|---|---|
| 2.229E+05 | 621 | 0.27357 | 177 |
| 2.450E+05 | 621 | 0.27357 | 177 |
| 2.862E+05 | 621 | 0.27357 | 177 |
| 2.934E+05 | 621 | 0.27357 | 177 |
| 3.064E+05 | 621 | 0.27357 | 177 |
| 3.212E+05 | 621 | 0.27357 | 177 |
| 3.552E+05 | 621 | 0.27357 | 177 |
| 3.591E+05 | 621 | 0.27357 | 177 |
| 3.707E+05 | 621 | 0.27357 | 177 |
| 3.768E+05 | 621 | 0.27357 | 177 |
| 3.827E+05 | 621 | 0.27357 | 177 |
| 3.871E+05 | 621 | 0.27357 | 177 |
| 3.875E+05 | 621 | 0.27357 | 177 |
| 4.169E+05 | 621 | 0.27357 | 177 |
| 4.279E+05 | 621 | 0.27357 | 177 |
| 4.302E+05 | 621 | 0.27357 | 177 |
| 4.870E+05 | 621 | 0.27357 | 177 |
| 4.918E+05 | 621 | 0.27357 | 177 |
| 5.290E+05 | 621 | 0.27357 | 177 |
| 6.103E+05 | 621 | 0.27357 | 177 |
| 6.106E+05 | 621 | 0.27357 | 177 |
| 6.392E+05 | 621 | 0.27357 | 177 |
| 8.291E+05 | 621 | 0.27357 | 177 |
| 1.066E+06 | 621 | 0.27357 | 177 |
| 1.068E+06 | 621 | 0.27357 | 177 |
| 3.720E+06 | 621 | 0.27357 | 177 |
| 4.282E+06 | 621 | 0.27357 | 177 |
| 9.602E+06 | 621 | 0.27357 | 177 |
| 1.078E+07 | 621 | 0.27357 | 177 |
| 1.136E+07 | 621 | 0.27357 | 177 |
| 1.214E+07 | 621 | 0.27357 | 177 |
| 1.596E+05 | 690 | 0.30396 | 177 |
| 1.653E+05 | 690 | 0.30396 | 177 |
| 1.663E+05 | 690 | 0.30396 | 177 |
| 1.765E+05 | 690 | 0.30396 | 177 |
| 1.776E+05 | 690 | 0.30396 | 177 |
| 1.834E+05 | 690 | 0.30396 | 177 |
| 1.903E+05 | 690 | 0.30396 | 177 |
| 2.004E+05 | 690 | 0.30396 | 177 |
| 2.006E+05 | 690 | 0.30396 | 177 |
| 2.045E+05 | 690 | 0.30396 | 177 |
| 2.124E+05 | 690 | 0.30396 | 177 |
| 2.161E+05 | 690 | 0.30396 | 177 |
| 2.183E+05 | 690 | 0.30396 | 177 |
| 2.205E+05 | 690 | 0.30396 | 177 |
| 2.219E+05 | 690 | 0.30396 | 177 |
| 2.256E+05 | 690 | 0.30396 | 177 |
| 2.459E+05 | 690 | 0.30396 | 177 |
| 2.461E+05 | 690 | 0.30396 | 177 |
| 3.134E+05 | 690 | 0.30396 | 177 |
| 4.389E+05 | 690 | 0.30396 | 177 |
| 5.828E+04 | 931 | 0.41013 | 177 |
| 6.030E+04 | 931 | 0.41013 | 177 |
| 6.052E+04 | 931 | 0.41013 | 177 |
| 6.059E+04 | 931 | 0.41013 | 177 |
| 6.077E+04 | 931 | 0.41013 | 177 |
| 6.095E+04 | 931 | 0.41013 | 177 |
| 6.134E+04 | 931 | 0.41013 | 177 |
| 6.145E+04 | 931 | 0.41013 | 177 |
| 6.178E+04 | 931 | 0.41013 | 177 |
| 6.228E+04 | 931 | 0.41013 | 177 |
| 6.246E+04 | 931 | 0.41013 | 177 |
| 6.275E+04 | 931 | 0.41013 | 177 |
| 6.412E+04 | 931 | 0.41013 | 177 |
| 6.523E+04 | 931 | 0.41013 | 177 |
| 6.545E+04 | 931 | 0.41013 | 177 |
| 6.570E+04 | 931 | 0.41013 | 177 |
| 6.620E+04 | 931 | 0.41013 | 177 |
| 6.638E+04 | 931 | 0.41013 | 177 |
| 6.700E+04 | 931 | 0.41013 | 177 |
| 6.952E+04 | 931 | 0.41013 | 177 |
| 7.160E+04 | 931 | 0.41013 | 177 |
| 7.189E+04 | 931 | 0.41013 | 177 |
| 7.207E+04 | 931 | 0.41013 | 177 |
| 7.254E+04 | 931 | 0.41013 | 177 |
| 7.301E+04 | 931 | 0.41013 | 177 |
| 7.308E+04 | 931 | 0.41013 | 177 |
| 7.412E+04 | 931 | 0.41013 | 177 |
| 7.438E+04 | 931 | 0.41013 | 177 |
| 7.880E+04 | 931 | 0.41013 | 177 |
| 7.895E+04 | 931 | 0.41013 | 177 |

A wire made in accordance with a known process described in Altman (as described above) generated data points 56, shown as open square-shaped marks in FIG. 8 and tabulated below in Table 4E, also demonstrating failure at less than 600 MPa or 0.73 engineering strain.

TABLE 4E

Fatigue data from the Altman reference

| Lifetime (cycles) | Stress (Mpa) | Strain (mm/mm) | Wire Diameter (μm) |
|---|---|---|---|
| 3.040E+05 | 701 | 0.309 | 127 |
| 6.500E+04 | 825 | 0.363 | 127 |
| 1.420E+08 | 570 | 0.251 | 127 |
| 2.000E+04 | 1090 | 0.480 | 127 |
| 4.860E+06 | 496 | 0.219 | 127 |
| 7.100E+03 | 1650 | 0.727 | 127 |
| 8.210E+07 | 419 | 0.185 | 127 |
| 9.740E+07 | 348 | 0.153 | 127 |
| 4.590E+07 | 495 | 0.218 | 127 |
| 5.780E+07 | 416 | 0.183 | 127 |
| 2.200E+05 | 718 | 0.316 | 127 |
| 6.400E+05 | 569 | 0.251 | 127 |
| 4.200E+04 | 824 | 0.363 | 127 |

Thus, the fatigue threshold for wire made in accordance with the present process demonstrates a 20% to 100% improvement over conventional microcrystalline wire, as indicated above and shown in FIG. 8 and in Tables 4A-4E.

Tensile data and stress-strain curves for approximately 0.0046-in to 0.0059-in (0.12 mm to 0.15 mm) 35N LT® alloy wires manufactured as discussed above are shown in Table 5 below and in FIG. 11. Referring to Table 5, engineering strain to rupture is indicated as elongation ("Elong"), yield is represented as yield strength, and ultimate strength is represented as ultimate tensile. This data is also presented in FIGS. 17(*a*)-17(*c*) and discussed below.

TABLE 5

Results Table 1

| Spool No. | Diameter (in) | Breakload (lbf) | Ultimate Tensite (psi) | Elong (%) | Yield Load (lbf) | Yield Strength (psi) | Modulus (Mpsi) |
|---|---|---|---|---|---|---|---|
| 1 | 0.00465 | 3.487 | 205344 | 11.4 | 3.372 | 198576 | 22.6066 |
| 2 | 0.00465 | 3.486 | 205284 | 13.1 | 3.373 | 198625 | 23.0634 |
| 3 | 0.00502 | 3.964 | 200297 | 16.1 | 3.850 | 194517 | 22.8613 |
| 4 | 0.00502 | 3.967 | 200441 | 15.9 | 3.849 | 194458 | 22.8491 |
| 5 | 0.00537 | 4.695 | 207317 | 11.0 | 4.530 | 200010 | 21.7922 |
| 6 | 0.00537 | 4.692 | 207158 | 13.3 | 4.509 | 199065 | 23.1014 |
| 7 | 0.00589 | 5.617 | 206168 | 15.1 | 5.408 | 198477 | 23.4259 |
| 8 | 0.00589 | 5.612 | 205966 | 15.2 | 5.388 | 197758 | 24.4918 |
| Mean | 0.00523 | 4.440 | 204747 | 13.9 | 4.285 | 197686 | 23.0240 |
| Standard Deviation | 0.00049 | 0.85824 | 2800.94992 | 1.99657 | 0.81350 | 2072.79101 | 0.76270 |
| Mean + 3 SD | 0.00670 | 7.015 | 213150 | 19.9 | 6.725 | 203904 | 25.3121 |
| Mean − 3 SD | 0.00377 | 1.865 | 196344 | 7.9 | 1.844 | 191467 | 20.7359 |
| Minimum | 0.00465 | 3.486 | 200297 | 11.0 | 3.372 | 194458 | 21.7922 |
| Maximum | 0.00589 | 5.617 | 207317 | 16.1 | 5.408 | 200010 | 24.4918 |

Example 2

Structure-property Relationships in Conventional and Nanocrystalline Nitinol Intermetallic Alloy Wire In this example, homogeneous 177 μm diameter nanocrystalline Nitinol wires are produced and compared to microcrystalline Nitinol from equivalent ingot stock. Analysis of the physical properties of the wires was carried out using cyclic tension testing, strain-controlled fatigue testing, and bend and free recovery testing (BFR), as described below. Additionally, in order to observe the extremely fine structure, focused ion beam (FIB) milling was used to create thin-foil samples for transmission electron microscopy (TEM). The TEM micrographs confirmed a homogeneous B2 cubic structure of 5 to 60 nm grain size. Further, the constant life strain at $10^7$ cycles was found to be thirty percent greater in the nanocrystalline versus microcrystalline annealed wire. In addition, a positive correlation between grain size and irreversible plastic strain in cyclic uniaxial tension testing within the superelastic temperature and strain regime was identified.

1. Experimental Technique

In this example, approximately 2 mm Nitinol wire with an ingot $A_s$ of 243 K, comprising Ti-50.9 wt. % Ni was equivalently drawn and annealed to a diameter of 230 μm. At this stage, wires were continuously strand annealed at 650-850° C. at a sufficient dwell time to ensure complete recrystallization with a nominally 2 μm grain size. Samples were then conventionally wet-drawn using natural diamond drawing dies and oil-based lubricants to a finish diameter of 177 μm with nominally 40% retained cold work. Wire samples were finally continuously annealed at constant stress for less than 60 seconds to effect recrystallization while minimizing potential Ni-rich precipitation.

Near-surface microstructure and oxide thickness determination was performed using thin foil preparation and extraction by focused ion beam (FIB) and transmission electron microscopy (TEM). The preparation method is shown pictorially in FIGS. 22(*a*)-(*d*). The targeted sample surface is initially masked with a thin layer of vapor platinum compound deposit to protect the surface from ion implantation damage. Once masked, grain size distributions were calculated using digital image analysis as shown in FIGS. 10(*a*)-(*f*).

Active sample transformation temperatures were analyzed using bend and free recovery (BFR) methodology using a proprietary digital video analysis apparatus per standard ASTM F2082-06, Standard Test Method for Determination of Transformation Temperature of Nickel-Titanium Shape Memory Alloys by Bend and Free Recovery. Cyclic and monotonic uniaxial tensile properties were measured at an ambient temperature of 298 K at a strain rate of $10^{-3}$ s$^{-1}$ using an Instron Model 5565 Tensile Test Bench equipped with pneumatic grips. Fatigue behavior was characterized using rotary beam fatigue test equipment manufactured by Positool, Inc. at 3600 r/min in ambient 298 K air. Specimens from each grain size condition were tested at alternating strain levels ranging from 0.5 to 2.5% to a maximum of about $10^8$ cycles.

Figures 10A, 10B, 10C, 10D, 10E, 10F:
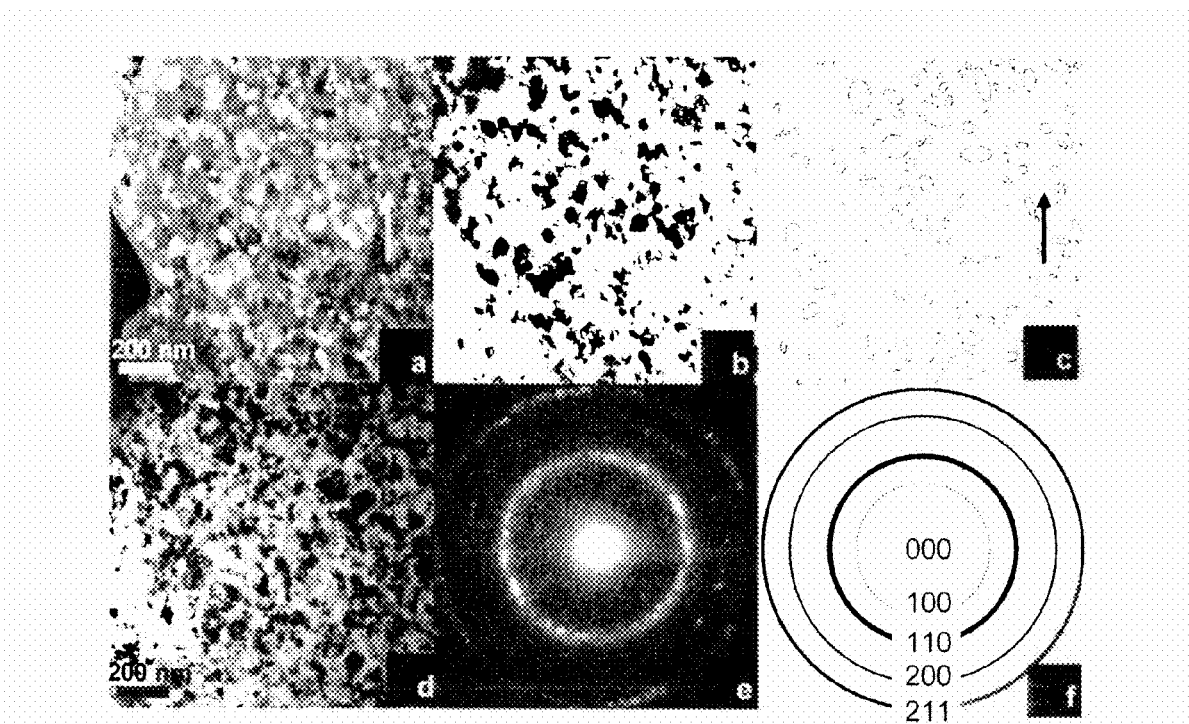
FIG. 10(a) depicts a dark field (DF) TEM image of a sample of Nitinol wire with a mean 50 nm grain size.
FIG. 10(b) depicts a binary conversion of the DF-TEM image of FIG. 10(a) for digital grain size analysis.
FIG. 10(c) depicts an ellipsoidal representation of analyzed grain field of FIG. 10(b) showing a lack of residual grain elongation in the drawing (arrow) direction.
FIG. 10(d) depicts a bright field (BF) TEM image of another sample with a mean 50 nm grain size equivalent material (different area)
FIG. 10(e) depicts a selected area diffraction pattern (SADP) of the area shown in FIG. 10(d) showing bright B2 cubic [110] polycrystalline ring.
FIG. 10(f) depicts the calculated powder DP for B2 Nitinol.

Various Nitinol wires were successfully produced at 177 μm diameter with each wire having different levels of grain nucleation and growth. Five distinct microstructures, having mean grain sizes of 50 nm, 100 nm, 2 μm, 5 μm, and 10 μm, were chosen for subsequent thermomechanical, mechanocyclic, and structural fatigue testing. Grain size distributions were calculated for each material using digital image analysis as shown in FIGS. 10(a)-(c). Selected area electron diffraction patterns were obtained in order to observe texture states and to look for evidence of precipitate reflections, an example of which is shown in FIGS. 10(d)-(f). Based on these patterns, no evidence of lenticular, Ni-rich precipitates has been found.

Figures 11A, 11B, 11C:
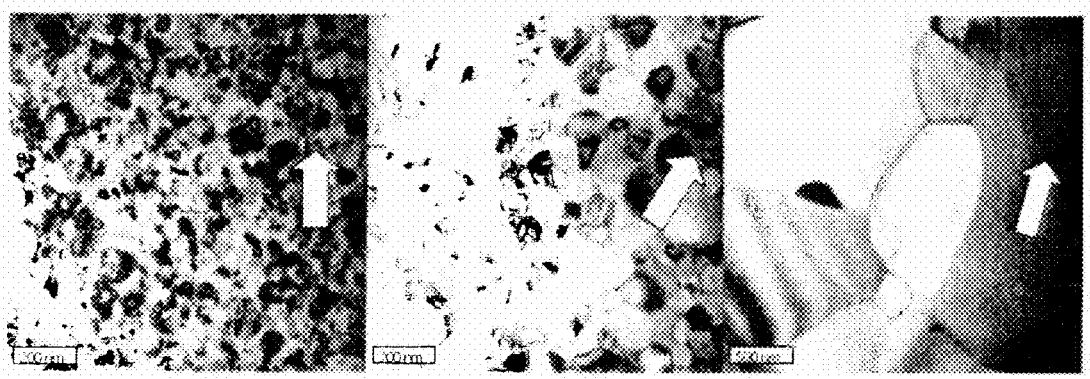
FIG. 11(a) depicts BF-TEM images showing an examined grain size of a Nitinol wire with a mean size of 50 nm, wherein the arrow indicates wire drawing direction.
FIG. 11(b) depicts BF-TEM images showing an examined grain size of a Nitinol wire with a mean size of 100 nm, wherein the arrow indicates wire drawing direction.
FIG. 11(c) depicts BF-TEM images showing an examined grain size of a Nitinol wire with a mean size of 2 μm, wherein the arrow indicates wire drawing direction.
Figure 12:
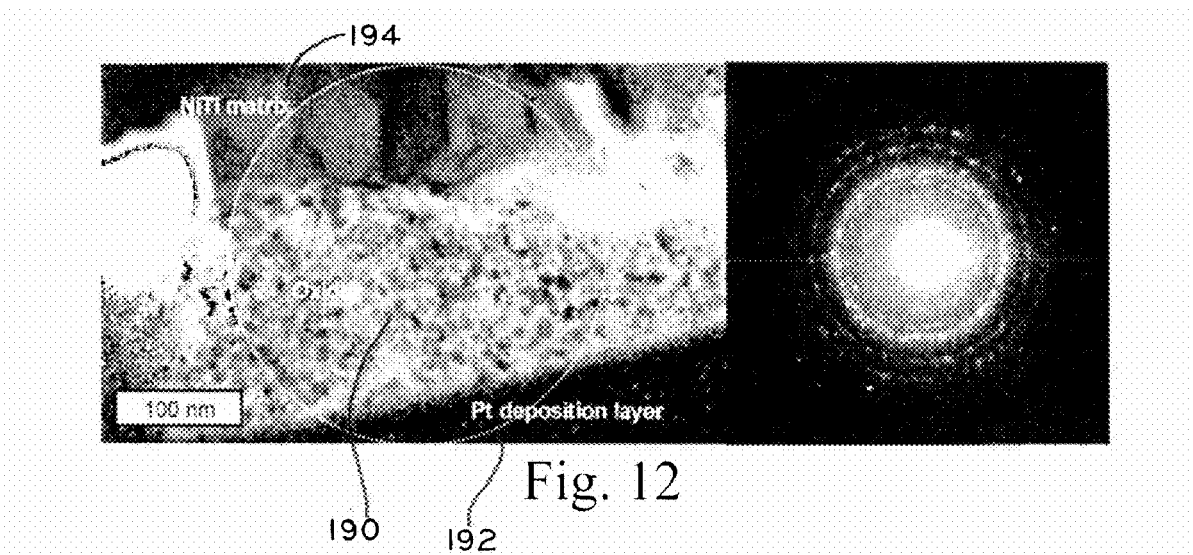
Figure 13:
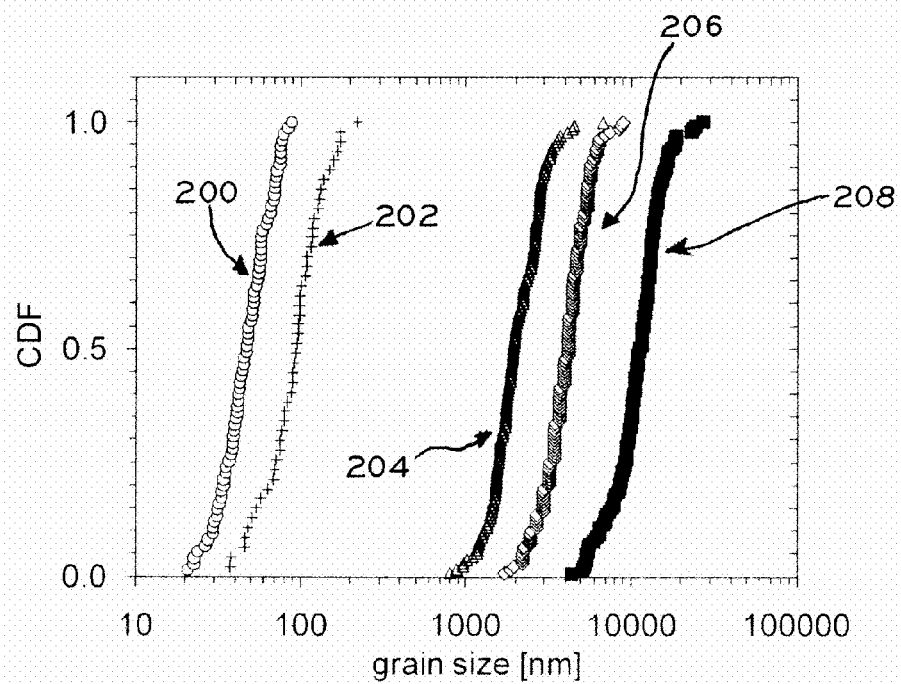

The nanocrystalline samples were confirmed to be homogeneous within the first 10 μm of material below the drawn oxide surface using TEM. Observed structures ranging from 50 nm to 2 μm are shown in FIGS. 11(a)-(c), with all samples found to possess equiaxed microstructure with little apparent signature from remnant cold work and the far right far image exhibiting dark fringes that are associated with Moire interference and tilt grain-boundary thickness fringes. Average oxide thickness for all samples was found to be about 120 nm, an example of which is given in FIG. 12 illustrating oxide layer 190 in the center of the circled portion, with platinum deposition layer 192 underneath oxide layer 190 and NiTi matrix 194 above oxide layer 190. Additionally, FIG. 13 provides the cumulative distribution function (CDF) representation of grain size distributions for grain sizes 50 nm (shown as data set 200), 100 nm (shown as data set 202), 2 μm (shown as data set 204), 5 μm (shown as data set 206), and 10 μm (shown as data set 208).

2. Results

Active transformation temperatures were measured for each of the samples using bend and recovery methods in accordance with ASTM standard F2082-6, Standard Test Method for Determination of Transformation Temperature of Nickel-Titanium Shape Memory Alloys by Bend and Free Recovery. All samples analyzed exhibited an $A_s$ temperature of 240±5 K, in good agreement with ingot DSC data. Plots of recovery data for each sample are given in FIG. 14, with small square-shaped marks 210 showing data for material with a grain size of 50 nm, X-shaped marks 212 showing data for material with a grain size of 100 nm, plus-shaped marks 214 showing data for material with a grain size of 2 μm, traingle-shaped marks 216 showing data for material with a grain size of 5 μm, and small square-shaped marks 218 showing data for material with a grain size of 10 μm. The samples that had an equiaxed grain size greater than 100 nm showed a clear single stage transformation associated with recovery from the martensitic to austenitic structure, and an active $A_f$ of 250±5 K. At the 50 nm grain size, the samples (represented by large square-shaped marks 210) showed some multistage recovery character as evidenced by at least one inflection point 210' near 260 K. The assumption of an entirely austenitic transformation placed calculations for the $A_f$ of the 50 nm samples at 277 to 279 K. It is postulated that the extended thermal recovery was due to a combination of high grain boundary energy content in the nanocrystalline material and matrix Ni loss due to slight Ni-rich precipitation, although the precipitates were not detected under TEM work to date.

Based on the examination of axial properties of the samples, the evolution of axial properties as a function of grain size followed a path expected from the classic Hall-Petch relationship: smaller grains resulted in increased strength and reduced plasticity during cyclic testing. For example, as shown in FIG. 15(c), single strain cycle testing to a reversal point of 4% strain showed a positive correlation between grain size and plastic deformation as measured by permanent set. The ultimate tensile strength measured in an axial monotonic test strongly increased with reduced grain size as shown in FIG. 15(d).

The initial onset of recoverable transformation strain and significant reversion stress at the 2 μm grain size was attributed to a reduction in the irreversible plastic behavior during stress-induced transformation. The finer, more plasticity resistant microstructures were not as susceptible to the stabilization of martensite by dislocation network formation.

A large increase in both ultimate strengths 222, 220 (as shown in FIG. 15(d)) and unloading plateau strengths 224, 226 (as shown in FIG. 15(a)) was found in the samples comprising 100 and 50 nm grain sizes respectively. Competing accommodation mechanisms have been found in martensitic Nitinol, with single variant B19' plates forming below about 80 nm and compound twinned variants forming in grains larger than about 100 nm. This type of threshold behavior may help explain constitutive behavior differences found in these samples.

The length of the stress-induced martensite load plateau was found to vary with the microstructural state. FIG. 15(b) shows typical superelastic plateau 230; the onset of elastic loading of the B19' matrix occurred at 7% strain. On the other hand, in the precipitate-free structure with a 100 nm equiaxed grain size, transformation plateau 232 terminated at 10.1% strain, with 9.6% strain recovery upon unloading.

As shown in FIG. 15(a), the unloading stiffness was found to decrease significantly from a nearly grain-size-invariant 42 GPa to 29 GPa at the 50 nm grain size. In this example, variability as a function of grain size was observed with step behavior between 50 and 100 nm. This behavior may be the result of energetic competition between single and compound martensite variants.

Figures 16A, 16B:
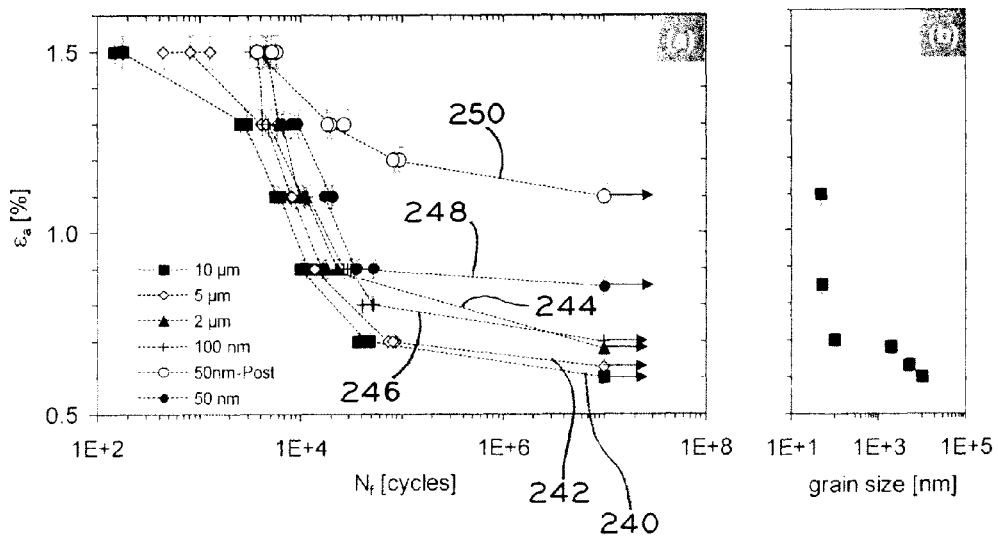

Rotary beam fatigue test results showed increased damage accumulation rates with increasing grain size. This was particularly evident at near-threshold conditions where lives were on the order of $10^5$ to $10^7$ cycles. For example, FIG. 16(a) shows strain-life curves each grain size of material tested. Lowermost curve 240, with square-shaped marks, shows data for a material size of 10 μm. Curve 242, with diamond-shaped marks, is for a 5 μm material. Curve 244, with triangle-shaped marks, is for a 2 μm material. Curve 246, with plus-shaped marks, is for a 100 nm material. Curve 248, with open circular marks, is for a 50 nm material after annealing. Uppermost curve 250, with filled circular marks, is for a 50 nm material before annealing.

The $10^7$ cycle data, shown in FIGS. 16(a) and 16(b), exemplified an ordered progression: curve 248, for wire with 50 nm mean grain size, demonstrated a resistance fatigue damage at the 0.9% alternating strain level, while curve 240, for 10 μm grain wire, demonstrated a resistance fatigue damage at the 0.6% level. Other structures, represented by curves 242, 244, 246 fell in order between these values.

Example 3

Shaped Wire Material In Accordance with the Compositional

Requirements of ASTM F562

Figure 17A:
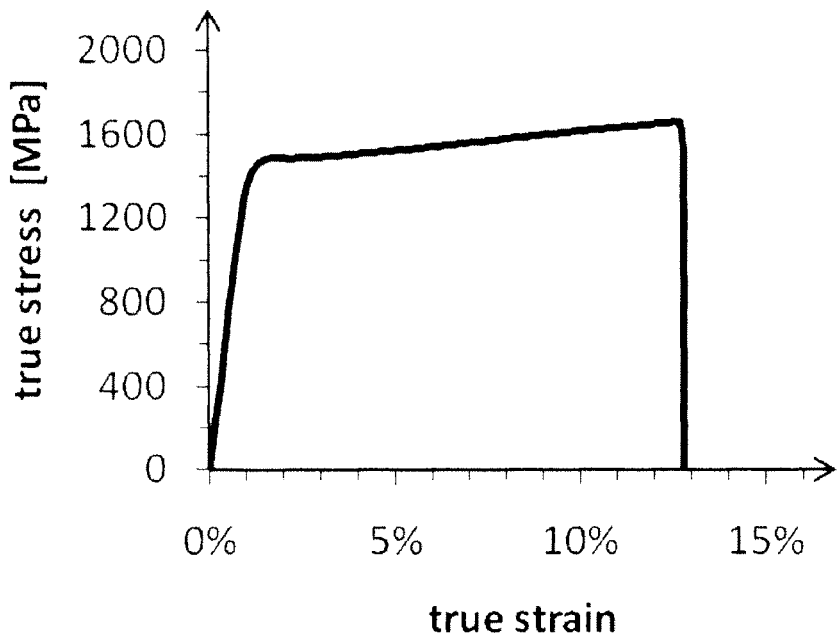
Figure 17B:
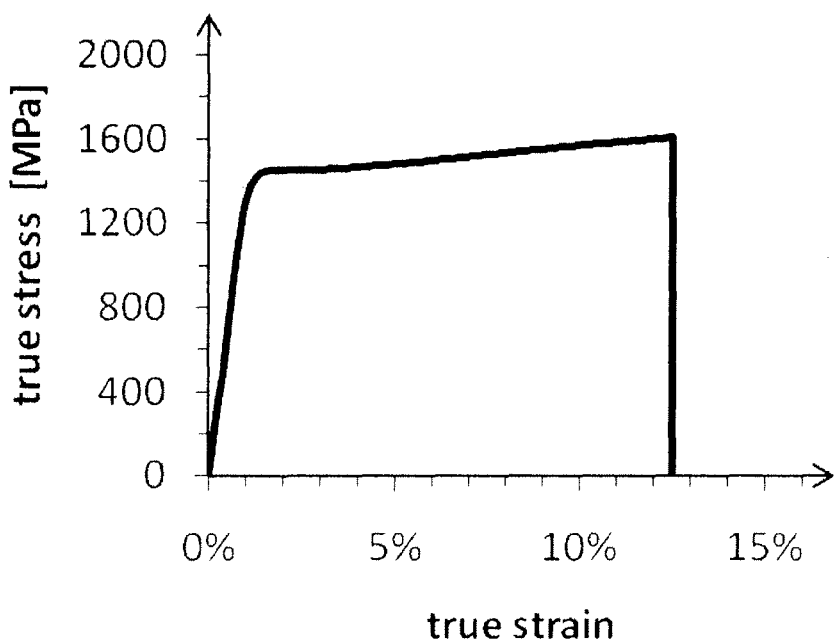
Figure 17C:
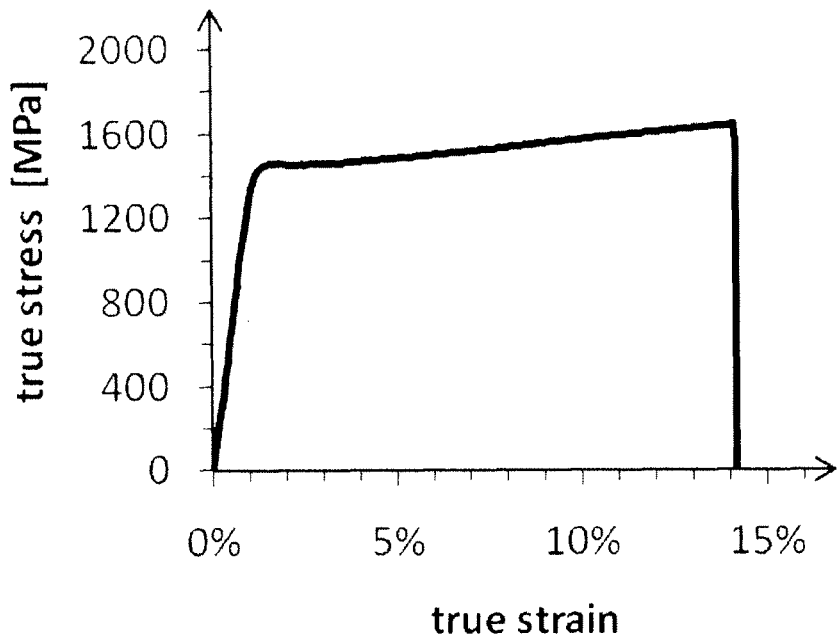

Referring to FIGS. 17(a)-17(c) and Tables 6-8m, and 19 below, in this Example 25N LT flat shaped wire with a thickness, defined as the minor transverse dimension, of 0.0050-in (0.127 mm) and a width, defined as the transverse dimension orthogonal to the minor dimension, of 0.0090-in (0.229 mm) was produced and tested. The materials exhibited wire properties and characteristics in accordance with an embodiment of the present process.

1. Experimental Technique

The process started with a VIM (vacuum induction melted)/VAR (vacuum arc remelted) 35N LT® ingot that was processed by hot rolling into rod stock. The material was then iteratively cold worked and annealed in a conventional manner to a diameter of 1.6 mm. A conventional anneal step at 1.6 mm was followed by cold drawing the material through round diamond dies to 0.91 mm. Then, the material was conventionally annealed to produce an equiaxed grain structure with a mean grain size of about 1 to 5 μm.

With respect to the cold work conditioning and nano-recrystallization steps of the present process, it has been found that preparation of 35N LT® alloy for nano-recrystallization entails a relatively high amount of deformation in the cold work conditioning step as detailed below.

In the present example, the annealed wires having diameter 0.91 mm wire was subjected to a cold work conditioning step by drawing to a diameter of 0.0074-in (0.19 mm) in preparation for nanorecrystallization. According to Formula I above, the cold work conditioning steps therefore imparted nominally 96% cold work to the material. The nano-recrystallization step was performed at 850° C. at a dwell time of about 2-3 seconds. The resultant nanograin crystal structure was qualitatively confirmed by mechanical testing, specifically tensile testing, the results of which are shown in FIG. 17(c). Specifically, the material was observed to possess similar levels of strength, ductility and yield properties previously discussed and in accordance with the present process.

TABLE 6

True strain and true stress, 35N LT ® alloy wire, dia. 0.007-in (0.18 mm) - FIG. 17(a)

| True strain (in/in) | True stress (ksi) | True stress (MPa) |
|---|---|---|
| 0.000 | 0.0 | 0.0 |
| 0.001 | 19.2 | 132.1 |
| 0.002 | 34.2 | 235.6 |
| 0.003 | 49.1 | 338.5 |
| 0.003 | 63.9 | 440.3 |
| 0.004 | 78.6 | 542.2 |
| 0.005 | 93.6 | 645.5 |
| 0.005 | 108.8 | 749.8 |
| 0.006 | 123.9 | 854.3 |
| 0.007 | 138.9 | 957.7 |
| 0.007 | 154.0 | 1061.7 |
| 0.008 | 169.1 | 1165.8 |
| 0.009 | 184.2 | 1269.7 |
| 0.010 | 197.7 | 1363.2 |
| 0.012 | 205.9 | 1419.4 |
| 0.013 | 210.5 | 1451.7 |
| 0.014 | 213.3 | 1470.4 |
| 0.015 | 214.7 | 1480.2 |
| 0.017 | 215.3 | 1484.6 |
| 0.018 | 215.5 | 1485.7 |
| 0.019 | 215.4 | 1484.8 |
| 0.020 | 215.2 | 1483.8 |
| 0.021 | 215.1 | 1483.3 |
| 0.023 | 215.2 | 1483.5 |
| 0.024 | 215.3 | 1484.2 |
| 0.025 | 215.4 | 1485.3 |
| 0.026 | 215.6 | 1486.3 |
| 0.028 | 215.8 | 1487.8 |
| 0.029 | 216.0 | 1489.0 |
| 0.030 | 216.2 | 1490.6 |
| 0.031 | 216.4 | 1492.0 |
| 0.032 | 216.7 | 1493.8 |
| 0.034 | 216.9 | 1495.3 |
| 0.035 | 217.1 | 1497.2 |
| 0.036 | 217.4 | 1498.8 |
| 0.037 | 217.7 | 1500.7 |
| 0.038 | 217.9 | 1502.4 |
| 0.040 | 218.2 | 1504.3 |
| 0.041 | 218.4 | 1506.0 |
| 0.042 | 218.7 | 1508.0 |
| 0.043 | 219.0 | 1509.9 |
| 0.044 | 219.3 | 1511.7 |
| 0.046 | 219.5 | 1513.6 |
| 0.047 | 219.8 | 1515.6 |
| 0.048 | 220.1 | 1517.5 |
| 0.049 | 220.4 | 1519.4 |
| 0.050 | 220.7 | 1521.5 |
| 0.052 | 220.9 | 1523.3 |
| 0.053 | 221.2 | 1525.4 |
| 0.054 | 221.5 | 1527.3 |
| 0.055 | 221.8 | 1529.4 |
| 0.056 | 222.1 | 1531.3 |
| 0.058 | 222.4 | 1533.5 |
| 0.059 | 222.7 | 1535.5 |
| 0.060 | 223.0 | 1537.7 |
| 0.061 | 223.3 | 1539.6 |
| 0.062 | 223.6 | 1541.8 |
| 0.063 | 223.9 | 1543.8 |
| 0.065 | 224.2 | 1546.1 |
| 0.066 | 224.5 | 1548.2 |
| 0.067 | 224.9 | 1550.4 |
| 0.068 | 225.2 | 1552.7 |
| 0.069 | 225.5 | 1554.8 |
| 0.070 | 225.8 | 1557.1 |
| 0.072 | 226.1 | 1559.2 |
| 0.073 | 226.5 | 1561.5 |
| 0.074 | 226.8 | 1563.7 |
| 0.075 | 227.1 | 1566.0 |
| 0.076 | 227.4 | 1568.1 |
| 0.077 | 227.8 | 1570.6 |
| 0.079 | 228.1 | 1572.5 |
| 0.080 | 228.4 | 1575.0 |
| 0.081 | 228.7 | 1577.1 |
| 0.082 | 229.1 | 1579.5 |
| 0.083 | 229.4 | 1581.5 |
| 0.084 | 229.7 | 1583.8 |
| 0.085 | 230.0 | 1585.9 |
| 0.087 | 230.3 | 1588.0 |
| 0.088 | 230.6 | 1590.1 |
| 0.089 | 230.9 | 1592.3 |
| 0.090 | 231.2 | 1594.3 |
| 0.091 | 231.6 | 1596.6 |
| 0.092 | 231.8 | 1598.5 |
| 0.094 | 232.2 | 1600.6 |
| 0.095 | 232.5 | 1602.7 |
| 0.096 | 232.7 | 1604.6 |
| 0.097 | 233.0 | 1606.7 |
| 0.098 | 233.3 | 1608.6 |
| 0.099 | 233.6 | 1610.6 |
| 0.100 | 233.9 | 1612.6 |
| 0.101 | 234.2 | 1614.6 |
| 0.103 | 234.5 | 1616.5 |
| 0.104 | 234.8 | 1618.7 |
| 0.105 | 235.0 | 1620.3 |
| 0.106 | 235.3 | 1622.4 |
| 0.107 | 235.6 | 1624.2 |
| 0.108 | 235.9 | 1626.2 |
| 0.109 | 236.1 | 1628.0 |
| 0.110 | 236.4 | 1629.9 |
| 0.112 | 236.7 | 1631.7 |
| 0.113 | 236.9 | 1633.7 |
| 0.114 | 237.2 | 1635.4 |
| 0.115 | 237.5 | 1637.2 |
| 0.116 | 237.7 | 1639.1 |
| 0.117 | 238.0 | 1640.8 |
| 0.118 | 238.2 | 1642.6 |
| 0.119 | 238.5 | 1644.3 |
| 0.120 | 238.7 | 1646.1 |
| 0.122 | 239.0 | 1647.7 |
| 0.123 | 239.2 | 1649.4 |

TABLE 6-continued

True strain and true stress, 35N LT ® alloy wire,
dia. 0.007-in (0.18 mm) - FIG. 17(a)

| True strain (in/in) | True stress (ksi) | True stress (MPa) |
|---|---|---|
| 0.124 | 239.5 | 1651.0 |
| 0.125 | 239.7 | 1652.7 |
| 0.126 | 239.9 | 1653.9 |
| 0.127 | 240.1 | 1655.2 |
| 0.128 | 219.2 | 1511.4 |
| 0.128 | 195.3 | 1346.5 |
| 0.128 | 0.0 | 0.0 |

TABLE 7

True strain and true stress, 35N LT ® alloy wire,
dia. 0.0042-in (0.107 mm) - FIG. 17(b)

| True strain (in/in) | True stress (ksi) | True stress (MPa) |
|---|---|---|
| 0.000 | 0.0 | 0.0 |
| 0.003 | 50.9 | 350.6 |
| 0.004 | 70.6 | 486.5 |
| 0.005 | 99.7 | 687.4 |
| 0.006 | 127.7 | 880.1 |
| 0.008 | 153.3 | 1057.2 |
| 0.009 | 175.3 | 1208.6 |
| 0.010 | 190.8 | 1315.4 |
| 0.011 | 199.8 | 1377.5 |
| 0.012 | 205.1 | 1414.2 |
| 0.014 | 208.2 | 1435.4 |
| 0.015 | 209.8 | 1446.4 |
| 0.016 | 210.5 | 1451.6 |
| 0.017 | 210.8 | 1453.1 |
| 0.019 | 210.7 | 1453.0 |
| 0.020 | 210.6 | 1451.7 |
| 0.021 | 210.4 | 1450.7 |
| 0.022 | 210.2 | 1449.3 |
| 0.024 | 210.1 | 1448.8 |
| 0.025 | 210.1 | 1448.5 |
| 0.026 | 210.2 | 1449.0 |
| 0.027 | 210.2 | 1449.4 |
| 0.028 | 210.4 | 1450.7 |
| 0.030 | 210.6 | 1451.7 |
| 0.031 | 210.7 | 1452.9 |
| 0.032 | 211.0 | 1454.5 |
| 0.033 | 211.2 | 1455.9 |
| 0.035 | 211.4 | 1457.3 |
| 0.036 | 211.6 | 1458.9 |
| 0.037 | 211.8 | 1460.5 |
| 0.038 | 212.1 | 1462.0 |
| 0.039 | 212.3 | 1463.7 |
| 0.041 | 212.5 | 1465.3 |
| 0.042 | 212.8 | 1467.1 |
| 0.043 | 213.0 | 1468.6 |
| 0.044 | 213.3 | 1470.5 |
| 0.045 | 213.5 | 1471.9 |
| 0.047 | 213.8 | 1473.9 |
| 0.048 | 214.0 | 1475.6 |
| 0.049 | 214.3 | 1477.6 |
| 0.050 | 214.6 | 1479.3 |
| 0.051 | 214.9 | 1481.5 |
| 0.053 | 215.1 | 1483.1 |
| 0.054 | 215.4 | 1485.1 |
| 0.055 | 215.7 | 1487.0 |
| 0.056 | 216.0 | 1489.0 |
| 0.057 | 216.2 | 1490.9 |
| 0.058 | 216.5 | 1493.0 |
| 0.060 | 216.8 | 1495.1 |
| 0.061 | 217.1 | 1497.0 |
| 0.062 | 217.4 | 1499.2 |
| 0.063 | 217.7 | 1501.2 |
| 0.064 | 218.0 | 1503.2 |

TABLE 7-continued

True strain and true stress, 35N LT ® alloy wire,
dia. 0.0042-in (0.107 mm) - FIG. 17(b)

| True strain (in/in) | True stress (ksi) | True stress (MPa) |
|---|---|---|
| 0.066 | 218.3 | 1505.4 |
| 0.067 | 218.6 | 1507.4 |
| 0.068 | 218.9 | 1509.6 |
| 0.069 | 219.3 | 1511.9 |
| 0.070 | 219.6 | 1514.0 |
| 0.071 | 219.9 | 1516.2 |
| 0.073 | 220.2 | 1518.3 |
| 0.074 | 220.5 | 1520.6 |
| 0.075 | 220.8 | 1522.4 |
| 0.076 | 221.1 | 1524.7 |
| 0.077 | 221.4 | 1526.5 |
| 0.078 | 221.7 | 1528.8 |
| 0.080 | 222.0 | 1530.6 |
| 0.081 | 222.3 | 1532.9 |
| 0.082 | 222.6 | 1534.8 |
| 0.083 | 222.9 | 1536.8 |
| 0.084 | 223.2 | 1539.0 |
| 0.085 | 223.5 | 1541.0 |
| 0.086 | 223.8 | 1543.1 |
| 0.088 | 224.1 | 1545.2 |
| 0.089 | 224.4 | 1547.1 |
| 0.090 | 224.7 | 1549.1 |
| 0.091 | 225.0 | 1551.4 |
| 0.092 | 225.3 | 1553.1 |
| 0.093 | 225.6 | 1555.2 |
| 0.094 | 225.8 | 1557.0 |
| 0.096 | 226.1 | 1558.8 |
| 0.097 | 226.4 | 1560.9 |
| 0.098 | 226.7 | 1562.8 |
| 0.099 | 226.9 | 1564.4 |
| 0.100 | 227.2 | 1566.3 |
| 0.101 | 227.4 | 1568.0 |
| 0.102 | 227.7 | 1569.8 |
| 0.104 | 227.9 | 1571.5 |
| 0.105 | 228.2 | 1573.3 |
| 0.106 | 228.4 | 1575.0 |
| 0.107 | 228.7 | 1576.9 |
| 0.108 | 229.0 | 1578.6 |
| 0.109 | 229.2 | 1580.5 |
| 0.110 | 229.5 | 1582.3 |
| 0.111 | 229.8 | 1584.2 |
| 0.113 | 230.0 | 1585.9 |
| 0.114 | 230.3 | 1587.7 |
| 0.115 | 230.5 | 1589.5 |
| 0.116 | 230.7 | 1590.9 |
| 0.117 | 231.0 | 1592.8 |
| 0.118 | 231.2 | 1594.2 |
| 0.119 | 231.5 | 1595.9 |
| 0.120 | 231.7 | 1597.4 |
| 0.121 | 231.9 | 1599.1 |
| 0.123 | 232.1 | 1600.4 |
| 0.124 | 232.4 | 1602.1 |
| 0.125 | 232.4 | 1602.6 |
| 0.125 | 181.1 | 1248.8 |
| 0.125 | 0.0 | 0.0 |

TABLE 8

True strain and true stress, 35N LT ® alloy ribbon,
0.005-in (0.127 mm) × 0.009-in (0.229 mm) - FIG. 17(c)

| True strain (in/in) | True stress (ksi) | True stress (MPa) |
|---|---|---|
| 0.000 | 0.0 | 0.0 |
| 0.001 | 12.2 | 84.0 |
| 0.001 | 25.1 | 173.0 |
| 0.002 | 38.0 | 262.1 |
| 0.003 | 51.1 | 352.1 |

TABLE 8-continued

True strain and true stress, 35N LT ® alloy ribbon,
0.005-in (0.127 mm) × 0.009-in (0.229 mm) - FIG. 17(c)

| True strain (in/in) | True stress (ksi) | True stress (MPa) |
|---|---|---|
| 0.003 | 64.1 | 442.1 |
| 0.004 | 77.1 | 531.3 |
| 0.005 | 90.0 | 620.6 |
| 0.005 | 103.0 | 709.9 |
| 0.006 | 115.8 | 798.5 |
| 0.007 | 128.9 | 888.7 |
| 0.007 | 141.8 | 977.9 |
| 0.008 | 155.0 | 1068.7 |
| 0.009 | 168.0 | 1158.0 |
| 0.009 | 181.1 | 1248.7 |
| 0.010 | 194.2 | 1339.0 |
| 0.012 | 203.9 | 1405.5 |
| 0.013 | 208.5 | 1437.2 |
| 0.014 | 210.6 | 1452.0 |
| 0.015 | 211.5 | 1458.2 |
| 0.017 | 211.8 | 1460.0 |
| 0.018 | 211.7 | 1459.5 |
| 0.019 | 211.4 | 1457.7 |
| 0.020 | 210.9 | 1454.0 |
| 0.022 | 210.8 | 1453.4 |
| 0.023 | 210.9 | 1454.3 |
| 0.024 | 211.0 | 1454.5 |
| 0.025 | 210.9 | 1454.1 |
| 0.026 | 211.0 | 1454.6 |
| 0.028 | 211.0 | 1454.8 |
| 0.029 | 211.1 | 1455.5 |
| 0.030 | 211.2 | 1456.4 |
| 0.031 | 211.4 | 1457.5 |
| 0.032 | 211.6 | 1458.7 |
| 0.034 | 211.8 | 1460.3 |
| 0.035 | 212.0 | 1461.4 |
| 0.036 | 212.2 | 1463.1 |
| 0.037 | 212.4 | 1464.5 |
| 0.039 | 212.6 | 1466.1 |
| 0.040 | 212.9 | 1467.7 |
| 0.041 | 213.1 | 1469.5 |
| 0.042 | 213.4 | 1471.2 |
| 0.043 | 213.6 | 1472.9 |
| 0.045 | 213.9 | 1474.7 |
| 0.046 | 214.2 | 1476.6 |
| 0.047 | 214.4 | 1478.4 |
| 0.048 | 214.7 | 1480.2 |
| 0.049 | 215.0 | 1482.1 |
| 0.050 | 215.2 | 1483.8 |
| 0.052 | 215.5 | 1485.8 |
| 0.053 | 215.7 | 1487.4 |
| 0.054 | 216.0 | 1489.4 |
| 0.055 | 216.3 | 1491.2 |
| 0.056 | 216.6 | 1493.2 |
| 0.058 | 216.8 | 1494.7 |
| 0.059 | 217.1 | 1496.9 |
| 0.060 | 217.4 | 1498.6 |
| 0.061 | 217.6 | 1500.6 |
| 0.062 | 217.9 | 1502.4 |
| 0.063 | 218.2 | 1504.4 |
| 0.065 | 218.5 | 1506.3 |
| 0.066 | 218.8 | 1508.2 |
| 0.067 | 219.0 | 1510.2 |
| 0.068 | 219.3 | 1512.2 |
| 0.069 | 219.6 | 1514.2 |
| 0.070 | 219.9 | 1516.3 |
| 0.072 | 220.2 | 1518.4 |
| 0.073 | 220.5 | 1520.4 |
| 0.074 | 220.8 | 1522.6 |
| 0.075 | 221.1 | 1524.7 |
| 0.076 | 221.5 | 1527.0 |
| 0.077 | 221.8 | 1529.1 |
| 0.079 | 222.1 | 1531.7 |
| 0.080 | 222.5 | 1533.8 |
| 0.081 | 222.8 | 1536.4 |
| 0.082 | 223.2 | 1538.7 |
| 0.083 | 223.5 | 1541.2 |
| 0.084 | 223.9 | 1543.4 |
| 0.086 | 224.2 | 1546.0 |
| 0.087 | 224.5 | 1548.1 |
| 0.088 | 224.9 | 1550.5 |
| 0.089 | 225.2 | 1552.6 |
| 0.090 | 225.5 | 1554.8 |
| 0.091 | 225.8 | 1556.9 |
| 0.092 | 226.1 | 1559.0 |
| 0.094 | 226.4 | 1561.2 |
| 0.095 | 226.7 | 1563.3 |
| 0.096 | 227.0 | 1565.3 |
| 0.097 | 227.3 | 1567.3 |
| 0.098 | 227.6 | 1569.4 |
| 0.099 | 227.9 | 1571.3 |
| 0.100 | 228.2 | 1573.4 |
| 0.101 | 228.5 | 1575.2 |
| 0.103 | 228.8 | 1577.3 |
| 0.104 | 229.1 | 1579.3 |
| 0.105 | 229.3 | 1581.3 |
| 0.106 | 229.6 | 1583.1 |
| 0.107 | 229.9 | 1585.2 |
| 0.108 | 230.2 | 1587.0 |
| 0.109 | 230.5 | 1589.1 |
| 0.110 | 230.7 | 1590.8 |
| 0.112 | 231.0 | 1592.8 |
| 0.113 | 231.3 | 1594.8 |
| 0.114 | 231.6 | 1596.6 |
| 0.115 | 231.8 | 1598.5 |
| 0.116 | 232.1 | 1600.5 |
| 0.117 | 232.4 | 1602.4 |
| 0.118 | 232.7 | 1604.2 |
| 0.119 | 233.0 | 1606.1 |
| 0.121 | 233.2 | 1607.9 |
| 0.122 | 233.5 | 1609.8 |
| 0.123 | 233.7 | 1611.3 |
| 0.124 | 234.0 | 1613.2 |
| 0.125 | 234.2 | 1614.9 |
| 0.126 | 234.5 | 1616.7 |
| 0.127 | 234.7 | 1618.3 |
| 0.128 | 235.0 | 1620.1 |
| 0.129 | 235.2 | 1621.8 |
| 0.130 | 235.5 | 1623.6 |
| 0.132 | 235.7 | 1625.0 |
| 0.133 | 236.0 | 1626.9 |
| 0.134 | 236.2 | 1628.5 |
| 0.135 | 236.4 | 1630.2 |
| 0.136 | 236.7 | 1631.7 |
| 0.137 | 236.9 | 1633.5 |
| 0.138 | 237.1 | 1635.0 |
| 0.139 | 237.4 | 1636.5 |
| 0.140 | 237.5 | 1637.8 |
| 0.141 | 237.6 | 1638.0 |
| 0.142 | 221.0 | 1524.0 |
| 0.142 | 198.6 | 1369.2 |
| 0.142 | 171.4 | 1181.9 |
| 0.142 | 0.0 | 0.0 |

Example 4

ASTM F562 Materials with Additional Cold Work

Figure 18A:
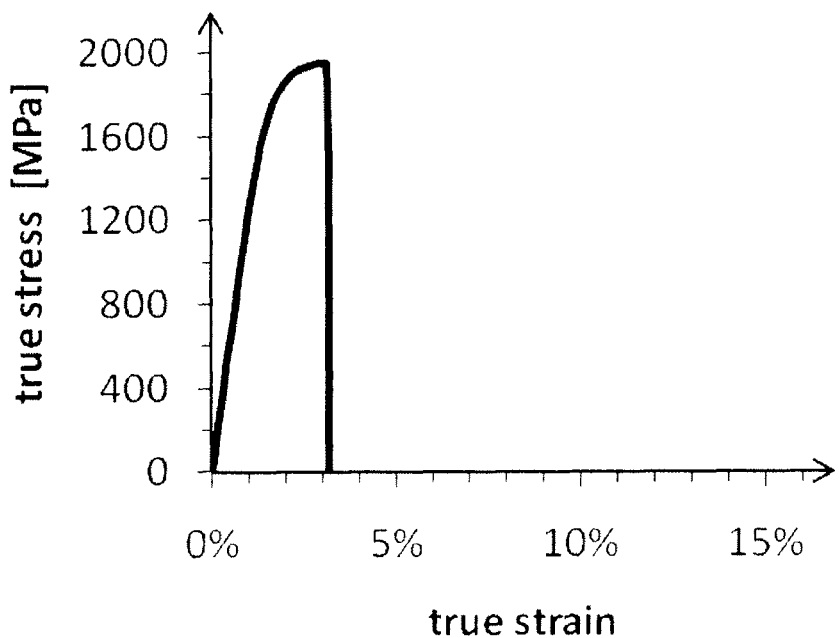
Figure 18B:
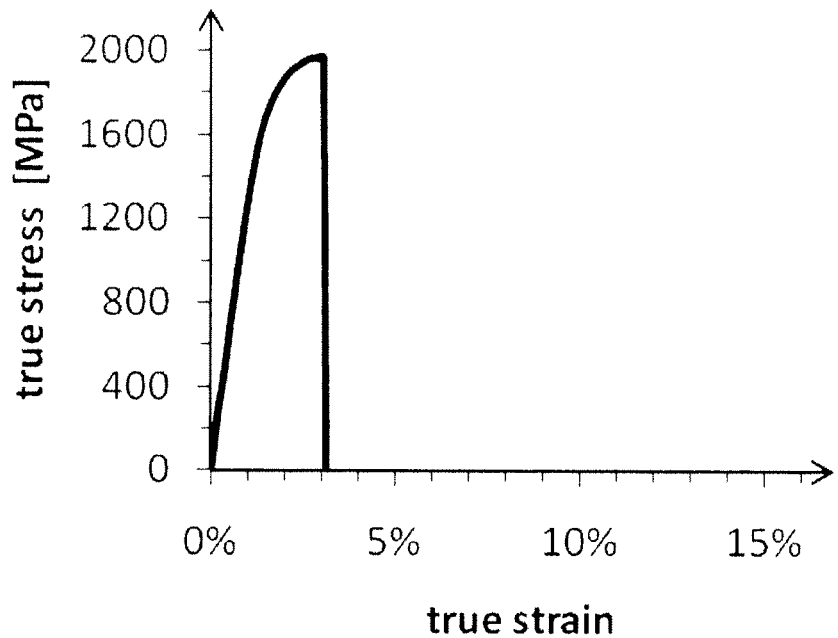

Referring to FIGS. 18(a)-18(b) and Tables 9-10, and 19 below, in this Example 25N LT round wires with diameters of 0.0030-in (76 μm) and 0.0035-in (0.089 mm) were produced and tested. The wires exhibited properties and characteristics in accordance with an embodiment of the present process.

1. Experimental Technique

The process started with a VIM (vacuum induction melted)/VAR (vacuum arc remelted) 35N LT® ingot that was processed by hot rolling into rod stock. The material was then iteratively cold worked and annealed in a conventional manner to a diameter of 1.6 mm. A conventional anneal step at 1.6 mm was followed by cold drawing the material through round diamond dies to 0.91 mm. Then, the material was conventionally annealed to produce an equiaxed grain structure with a mean grain size of about 1 to 5 μm and drawn conventionally to diameters of 0.45 mm and 0.51 mm for the 0.076 and 0.089 mm wires respectively.

With respect to the cold work conditioning and nano-recrystallization steps of the present process, it has been found that preparation of 35N LT® alloy for nano-recrystallization entails a relatively high amount of deformation in the cold work conditioning step as described below.

In the present example, the annealed wires having diameters of 0.45 mm and 0.51 mm were subjected to a cold work conditioning step by drawing to a diameter of 0.096 mm and 0.107 mm respectively in preparation for nanorecrystallization. According to Formula I above, the cold work conditioning steps therefore imparted nominally 95% cold work to the material.

The nano-recrystallization step was performed at 850° C. at a dwell time of about 2-3 seconds. The resultant nanograin crystal structure was qualitatively confirmed by mechanical testing, specifically tensile testing the 0.096 mm and 0.107 mm wires, the results of which were similar in terms of strength, ductility and yield properties previously discussed and in accordance with the present process.

In order to increase the strength level of the material, the 0.096 mm and 0.107 mm wires were subsequently drawn by conventional means to diameters of 0.076 mm and 0.089 mm and tensile tested in order to gage the strength and ductility.

2. Results

The results of tensile testing of these wires are presented in FIGS. 18(*a*) and (*b*) for the 0.076 mm and 0.089 mm materials respectively, the raw data from which are given in Table 9 and summarized in Table 3.

The resultant data from rotary beam fatigue testing of the 0.076 mm wire are presented in FIG. 20 and are represented by the black X's. The observed endurance limit, as determined by rotary beam fatigue testing, of the material at $10^8$ cycles exceeded a strain amplitude of 0.60% (Table 2).

TABLE 9

True strain and true stress, 35N LT ® alloy wire with additional cold work, dia. 0.0035-in (0.089 mm) - FIG. 18(a)

| True strain (in/in) | True stress (ksi) | True stress (MPa) |
|---|---|---|
| 0.000 | 0.0 | 0.0 |
| 0.003 | 55.9 | 385.5 |
| 0.004 | 73.9 | 509.2 |
| 0.005 | 99.7 | 687.6 |
| 0.007 | 123.8 | 853.5 |
| 0.008 | 146.4 | 1009.6 |
| 0.009 | 167.9 | 1157.7 |
| 0.010 | 188.0 | 1296.5 |
| 0.012 | 206.5 | 1424.1 |
| 0.013 | 222.8 | 1536.4 |
| 0.014 | 236.1 | 1627.8 |
| 0.015 | 246.2 | 1697.1 |
| 0.016 | 254.0 | 1751.1 |
| 0.018 | 260.4 | 1795.5 |
| 0.019 | 265.8 | 1832.7 |
| 0.020 | 270.2 | 1862.6 |
| 0.021 | 273.7 | 1886.9 |
| 0.023 | 276.4 | 1905.7 |
| 0.024 | 278.4 | 1919.7 |
| 0.025 | 279.9 | 1929.7 |

TABLE 9-continued

True strain and true stress, 35N LT ® alloy wire with additional cold work, dia. 0.0035-in (0.089 mm) - FIG. 18(a)

| True strain (in/in) | True stress (ksi) | True stress (MPa) |
|---|---|---|
| 0.026 | 281.0 | 1937.1 |
| 0.027 | 281.7 | 1941.9 |
| 0.029 | 282.2 | 1945.5 |
| 0.030 | 282.5 | 1947.8 |
| 0.031 | 282.7 | 1949.2 |
| 0.032 | 217.4 | 1499.0 |
| 0.032 | 0.0 | 0.0 |

TABLE 10

True strain and true stress, 35N LT ® alloy wire with additional cold work, dia. 0.003-in (0.076 mm) - FIG. 18(b)

| True strain (in/in) | True stress (ksi) | True stress (MPa) |
|---|---|---|
| 0.000 | 0.0 | 0.0 |
| 0.002 | 45.5 | 314.0 |
| 0.003 | 63.7 | 439.3 |
| 0.005 | 90.2 | 621.8 |
| 0.006 | 114.9 | 792.5 |
| 0.007 | 138.2 | 952.9 |
| 0.009 | 160.3 | 1105.3 |
| 0.010 | 181.2 | 1249.6 |
| 0.011 | 200.6 | 1383.3 |
| 0.012 | 217.9 | 1502.2 |
| 0.013 | 232.3 | 1601.8 |
| 0.015 | 243.5 | 1678.6 |
| 0.016 | 252.1 | 1737.9 |
| 0.017 | 258.9 | 1785.4 |
| 0.018 | 264.8 | 1825.9 |
| 0.020 | 269.7 | 1859.6 |
| 0.021 | 273.9 | 1888.3 |
| 0.022 | 277.1 | 1910.7 |
| 0.023 | 279.8 | 1928.8 |
| 0.025 | 281.8 | 1942.8 |
| 0.026 | 283.3 | 1953.2 |
| 0.027 | 284.3 | 1960.3 |
| 0.028 | 285.1 | 1965.6 |
| 0.029 | 285.6 | 1969.0 |
| 0.031 | 285.8 | 1970.8 |
| 0.031 | 0.0 | 0.0 |

Example 5

304L Stainless Steel

Referring to FIGS. 19(*a*)-19(*c*) and Tables 11-13, and 19 below, in this Example 204L round wire with a diameter of 0.0070-in (0.18 mm) was produced and tested. The wires exhibited wire properties and characteristics in accordance with an embodiment of the present process.

1. Experimental Technique

The process started with a VIM (vacuum induction melted) 304L ingot that was processed by hot rolling into rod stock. The material was then iteratively cold worked and annealed in a conventional manner to a diameter of 2.4 mm to yield an equiaxed grain structure with a mean grain size of about 10 to 20 μm.

With respect to the cold work conditioning and nano-recrystallization steps of the present process, it has been found that preparation of 304L alloy for nano-recrystallization entails a relatively high amount of deformation in the cold work conditioning step as described below.

In the present example, the annealed wires having diameter 2.4 mm were subjected to a cold work conditioning step by drawing to a diameter of 0.18 mm in preparation for nano-recrystallization. According to Formula I above, the cold work conditioning steps therefore imparted nominally 99.5% cold work (5.22 units true strain according to Formula II above) to the material.

2. Results

Figure 23B:
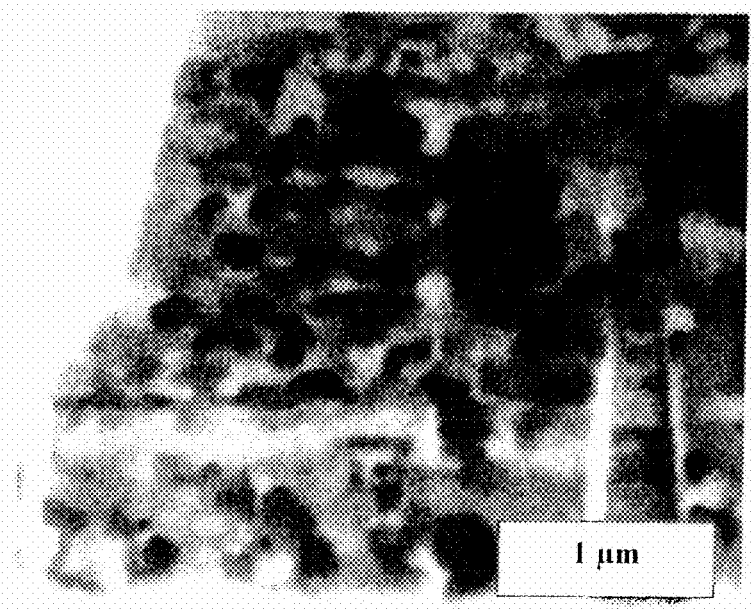
FIG. 23(b) is a micrograph of a cross-section of nanocrystalline 304L stainless steel alloy wire manufactured in accordance with an exemplary embodiment of the present process.
Figures 24A, 24B:
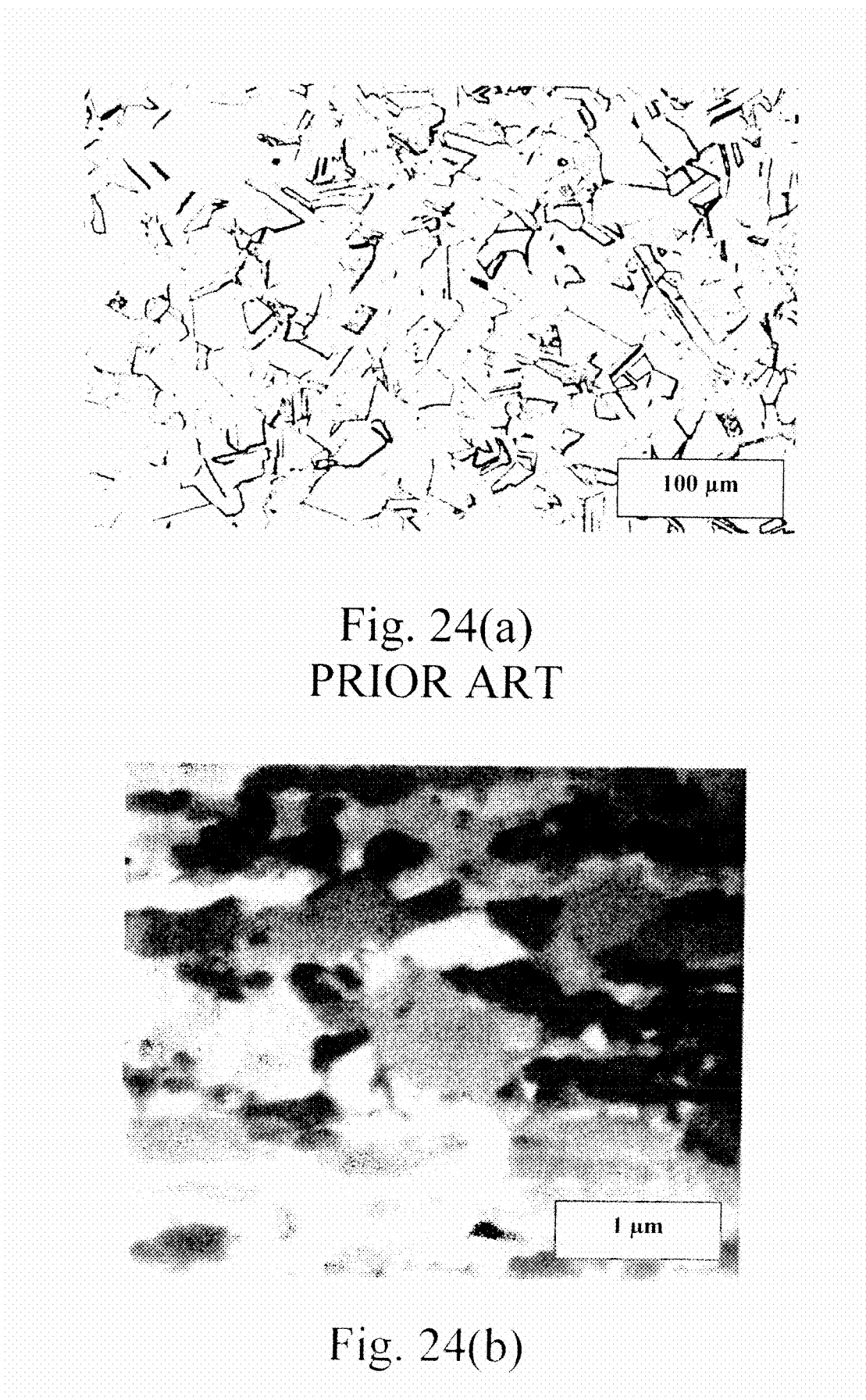
FIG. 24(a) is a micrograph of a cross-section of control 316L stainless steel alloy wire.
FIG. 24(b) is a micrograph of a cross-section of nanocrystalline 316L stainless steel alloy wire manufactured in accordance with an exemplary embodiment of the present process.
Figure 25A:
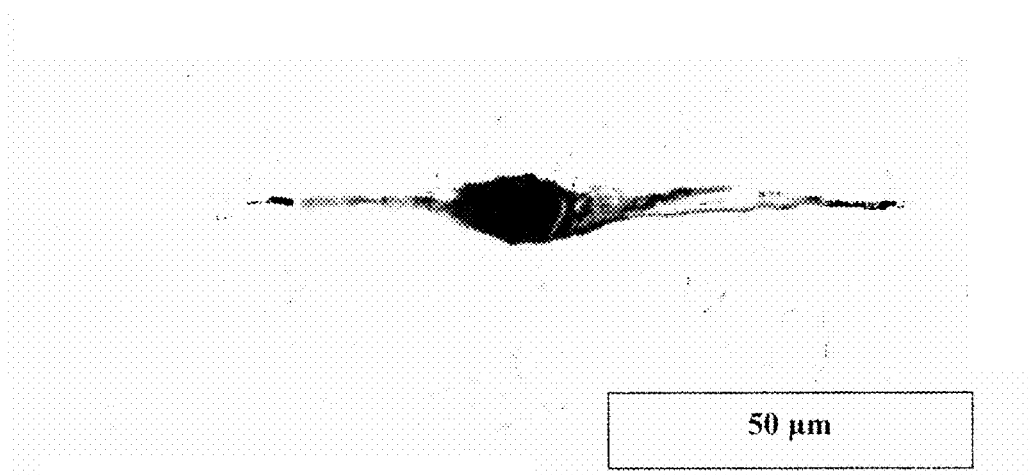
FIG. 25(a) is a micrograph of a cross-section of a control alloy wire made in accordance with the chemical compositional requirements of ASTM F1058.
Figure 25B:
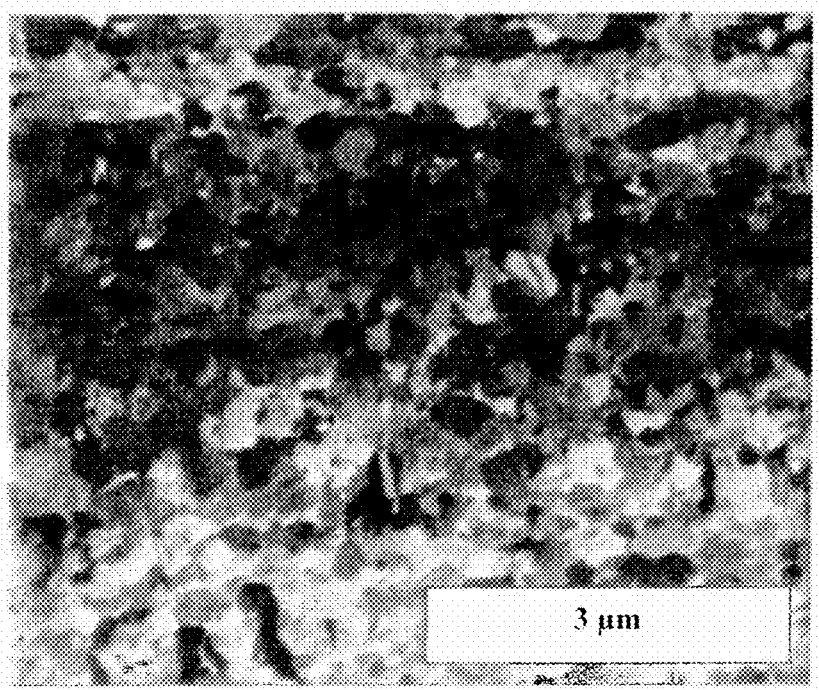
FIG. 25(b) is a micrograph of a cross-section of a control alloy wire made in accordance with the chemical compositional requirements of ASTM F1058 and manufactured in accordance with an exemplary embodiment of the present process.

The nano-recrystallization step was performed at 720° C. at a dwell time of about 2-4 seconds. The resultant nanograin crystal structure was confirmed by ion beam cross section imaging to have a mean grain size of 234 nm (FIG. 23(b), Table 19).

Tensile testing of the nanograined 304L wire was performed as described earlier at 298K in ambient air using a gage length of about 250 mm and a strain rate of 125 mm/min. Observed mechanical properties in accordance with the present process are shown as square-shaped data points 270 including a strain to rupture of 11.9% (Table 3) and a fatigue endurance limit, as determined by rotary beam fatigue testing, at $10^8$ cycles of 0.45% strain amplitude (Table 2, FIG. 19(c)). The control material is shown as circular data points 272 and demonstrate a lower endurance limit at $10^8$ cycles of 0.40% strain amplitude.

TABLE 11

Figure 19A:
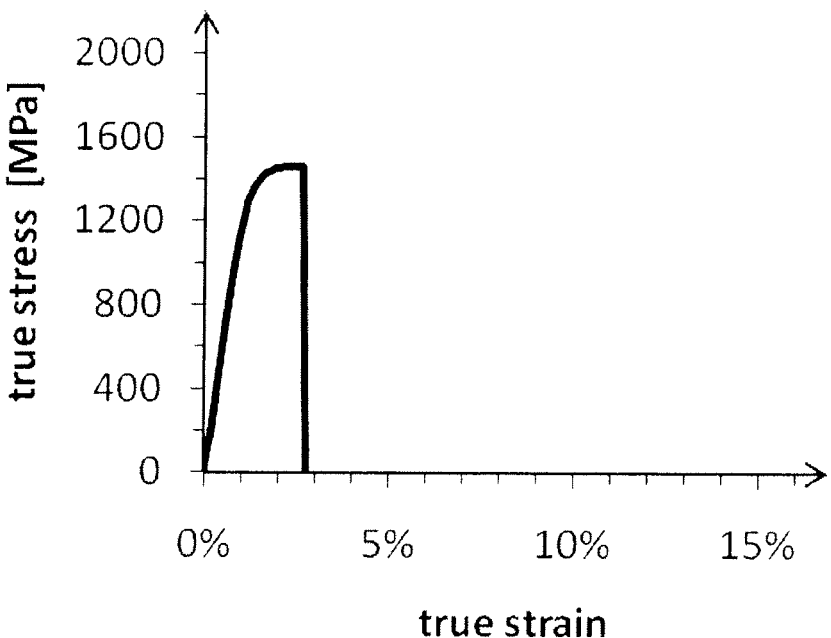

True strain and true stress, 304L control wire, dia. 0.007-in (0.18 mm) - FIG. 19(a)

| True strain (in/in) | True stress (ksi) | True stress (MPa) |
| --- | --- | --- |
| 0.000 | 0.0 | 0.0 |
| 0.001 | 11.6 | 80.3 |
| 0.002 | 26.5 | 183.0 |
| 0.003 | 52.6 | 362.6 |
| 0.004 | 78.0 | 537.8 |
| 0.005 | 101.9 | 702.8 |
| 0.007 | 124.5 | 858.4 |
| 0.008 | 145.0 | 999.8 |
| 0.009 | 162.6 | 1121.0 |
| 0.010 | 176.5 | 1217.2 |
| 0.011 | 186.8 | 1288.1 |
| 0.013 | 194.4 | 1340.6 |
| 0.014 | 199.8 | 1377.6 |
| 0.015 | 203.9 | 1405.8 |
| 0.016 | 206.7 | 1425.2 |
| 0.018 | 208.7 | 1438.8 |
| 0.019 | 209.9 | 1447.4 |
| 0.020 | 210.6 | 1452.2 |
| 0.021 | 211.2 | 1455.9 |
| 0.023 | 211.4 | 1457.7 |
| 0.024 | 211.5 | 1458.5 |
| 0.025 | 211.5 | 1458.3 |
| 0.026 | 211.5 | 1458.1 |
| 0.027 | 0.0 | 0.0 |

TABLE 12

Figure 19B:
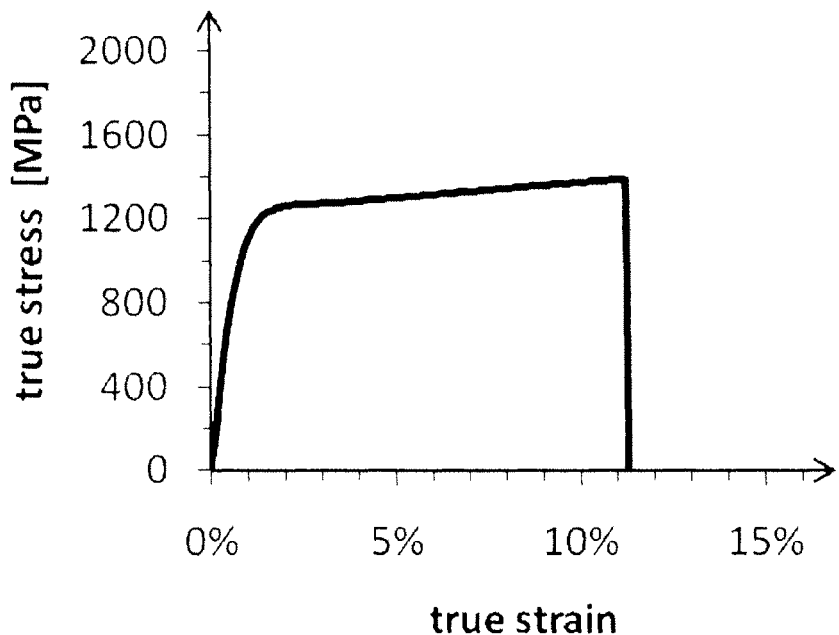

True strain and true stress, nanograin 304L wire, dia. 0.007-in (0.18 mm) - FIG. 19(b)

| True strain (in/in) | True stress (ksi) | True stress (MPa) |
| --- | --- | --- |
| 0.000 | 0.0 | 0.0 |
| 0.000 | 5.6 | 38.5 |
| 0.001 | 26.4 | 182.0 |
| 0.002 | 62.1 | 428.0 |
| 0.004 | 89.0 | 613.9 |

TABLE 12-continued

True strain and true stress, nanograin 304L wire, dia. 0.007-in (0.18 mm) - FIG. 19(b)

| True strain (in/in) | True stress (ksi) | True stress (MPa) |
| --- | --- | --- |
| 0.005 | 109.3 | 753.9 |
| 0.006 | 126.2 | 869.9 |
| 0.007 | 140.1 | 966.0 |
| 0.009 | 151.5 | 1044.8 |
| 0.010 | 160.6 | 1107.3 |
| 0.011 | 167.6 | 1155.3 |
| 0.012 | 172.6 | 1189.9 |
| 0.014 | 176.0 | 1213.7 |
| 0.015 | 178.5 | 1230.9 |
| 0.016 | 180.2 | 1242.1 |
| 0.017 | 181.4 | 1250.5 |
| 0.019 | 182.2 | 1256.0 |
| 0.020 | 182.7 | 1259.5 |
| 0.021 | 183.2 | 1263.0 |
| 0.022 | 183.4 | 1264.5 |
| 0.023 | 183.6 | 1266.1 |
| 0.025 | 183.9 | 1267.6 |
| 0.026 | 183.9 | 1268.2 |
| 0.027 | 184.2 | 1269.7 |
| 0.028 | 184.2 | 1270.3 |
| 0.030 | 184.5 | 1271.8 |
| 0.031 | 184.7 | 1273.4 |
| 0.032 | 184.8 | 1273.9 |
| 0.033 | 185.0 | 1275.5 |
| 0.034 | 185.2 | 1277.0 |
| 0.036 | 185.4 | 1278.6 |
| 0.037 | 185.7 | 1280.1 |
| 0.038 | 185.7 | 1280.6 |
| 0.039 | 186.0 | 1282.2 |
| 0.040 | 186.2 | 1283.7 |
| 0.042 | 186.6 | 1286.3 |
| 0.043 | 186.6 | 1286.8 |
| 0.044 | 187.0 | 1289.4 |
| 0.045 | 187.2 | 1290.9 |
| 0.046 | 187.5 | 1292.4 |
| 0.048 | 187.7 | 1294.0 |
| 0.049 | 187.9 | 1295.5 |
| 0.050 | 188.1 | 1297.1 |
| 0.051 | 188.3 | 1298.6 |
| 0.052 | 188.7 | 1301.2 |
| 0.054 | 188.9 | 1302.7 |
| 0.055 | 189.2 | 1304.3 |
| 0.056 | 189.5 | 1306.8 |
| 0.057 | 189.8 | 1308.4 |
| 0.058 | 190.0 | 1309.9 |
| 0.059 | 190.4 | 1312.5 |
| 0.061 | 190.6 | 1314.0 |
| 0.062 | 190.8 | 1315.6 |
| 0.063 | 191.0 | 1317.1 |
| 0.064 | 191.3 | 1318.7 |
| 0.065 | 191.5 | 1320.2 |
| 0.066 | 191.9 | 1322.8 |
| 0.068 | 192.1 | 1324.3 |
| 0.069 | 192.3 | 1325.9 |
| 0.070 | 192.5 | 1327.4 |
| 0.071 | 192.8 | 1329.0 |
| 0.072 | 193.1 | 1331.5 |
| 0.073 | 193.4 | 1333.1 |
| 0.075 | 193.6 | 1334.6 |
| 0.076 | 193.8 | 1336.2 |
| 0.077 | 194.2 | 1338.8 |
| 0.078 | 194.4 | 1340.3 |
| 0.079 | 194.6 | 1341.9 |
| 0.080 | 194.8 | 1343.4 |
| 0.082 | 195.1 | 1345.0 |
| 0.083 | 195.3 | 1346.5 |
| 0.084 | 195.5 | 1348.1 |
| 0.085 | 195.7 | 1349.6 |
| 0.086 | 196.1 | 1352.2 |
| 0.087 | 196.4 | 1353.8 |
| 0.088 | 196.6 | 1355.3 |
| 0.090 | 196.8 | 1356.9 |
| 0.091 | 197.0 | 1358.4 |

TABLE 12-continued

True strain and true stress, nanograin 304L wire, dia. 0.007-in (0.18 mm) - FIG. 19(b)

| True strain (in/in) | True stress (ksi) | True stress (MPa) |
|---|---|---|
| 0.092 | 197.3 | 1360.0 |
| 0.093 | 197.5 | 1361.5 |
| 0.094 | 197.9 | 1364.1 |
| 0.095 | 198.1 | 1365.7 |
| 0.096 | 198.2 | 1366.2 |
| 0.098 | 198.5 | 1368.8 |
| 0.099 | 198.8 | 1370.3 |
| 0.100 | 199.0 | 1371.9 |
| 0.101 | 199.2 | 1373.5 |
| 0.102 | 199.4 | 1375.0 |
| 0.103 | 199.7 | 1376.6 |
| 0.104 | 199.9 | 1378.1 |
| 0.105 | 200.1 | 1379.7 |
| 0.107 | 200.3 | 1381.2 |
| 0.108 | 200.6 | 1382.8 |
| 0.109 | 200.8 | 1384.3 |
| 0.110 | 201.0 | 1385.9 |
| 0.111 | 201.1 | 1386.3 |
| 0.112 | 201.3 | 1387.9 |
| 0.113 | 0.0 | 0.0 |

TABLE 13

Figure 19C:
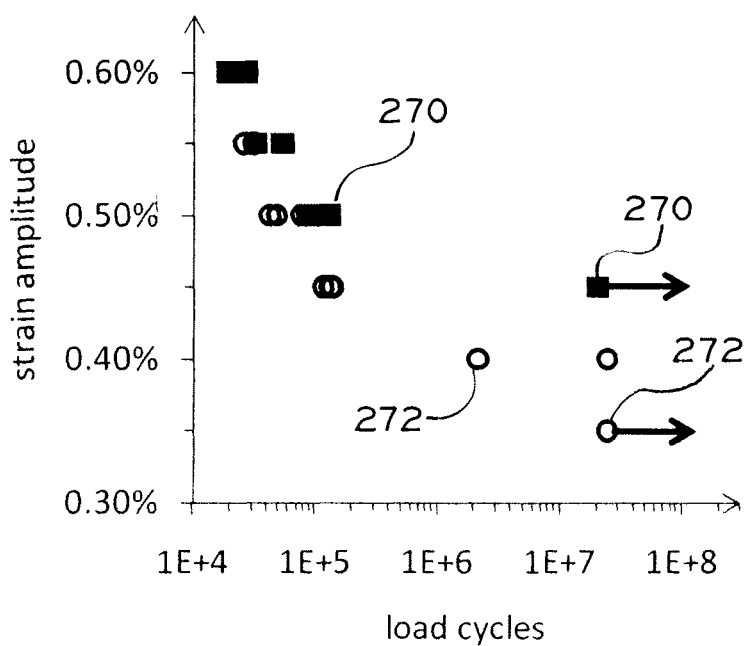

Fatigue data, control and nanograin 304L wire, dia. 0.007-in (0.18 mm) - FIG. 19(c)

| load cycles | strain amplitude |
|---|---|
| Nanograin | |
| 28,080 | 0.60% |
| 24,624 | 0.60% |
| 19,080 | 0.60% |
| 52,272 | 0.55% |
| 55,044 | 0.55% |
| 32,868 | 0.55% |
| 133,056 | 0.50% |
| 85,428 | 0.50% |
| 109,512 | 0.50% |
| 20,992,068 | 0.45% |
| 20,978,352 | 0.45% |
| 20,870,244 | 0.45% |
| 20,392,164 | 0.45% |
| 20,349,936 | 0.45% |
| 20,337,984 | 0.45% |
| 20,280,276 | 0.45% |
| Control | |
| 20,052 | 0.60% |
| 20,340 | 0.60% |
| 21,276 | 0.60% |
| 31,032 | 0.55% |
| 31,608 | 0.55% |
| 26,388 | 0.55% |
| 76,248 | 0.50% |
| 42,444 | 0.50% |
| 48,636 | 0.50% |
| 138,132 | 0.45% |
| 134,712 | 0.45% |
| 117,036 | 0.45% |
| 21,600,000 | 0.40% |
| 21,600,000 | 0.40% |
| 21,600,000 | 0.40% |
| 21,600,000 | 0.40% |
| 21,600,000 | 0.40% |
| 21,600,000 | 0.40% |

Example 7

316L Stainless Steel

Figure 20A:
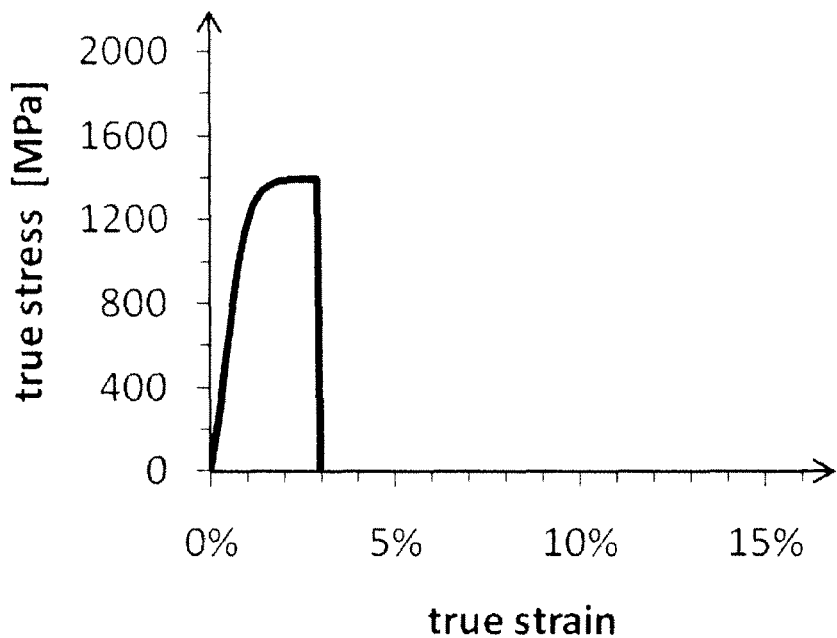
Figure 20B:
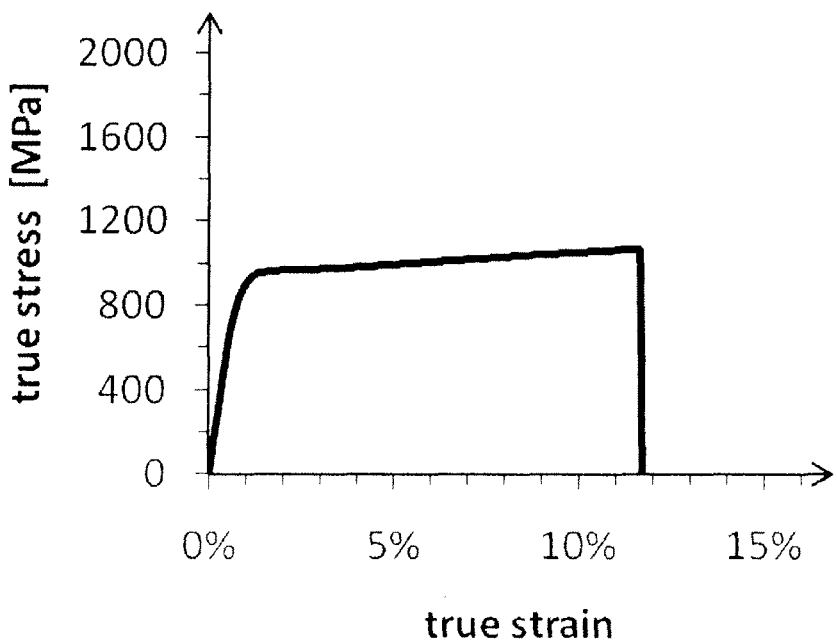
Figure 20C:
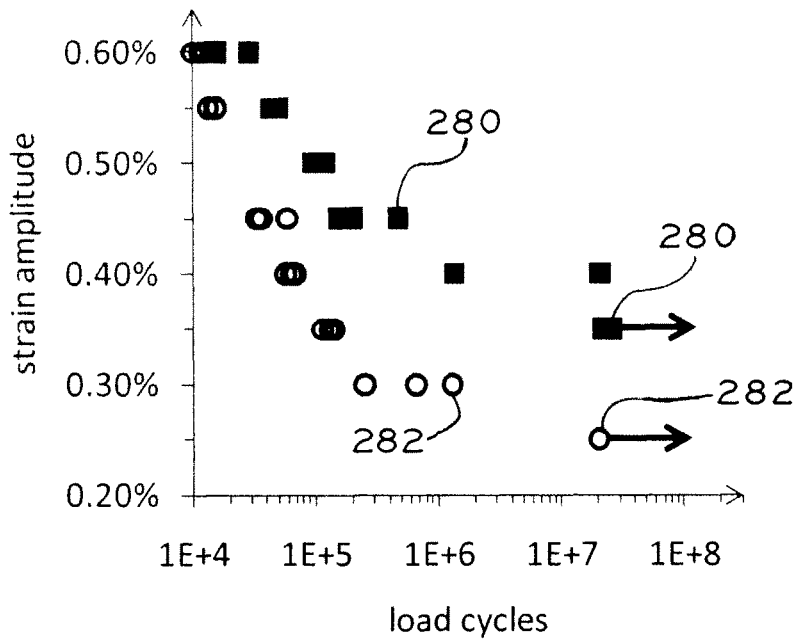

Referring to FIGS. 20(a)-20(c) and Tables 14-16, and 19 below, in this Example 216L round wire with a diameter of 0.0070-in (0.18 mm) was produced and tested. The wires exhibited properties and characteristics in accordance with an embodiment of the present process.

1. Experimental Technique

The process started with a VIM (vacuum induction melted) 304L ingot that was processed by hot rolling into rod stock. The material was then iteratively cold worked and annealed in a conventional manner to a diameter of 1.8 mm to yield an equiaxed grain structure with a mean grain size of about 10 to 20 µm.

With respect to the cold work conditioning and nano-recrystallization steps of the present process, it has been found that preparation of 316L alloy for nano-recrystallization entails a relatively high amount of deformation in the cold work conditioning step as described below.

In the present example, the annealed wires having diameter 1.8 mm were subjected to a cold work conditioning step by drawing to a diameter of 0.18 mm in preparation for nanorecrystallization. According to Formula I above, the cold work conditioning steps therefore imparted nominally 99.1% cold work (4.66 units true strain according to Formula II above) to the material.

2. Results

The nano-recrystallization step was performed at 780° C. at a dwell time of about 4-6 seconds. The resultant nanograin crystal structure was confirmed by ion beam cross section imaging to have a mean grain size of 311 nm (FIG. 316(b), Table 19).

Tensile testing of the nanograined 316L wire was performed as described earlier at 298K in ambient air using a gage length of about 250 mm and a strain rate of 125 mm/min. Observed mechanical properties were accordance with the present process including a strain to rupture of 12.3% (Table 3) and a fatigue endurance limit, as determined by rotary beam fatigue testing, shown by square shaped marks 280 on FIG. 20(c) at $10^8$ cycles of 0.35% strain amplitude (Table 2, FIG. 20(c)). The control material is shown as circular data points 282 and demonstrate a lower endurance limit at $10^8$ cycles of 0.25% strain amplitude.

TABLE 14

True strain and true stress, control 316L wire, dia. 0.007-in (0.18 mm) - FIG. 20(a)

| True strain (in/in) | True stress (ksi) | True stress (MPa) |
|---|---|---|
| 0.000 | 0.0 | 0.0 |
| 0.000 | 10.9 | 75.5 |
| 0.002 | 28.5 | 196.6 |
| 0.003 | 53.9 | 371.4 |
| 0.004 | 80.7 | 556.3 |
| 0.005 | 105.9 | 730.1 |
| 0.007 | 129.3 | 891.6 |
| 0.008 | 150.0 | 1034.0 |
| 0.009 | 165.9 | 1143.6 |
| 0.010 | 176.8 | 1219.2 |
| 0.012 | 184.6 | 1272.6 |
| 0.013 | 190.1 | 1310.4 |
| 0.014 | 194.1 | 1338.5 |
| 0.015 | 196.9 | 1357.8 |
| 0.016 | 198.7 | 1370.3 |

TABLE 14-continued

True strain and true stress, control 316L wire,
dia. 0.007-in (0.18 mm) - FIG. 20(a)

| True strain (in/in) | True stress (ksi) | True stress (MPa) |
|---|---|---|
| 0.018 | 200.0 | 1378.9 |
| 0.019 | 200.7 | 1383.5 |
| 0.020 | 201.2 | 1387.2 |
| 0.021 | 201.4 | 1388.9 |
| 0.023 | 201.7 | 1390.6 |
| 0.024 | 201.8 | 1391.3 |
| 0.025 | 201.8 | 1391.0 |
| 0.026 | 201.7 | 1390.7 |
| 0.027 | 201.8 | 1391.4 |
| 0.029 | 201.6 | 1390.1 |
| 0.030 | 0.0 | 0.0 |

TABLE 15

True strain and true stress, nanograin 316L wire,
dia. 0.007-in (0.18 mm) - FIG. 20(b)

| True strain (in/in) | True stress (ksi) | True stress (MPa) |
|---|---|---|
| 0.000 | 0.0 | 0.0 |
| 0.001 | 16.6 | 114.7 |
| 0.002 | 29.3 | 202.2 |
| 0.003 | 53.5 | 368.8 |
| 0.004 | 76.3 | 526.2 |
| 0.005 | 95.6 | 659.3 |
| 0.007 | 110.8 | 764.1 |
| 0.008 | 121.8 | 839.6 |
| 0.009 | 129.0 | 889.4 |
| 0.010 | 133.5 | 920.2 |
| 0.012 | 136.1 | 938.6 |
| 0.013 | 137.8 | 950.3 |
| 0.014 | 138.7 | 956.3 |
| 0.015 | 139.3 | 960.4 |
| 0.017 | 139.6 | 962.5 |
| 0.018 | 139.8 | 963.7 |
| 0.019 | 139.9 | 964.9 |
| 0.020 | 140.1 | 966.1 |
| 0.022 | 140.1 | 966.3 |
| 0.023 | 140.2 | 966.5 |
| 0.024 | 140.4 | 967.7 |
| 0.025 | 140.4 | 967.9 |
| 0.026 | 140.6 | 969.1 |
| 0.028 | 140.7 | 970.2 |
| 0.029 | 140.8 | 970.4 |
| 0.030 | 140.9 | 971.6 |
| 0.031 | 141.0 | 971.8 |
| 0.032 | 141.3 | 974.0 |
| 0.034 | 141.4 | 975.2 |
| 0.035 | 141.6 | 976.3 |
| 0.036 | 141.6 | 976.5 |
| 0.037 | 141.8 | 977.7 |
| 0.039 | 142.0 | 978.9 |
| 0.040 | 142.1 | 980.1 |
| 0.041 | 142.3 | 981.3 |
| 0.042 | 142.6 | 983.4 |
| 0.043 | 142.8 | 984.6 |
| 0.045 | 143.0 | 985.8 |
| 0.046 | 143.1 | 987.0 |
| 0.047 | 143.3 | 988.1 |
| 0.048 | 143.6 | 990.3 |
| 0.049 | 143.8 | 991.5 |
| 0.050 | 144.0 | 992.7 |
| 0.052 | 144.1 | 993.9 |
| 0.053 | 144.5 | 996.0 |
| 0.054 | 144.6 | 997.2 |
| 0.055 | 144.8 | 998.4 |
| 0.056 | 145.1 | 1000.6 |
| 0.058 | 145.3 | 1001.8 |
| 0.059 | 145.5 | 1002.9 |
| 0.060 | 145.6 | 1004.1 |
| 0.061 | 145.8 | 1005.3 |
| 0.062 | 146.1 | 1007.5 |
| 0.063 | 146.3 | 1008.7 |
| 0.065 | 146.5 | 1009.9 |
| 0.066 | 146.6 | 1011.1 |
| 0.067 | 147.0 | 1013.3 |
| 0.068 | 147.1 | 1014.4 |
| 0.069 | 147.3 | 1015.6 |
| 0.071 | 147.6 | 1017.8 |
| 0.072 | 147.8 | 1019.0 |
| 0.073 | 148.0 | 1020.2 |
| 0.074 | 148.1 | 1021.4 |
| 0.075 | 148.3 | 1022.6 |
| 0.076 | 148.6 | 1024.8 |
| 0.077 | 148.8 | 1026.0 |
| 0.079 | 149.0 | 1027.2 |
| 0.080 | 149.2 | 1028.3 |
| 0.081 | 149.3 | 1029.5 |
| 0.082 | 149.5 | 1030.7 |
| 0.083 | 149.7 | 1031.9 |
| 0.084 | 149.8 | 1033.1 |
| 0.086 | 150.2 | 1035.3 |
| 0.087 | 150.3 | 1036.5 |
| 0.088 | 150.5 | 1037.7 |
| 0.089 | 150.7 | 1038.9 |
| 0.090 | 150.9 | 1040.1 |
| 0.091 | 151.0 | 1041.3 |
| 0.092 | 151.2 | 1042.4 |
| 0.094 | 151.4 | 1043.6 |
| 0.095 | 151.5 | 1044.8 |
| 0.096 | 151.7 | 1046.0 |
| 0.097 | 151.9 | 1047.2 |
| 0.098 | 152.2 | 1049.4 |
| 0.099 | 152.4 | 1050.6 |
| 0.100 | 152.4 | 1050.8 |
| 0.102 | 152.6 | 1052.0 |
| 0.103 | 152.7 | 1053.1 |
| 0.104 | 152.9 | 1054.3 |
| 0.105 | 153.1 | 1055.5 |
| 0.106 | 153.3 | 1056.7 |
| 0.107 | 153.4 | 1057.9 |
| 0.108 | 153.6 | 1059.1 |
| 0.109 | 153.8 | 1060.3 |
| 0.111 | 153.8 | 1060.4 |
| 0.112 | 154.1 | 1062.7 |
| 0.113 | 154.3 | 1063.9 |
| 0.114 | 154.5 | 1065.0 |
| 0.115 | 154.5 | 1065.2 |
| 0.116 | 154.7 | 1066.4 |
| 0.117 | 0.0 | 0.0 |

TABLE 16

Fatigue data, control and nanograin 316L
wire, dia. 0.007-in (0.18 mm) - FIG. 20(c)

| load cycles | strain amplitude |
|---|---|
| Nanograin | |
| 28,908 | 0.60% |
| 15,624 | 0.60% |
| 29,088 | 0.60% |
| 43,704 | 0.55% |
| 47,016 | 0.55% |
| 49,644 | 0.55% |
| 95,868 | 0.50% |

TABLE 16-continued

Fatigue data, control and nanograin 316L
wire, dia. 0.007-in (0.18 mm) - FIG. 20(c)

| load cycles | strain amplitude |
|---|---|
| 102,276 | 0.50% |
| 119,016 | 0.50% |
| 203,688 | 0.45% |
| 154,440 | 0.45% |
| 470,988 | 0.45% |
| 1,363,356 | 0.40% |
| 20,978,136 | 0.40% |
| 20,953,764 | 0.40% |
| 25,952,400 | 0.35% |
| 24,659,928 | 0.35% |
| 24,600,240 | 0.35% |
| 25,952,508 | 0.35% |
| 24,659,928 | 0.35% |
| 24,600,240 | 0.35% |
| 21,876,696 | 0.35% |
| Control | |
| 11,628 | 0.60% |
| 10,080 | 0.60% |
| 12,672 | 0.60% |
| 15,336 | 0.55% |
| 13,428 | 0.55% |
| 15,660 | 0.55% |
| 35,964 | 0.45% |
| 58,392 | 0.45% |
| 33,192 | 0.45% |
| 56,952 | 0.40% |
| 63,360 | 0.40% |
| 67,716 | 0.40% |
| 113,688 | 0.35% |
| 130,176 | 0.35% |
| 142,164 | 0.35% |
| 291,600 | 0.30% |
| 20,160,000 | 0.30% |
| 20,160,000 | 0.30% |
| 21,600,000 | 0.25% |
| 21,600,000 | 0.25% |
| 21,600,000 | 0.25% |
| 21,600,000 | 0.25% |
| 21,600,000 | 0.25% |
| 21,600,000 | 0.25% |
| 21,600,000 | 0.25% |

Example 7

ASTM F1058 Material

Referring to FIGS. 21(*a*)-21(*c*) and Tables 17-19 below, in this Example FWM 1058 shaped wire with a diameter of 0.0070-in (0.18 mm) was produced and tested. The wires exhibited properties and characteristics in accordance with an embodiment of the present process.

1. Experimental Technique

The process started with a VIM (vacuum induction melted) FWM 1058 ingot that was processed by hot rolling into rod stock. The material was then iteratively cold worked and annealed in a conventional manner to a diameter of 1.15 mm to yield an equiaxed grain structure with a mean grain size of about 10 to 20 μm.

With respect to the cold work conditioning and nano-recrystallization steps of the present process, it has been found that preparation of FWM 1058 alloy for nano-recrystallization entails a relatively high amount of deformation in the cold work conditioning step as described below.

In the present example, the annealed wires having diameter 1.15 mm were subjected to a cold work conditioning step by drawing to a diameter of 0.225 mm in preparation for nano-recrystallization. According to Formula I above, the cold work conditioning steps therefore imparted nominally 96.1% cold work (3.26 units true strain according to Formula II above) to the material.

2. Results

The nano-recrystallization step was performed at 850° C. at a dwell time of about 0.5 to 2 seconds. The resultant nanograin crystal structure was confirmed by ion beam cross section imaging to have a mean grain size of 247 nm (FIG. 1058*b*, Table 19).

Tensile testing of the nanograined FWM 1058 wire was performed as described earlier at 298K in ambient air using a gage length of about 250 mm and a strain rate of 125 mm/min. Observed mechanical properties were accordance with the present process including a yield strength of 1409 MPa, a strain to rupture of 17.9% (Table 3) and a fatigue endurance limit, as determined by rotary beam fatigue testing, at $10^8$ cycles of 0.45% strain amplitude, shown as circular data points 290 in FIG. 21(*b*) (Table 2, FIG. 21(*b*)). The control material is shown as circular data points 292 and demonstrate a lower endurance limit at $10^8$ cycles of 0.40% strain amplitude.

TABLE 17

Figure 21A:
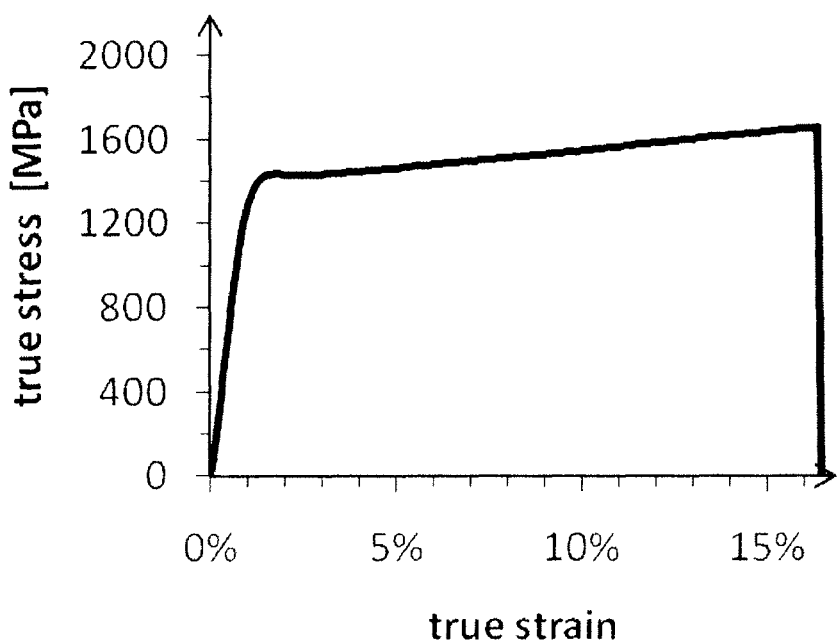

True strain and true stress, nanograin 1058 wire,
dia. 0.0089-in (0.23 mm) - FIG. 21(a)

| True strain (in/in) | True stress (ksi) | True stress (MPa) |
|---|---|---|
| 0.000 | 0.0 | 0.0 |
| 0.000 | 0.9 | 6.0 |
| 0.001 | 18.6 | 128.3 |
| 0.002 | 47.3 | 326.3 |
| 0.004 | 76.3 | 526.0 |
| 0.005 | 104.5 | 720.2 |
| 0.006 | 131.4 | 905.8 |
| 0.007 | 155.2 | 1070.0 |
| 0.009 | 174.0 | 1199.4 |
| 0.010 | 187.5 | 1292.6 |
| 0.011 | 196.3 | 1353.2 |
| 0.012 | 201.8 | 1391.5 |
| 0.014 | 205.0 | 1413.3 |
| 0.015 | 206.7 | 1425.4 |
| 0.016 | 207.5 | 1430.9 |
| 0.017 | 207.9 | 1433.2 |
| 0.018 | 207.9 | 1433.1 |
| 0.020 | 207.8 | 1432.5 |
| 0.021 | 207.6 | 1431.1 |
| 0.022 | 207.3 | 1429.2 |
| 0.023 | 207.2 | 1428.5 |
| 0.025 | 207.2 | 1428.4 |
| 0.026 | 207.2 | 1428.9 |
| 0.027 | 207.3 | 1429.4 |
| 0.028 | 207.5 | 1430.5 |
| 0.029 | 207.6 | 1431.0 |
| 0.031 | 207.8 | 1432.7 |
| 0.032 | 208.0 | 1433.9 |
| 0.033 | 208.2 | 1435.6 |
| 0.034 | 208.5 | 1437.3 |
| 0.036 | 208.7 | 1439.1 |
| 0.037 | 209.0 | 1440.8 |
| 0.038 | 209.2 | 1442.5 |
| 0.039 | 209.5 | 1444.3 |
| 0.040 | 209.7 | 1446.0 |
| 0.042 | 210.0 | 1447.7 |
| 0.043 | 210.2 | 1449.5 |
| 0.044 | 210.5 | 1451.2 |
| 0.045 | 210.8 | 1453.6 |
| 0.046 | 211.1 | 1455.3 |
| 0.048 | 211.3 | 1457.1 |
| 0.049 | 211.6 | 1458.8 |
| 0.050 | 211.9 | 1461.2 |
| 0.051 | 212.2 | 1462.9 |

TABLE 17-continued

True strain and true stress, nanograin 1058 wire, dia. 0.0089-in (0.23 mm) - FIG. 21(a)

| True strain (in/in) | True stress (ksi) | True stress (MPa) |
|---|---|---|
| 0.052 | 212.5 | 1465.3 |
| 0.053 | 212.9 | 1467.6 |
| 0.055 | 213.1 | 1469.4 |
| 0.056 | 213.5 | 1471.8 |
| 0.057 | 213.7 | 1473.5 |
| 0.058 | 214.1 | 1475.9 |
| 0.059 | 214.4 | 1478.3 |
| 0.061 | 214.7 | 1480.0 |
| 0.062 | 215.0 | 1482.4 |
| 0.063 | 215.3 | 1484.1 |
| 0.064 | 215.6 | 1486.5 |
| 0.065 | 215.9 | 1488.2 |
| 0.066 | 216.2 | 1490.6 |
| 0.068 | 216.5 | 1492.4 |
| 0.069 | 216.8 | 1494.8 |
| 0.070 | 217.1 | 1496.5 |
| 0.071 | 217.3 | 1498.3 |
| 0.072 | 217.6 | 1500.0 |
| 0.073 | 217.9 | 1502.4 |
| 0.075 | 218.1 | 1503.5 |
| 0.076 | 218.3 | 1505.2 |
| 0.077 | 218.6 | 1507.0 |
| 0.078 | 218.8 | 1508.7 |
| 0.079 | 219.0 | 1509.8 |
| 0.080 | 219.3 | 1512.2 |
| 0.081 | 219.5 | 1513.3 |
| 0.083 | 219.8 | 1515.7 |
| 0.084 | 220.0 | 1516.8 |
| 0.085 | 220.2 | 1518.5 |
| 0.086 | 220.5 | 1520.3 |
| 0.087 | 220.8 | 1522.0 |
| 0.088 | 221.1 | 1524.4 |
| 0.090 | 221.4 | 1526.2 |
| 0.091 | 221.6 | 1527.9 |
| 0.092 | 222.0 | 1530.3 |
| 0.093 | 222.1 | 1531.4 |
| 0.094 | 222.5 | 1533.8 |
| 0.095 | 222.7 | 1535.6 |
| 0.096 | 223.1 | 1538.0 |
| 0.097 | 223.4 | 1540.4 |
| 0.099 | 223.7 | 1542.1 |
| 0.100 | 224.0 | 1544.5 |
| 0.101 | 224.3 | 1546.3 |
| 0.102 | 224.6 | 1548.7 |
| 0.103 | 224.9 | 1550.4 |
| 0.104 | 225.3 | 1553.5 |
| 0.105 | 225.6 | 1555.3 |
| 0.107 | 225.9 | 1557.7 |
| 0.108 | 226.2 | 1559.4 |
| 0.109 | 226.5 | 1561.9 |
| 0.110 | 226.8 | 1563.6 |
| 0.111 | 227.1 | 1566.0 |
| 0.112 | 227.4 | 1567.8 |
| 0.113 | 227.7 | 1570.2 |
| 0.114 | 228.0 | 1572.0 |
| 0.115 | 228.3 | 1574.4 |
| 0.117 | 228.7 | 1576.8 |
| 0.118 | 228.9 | 1577.9 |
| 0.119 | 229.2 | 1580.3 |
| 0.120 | 229.5 | 1582.1 |
| 0.121 | 229.8 | 1584.5 |
| 0.122 | 230.0 | 1585.6 |
| 0.123 | 230.3 | 1588.0 |
| 0.124 | 230.7 | 1590.5 |
| 0.125 | 230.9 | 1592.2 |
| 0.127 | 231.3 | 1594.7 |
| 0.128 | 231.5 | 1596.4 |
| 0.129 | 231.8 | 1598.2 |
| 0.130 | 232.2 | 1600.6 |
| 0.131 | 232.4 | 1602.4 |
| 0.132 | 232.7 | 1604.1 |
| 0.133 | 233.0 | 1606.6 |
| 0.134 | 233.3 | 1608.3 |
| 0.135 | 233.5 | 1610.1 |
| 0.136 | 233.8 | 1611.8 |
| 0.138 | 234.0 | 1613.6 |
| 0.139 | 234.2 | 1614.7 |
| 0.140 | 234.5 | 1617.1 |
| 0.141 | 234.7 | 1618.2 |
| 0.142 | 235.0 | 1619.9 |
| 0.143 | 235.3 | 1622.4 |
| 0.144 | 235.6 | 1624.2 |
| 0.145 | 235.8 | 1625.9 |
| 0.146 | 236.1 | 1627.7 |
| 0.147 | 236.3 | 1629.4 |
| 0.148 | 236.6 | 1631.2 |
| 0.149 | 236.8 | 1632.9 |
| 0.150 | 237.1 | 1634.7 |
| 0.152 | 237.3 | 1636.5 |
| 0.153 | 237.6 | 1638.2 |
| 0.154 | 237.9 | 1640.0 |
| 0.155 | 238.0 | 1641.0 |
| 0.156 | 238.3 | 1642.8 |
| 0.157 | 238.5 | 1644.5 |
| 0.158 | 238.8 | 1646.3 |
| 0.159 | 238.9 | 1647.3 |
| 0.160 | 239.2 | 1649.1 |
| 0.161 | 239.3 | 1650.2 |
| 0.162 | 239.6 | 1651.9 |
| 0.163 | 239.7 | 1653.0 |
| 0.164 | 0.0 | 0.0 |

TABLE 18

Figure 21B:
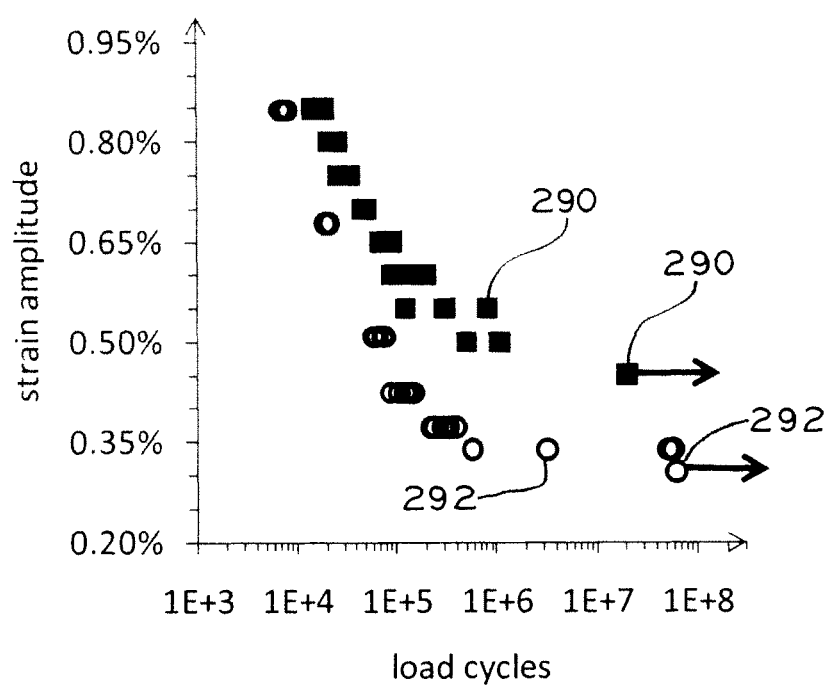

Fatigue data, control and nanograin 1058 wire, dia. 0.0089-in (0.23 mm) - FIG. 21(b)

| Nanograin | | Control | |
|---|---|---|---|
| load cycles | strain amplitude | load cycles | strain amplitude |
| 14,832 | 0.85% | 7,380 | 0.85% |
| 15,912 | 0.85% | 7,272 | 0.85% |
| 19,188 | 0.85% | 7,380 | 0.85% |
| 21,420 | 0.80% | 7,776 | 0.85% |
| 25,668 | 0.80% | 7,452 | 0.85% |
| 26,388 | 0.80% | 7,020 | 0.85% |
| 28,980 | 0.75% | 8,172 | 0.85% |
| 34,776 | 0.75% | 20,736 | 0.68% |
| 26,676 | 0.75% | 20,844 | 0.68% |
| 47,520 | 0.70% | 19,404 | 0.68% |
| 45,540 | 0.70% | 20,376 | 0.68% |
| 50,364 | 0.70% | 19,908 | 0.68% |
| 93,456 | 0.65% | 21,456 | 0.68% |
| 70,344 | 0.65% | 20,016 | 0.68% |
| 87,804 | 0.65% | 63,396 | 0.51% |
| 90,864 | 0.60% | 60,048 | 0.51% |
| 199,656 | 0.60% | 61,416 | 0.51% |
| 122,148 | 0.60% | 59,400 | 0.51% |
| 814,392 | 0.55% | 62,676 | 0.51% |
| 307,872 | 0.55% | 77,508 | 0.51% |
| 122,940 | 0.55% | 73,584 | 0.51% |
| 511,596 | 0.50% | 122,868 | 0.42% |
| 1,080,000 | 0.50% | 123,552 | 0.42% |
| 1,080,000 | 0.50% | 137,196 | 0.42% |
| 20,160,000 | 0.45% | 128,736 | 0.42% |
| 20,160,000 | 0.45% | 87,156 | 0.42% |
| 20,160,000 | 0.45% | 150,840 | 0.42% |
| 20,160,000 | 0.45% | 106,812 | 0.42% |
| 20,160,000 | 0.45% | 239,400 | 0.37% |
| 20,160,000 | 0.45% | 332,028 | 0.37% |

TABLE 18-continued

Fatigue data, control and nanograin 1058 wire,
dia. 0.0089-in (0.23 mm) - FIG. 21(b)

| Nanograin | | Control | |
|---|---|---|---|
| load cycles | strain amplitude | load cycles | strain amplitude |
| 20,160,000 | 0.45% | 219,600 | 0.37% |
| | | 321,084 | 0.37% |
| | | 317,376 | 0.37% |
| | | 392,436 | 0.37% |
| | | 291,096 | 0.37% |
| | | 56,872,800 | 0.34% |
| | | 51,642,000 | 0.34% |
| | | 55,537,200 | 0.34% |
| | | 3,216,276 | 0.34% |
| | | 573,012 | 0.34% |
| | | 56,775,600 | 0.34% |
| | | 56,646,000 | 0.34% |
| | | 61,920,000 | 0.31% |
| | | 61,920,000 | 0.31% |
| | | 61,920,000 | 0.31% |
| | | 61,920,000 | 0.31% |
| | | 61,920,000 | 0.31% |
| | | 61,920,000 | 0.31% |
| | | 61,920,000 | 0.31% |

Example 8

Grain Size Determination for Various Materials Made in Accordance with the Present Process 1. Experimental Technique In this example, grain sizes for various materials were measured for a conventional sample of a particular material (the "control" material), and for a second sample after processing the material in accordance with the present process. Grain size images may be determined by any conventional method such as, standard light microscopy, field emission scanning electron microscopy (FE-SEM) or transmission electron microscopy (TEM) as discussed in Section II-A above.

Micrographs of the grain structure of each wire were taken, and appear as FIGS. 23(a) through 26(b) herein.

Figure 22A:
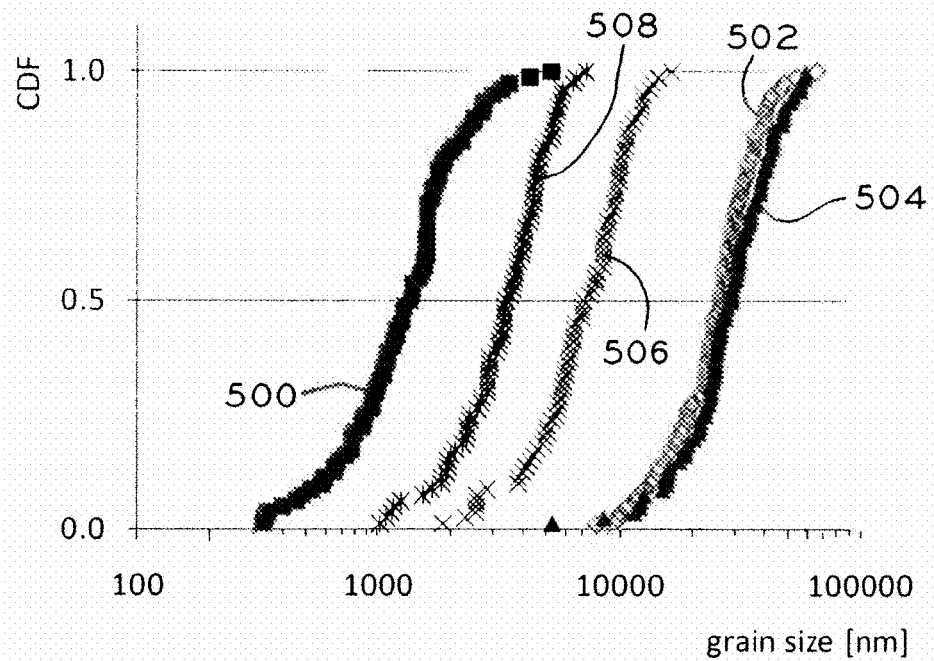
FIG. 22(a) is a cumulative distribution function ("CDF") of grain size for various experimental control wire materials, including 35N LT® alloy wires shown as filled square marks, Nitinol wires shown as asterisk-shaped marks, wires made in accordance with ASTM F1058 shown as X-shaped marks, 304L stainless steel shown as diamond-shaped marks, and 316L stainless steel shown as filled triangular marks
Figure 22B:
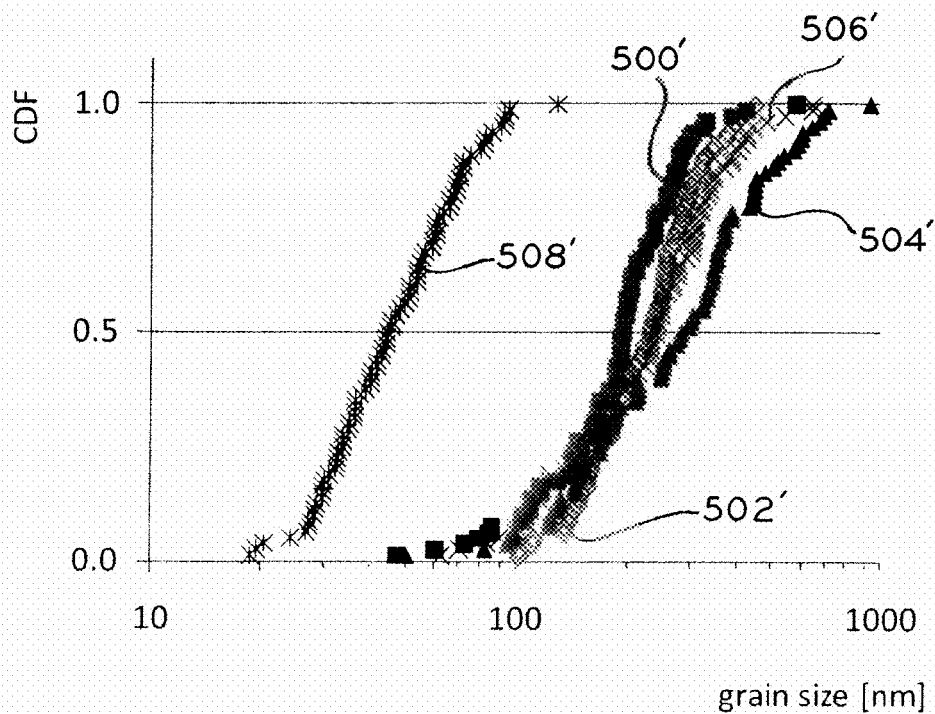
FIG. 22(b) is a cumulative distribution function ("CDF") of grain size for various wire materials manufactured in accordance with the present process, including 35N LT® alloy wires shown as filled square marks, Nitinol wires shown as asterisk-shaped marks, wires made in compliance with the chemical compositional requirements of ASTM F1058 shown as X-shaped marks, 304L stainless steel shown as diamond-shaped marks, and 316L stainless steel shown as filled triangular marks.

The grain size distributions of the control wires are depicted in FIG. 22(a). The grain size distributions of the wires after processing in accordance with the present process are depicted in FIG. 22(b) together with data collected on standard wire materials. Grain size data for each respective wire material is also shown below in Table 19, parts I and II.

2. Results

Data collected on 35N LT® wire is shown on FIGS. 22(a) and 22(b) as filled square shaped marks. The 35N LT® control wire generated data curve 500 illustrating a mean grain size of about 1480 nm, while the 35N LT® wire manufactured in accordance with the present process generated data curve 500' illustrating a mean grain size of about 200 nm. Grain sizes are shown graphically in FIG. 6.

Data collected on 304L stainless steel wire is shown on FIGS. 22(a) and 22(b) as diamond shaped marks. The 304L control wire generated data curve 502 illustrating a mean grain size of about 26,690 nm, while the 304L wire manufactured in accordance with the present process generated data curve 502' illustrating a mean grain size of about 234 nm. Grain sizes are shown graphically in FIGS. 23(a) and 23(b).

Data collected on 316L stainless steel wire is shown on FIGS. 22(a) and 22(b) as triangular marks. The 316L control wire generated data curve 504 illustrating a mean grain size of about 20,020 nm, while the 316L wire manufactured in accordance with the present process generated data curve 504' illustrating a mean grain size of about 311 nm. Grain sizes are shown graphically in FIGS. 24(a) and 24(b).

Data collected on wire made in accordance with the ASTM F1058 standard is shown on FIGS. 22(a) and 22(b) as X-shaped marks. The 1058 control wire generated data curve 506 illustrating a mean grain size of about 7,614 nm, while the 1058 wire manufactured in accordance with the present process generated data curve 506' illustrating a mean grain size of about 247 nm. Grain sizes are shown graphically in FIGS. 25(a) and 25(b).

Data collected on Nitinol wire is shown on FIGS. 22(a) and 22(b) as asterisk-shaped marks. The Nitinol control wire generated data curve 508 illustrating a mean grain size of about 3,573 nm, while the Nitinol wire manufactured in accordance with the present process generated data curve 508' illustrating a mean grain size of about 50 nm. Grain sizes are shown graphically in FIGS. 26(a) and 26(b).

Figure 26A:
FIG. 26(a) is a micrograph of a cross-section of control Nitinol wire.
Figure 26B:
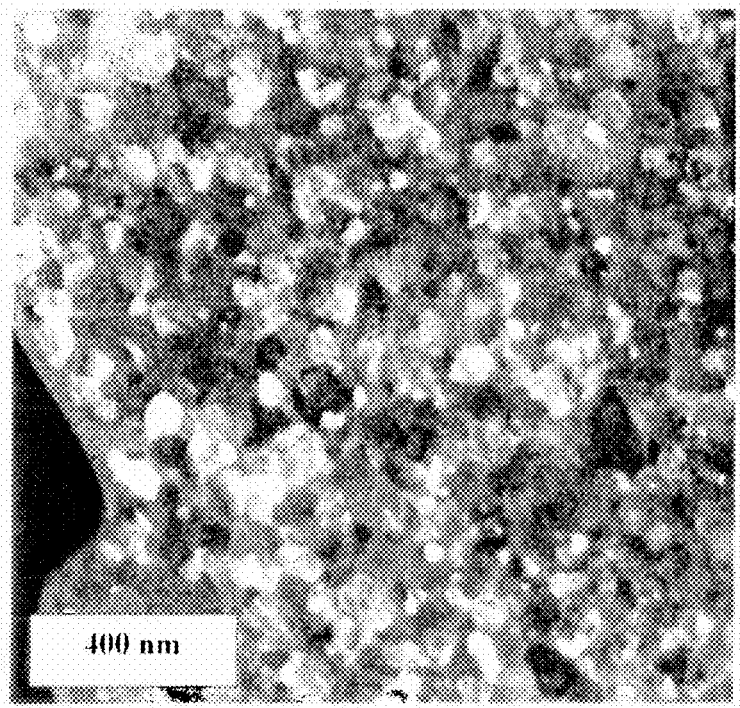
FIG. 26(b) is a micrograph of a cross-section of nanocrystalline Nitinol wire manufactured in accordance with an exemplary embodiment of the present process.

Table 4 and FIGS. 22(a) 26(b) illustrate that processing the above mentioned materials in accordance with an embodiment of the present process results in substantial reduction of grain size, as discussed above.

TABLE 19

| Grain size data for various materials | | | | | | | | | | |
|---|---|---|---|---|---|---|---|---|---|---|
| Control materials (sizes in nm) | | | | | Nanograin materials (sizes in nm) | | | | | |
| 35N LT® | 304L | 316L | 1058 | Nitinol | 35N LT® | 304L | 316L | 1058 | Nitinol | CDF |
| 331 | 8110 | 5300 | 1870 | 1020 | 47 | 103 | 50 | 63 | 19 | 0.0125 |
| 336 | 9910 | 8620 | 2320 | 1090 | 60 | 103 | 82 | 70 | 19 | 0.0250 |
| 345 | 10070 | 11490 | 2560 | 1140 | 73 | 111 | 95 | 84 | 20 | 0.0375 |
| 397 | 10810 | 12070 | 2560 | 1170 | 79 | 112 | 99 | 91 | 24 | 0.0500 |
| 455 | 11710 | 12190 | 2580 | 1250 | 85 | 136 | 99 | 100 | 27 | 0.0625 |
| 484 | 11850 | 12640 | 2600 | 1540 | 86 | 136 | 123 | 100 | 27 | 0.0750 |
| 523 | 12610 | 14940 | 2850 | 1680 | 104 | 140 | 124 | 107 | 27 | 0.0875 |
| 582 | 13510 | 15520 | 3850 | 1850 | 105 | 140 | 125 | 107 | 28 | 0.1000 |
| 596 | 13780 | 15610 | 3850 | 1850 | 110 | 144 | 129 | 107 | 28 | 0.1125 |
| 653 | 14410 | 15780 | 3990 | 1930 | 110 | 148 | 132 | 108 | 29 | 0.1250 |
| 660 | 14530 | 15980 | 4130 | 1950 | 110 | 149 | 132 | 115 | 29 | 0.1375 |
| 673 | 15420 | 17480 | 4280 | 1950 | 117 | 150 | 144 | 115 | 30 | 0.1500 |
| 731 | 16320 | 18390 | 4420 | 2020 | 117 | 156 | 144 | 115 | 30 | 0.1625 |
| 772 | 16320 | 18470 | 4580 | 2100 | 129 | 156 | 148 | 124 | 30 | 0.1750 |
| 773 | 17120 | 18970 | 4840 | 2260 | 139 | 158 | 149 | 125 | 31 | 0.1875 |
| 773 | 17120 | 20110 | 4880 | 2340 | 141 | 160 | 152 | 136 | 32 | 0.2000 |

TABLE 19-continued

Grain size data for various materials

| Control materials (sizes in nm) | | | | | Nanograin materials (sizes in nm) | | | | | CDF |
|---|---|---|---|---|---|---|---|---|---|---|
| 35N LT | 304 | 316 | 1058 | Nitinol | 35N LT nano-grain | 304 nano-grain | 316 nano-grain | 1058 nano-grain | Nitinol nano-grain | |
| 794 | 18020 | 20980 | 5020 | 2350 | 142 | 160 | 152 | 140 | 32 | 0.2125 |
| 853 | 18110 | 21300 | 5020 | 2350 | 142 | 160 | 157 | 141 | 32 | 0.2250 |
| 870 | 18920 | 21390 | 5280 | 2430 | 145 | 160 | 169 | 148 | 33 | 0.2375 |
| 878 | 19000 | 22410 | 5410 | 2430 | 148 | 165 | 169 | 157 | 33 | 0.2500 |
| 930 | 19110 | 22440 | 5560 | 2590 | 148 | 173 | 170 | 157 | 34 | 0.2625 |
| 949 | 19820 | 23170 | 5560 | 2690 | 160 | 181 | 173 | 159 | 34 | 0.2750 |
| 949 | 21700 | 23560 | 5700 | 2710 | 160 | 182 | 177 | 165 | 35 | 0.2875 |
| 972 | 21700 | 23630 | 5760 | 2850 | 163 | 185 | 181 | 165 | 35 | 0.3000 |
| 990 | 22590 | 23630 | 5840 | 2850 | 166 | 186 | 182 | 166 | 36 | 0.3125 |
| 1009 | 22590 | 24140 | 5850 | 2850 | 167 | 186 | 185 | 166 | 36 | 0.3250 |
| 1048 | 22590 | 24550 | 5990 | 2850 | 167 | 190 | 191 | 178 | 36 | 0.3375 |
| 1049 | 22590 | 24710 | 5990 | 2930 | 169 | 194 | 211 | 181 | 36 | 0.3500 |
| 1070 | 22680 | 24740 | 6130 | 2930 | 179 | 194 | 214 | 184 | 38 | 0.3625 |
| 1087 | 23420 | 24740 | 6270 | 2930 | 179 | 202 | 214 | 198 | 39 | 0.3750 |
| 1087 | 23490 | 24950 | 6270 | 3100 | 185 | 206 | 214 | 204 | 40 | 0.3875 |
| 1148 | 23580 | 25290 | 6270 | 3180 | 186 | 206 | 247 | 208 | 40 | 0.4000 |
| 1152 | 23700 | 25520 | 6410 | 3210 | 186 | 206 | 249 | 215 | 40 | 0.4125 |
| 1188 | 24320 | 25860 | 6420 | 3260 | 187 | 210 | 251 | 223 | 41 | 0.4250 |
| 1194 | 24390 | 25960 | 6550 | 3260 | 192 | 214 | 252 | 231 | 41 | 0.4375 |
| 1246 | 24390 | 26020 | 6550 | 3340 | 192 | 218 | 259 | 231 | 43 | 0.4500 |
| 1267 | 24390 | 27040 | 6990 | 3350 | 192 | 222 | 260 | 231 | 43 | 0.4625 |
| 1270 | 25230 | 27070 | 7000 | 3350 | 192 | 223 | 272 | 231 | 44 | 0.4750 |
| 1286 | 26130 | 27590 | 7030 | 3350 | 192 | 231 | 277 | 231 | 44 | 0.4875 |
| 1364 | 26130 | 28740 | 7140 | 3430 | 195 | 231 | 280 | 239 | 44 | 0.5000 |
| 1385 | 26190 | 28760 | 7560 | 3520 | 195 | 232 | 292 | 240 | 45 | 0.5125 |
| 1386 | 26270 | 28880 | 7690 | 3610 | 195 | 235 | 297 | 241 | 45 | 0.5250 |
| 1392 | 27030 | 29310 | 8000 | 3630 | 198 | 236 | 301 | 247 | 47 | 0.5375 |
| 1486 | 27090 | 29910 | 8000 | 3680 | 198 | 239 | 321 | 247 | 48 | 0.5500 |
| 1522 | 27090 | 30510 | 8120 | 3760 | 200 | 243 | 322 | 247 | 49 | 0.5625 |
| 1563 | 27090 | 30550 | 8550 | 3760 | 200 | 247 | 329 | 248 | 51 | 0.5750 |
| 1567 | 27990 | 31060 | 8550 | 3850 | 202 | 247 | 330 | 255 | 51 | 0.5875 |
| 1585 | 27990 | 31060 | 8550 | 3930 | 204 | 251 | 334 | 264 | 51 | 0.6000 |
| 1589 | 27990 | 31060 | 8560 | 3950 | 204 | 252 | 339 | 264 | 53 | 0.6125 |
| 1590 | 28830 | 31080 | 8560 | 4020 | 204 | 252 | 342 | 272 | 53 | 0.6250 |
| 1590 | 28890 | 32310 | 8570 | 4020 | 210 | 252 | 342 | 272 | 53 | 0.6375 |
| 1597 | 28890 | 32760 | 8830 | 4090 | 210 | 255 | 346 | 274 | 55 | 0.6500 |
| 1598 | 28960 | 33410 | 8840 | 4100 | 217 | 255 | 350 | 289 | 55 | 0.6625 |
| 1598 | 29780 | 34160 | 8980 | 4260 | 223 | 255 | 350 | 297 | 56 | 0.6750 |
| 1598 | 29780 | 34480 | 9130 | 4290 | 223 | 264 | 354 | 298 | 59 | 0.6875 |
| 1600 | 29780 | 34530 | 9400 | 4340 | 230 | 267 | 363 | 299 | 59 | 0.7000 |
| 1603 | 30630 | 36210 | 9400 | 4430 | 236 | 268 | 366 | 300 | 60 | 0.7125 |
| 1663 | 31530 | 36250 | 9570 | 4430 | 236 | 272 | 366 | 305 | 60 | 0.7250 |
| 1682 | 31580 | 37950 | 9690 | 4430 | 236 | 276 | 367 | 305 | 60 | 0.7375 |
| 1701 | 31850 | 37950 | 9700 | 4430 | 236 | 280 | 383 | 305 | 62 | 0.7500 |
| 1764 | 32480 | 38210 | 9880 | 4520 | 243 | 285 | 384 | 313 | 63 | 0.7625 |
| 1780 | 33330 | 38520 | 9880 | 4520 | 254 | 285 | 430 | 314 | 65 | 0.7750 |
| 1784 | 33380 | 39660 | 9970 | 4600 | 254 | 289 | 440 | 321 | 65 | 0.7875 |
| 1859 | 33440 | 39760 | 10000 | 4600 | 255 | 292 | 440 | 331 | 67 | 0.8000 |
| 1877 | 35420 | 40840 | 10120 | 4680 | 261 | 292 | 444 | 331 | 68 | 0.8125 |
| 1957 | 35550 | 41420 | 10400 | 4790 | 261 | 296 | 445 | 332 | 68 | 0.8250 |
| 2056 | 36040 | 42590 | 10460 | 4860 | 267 | 297 | 449 | 338 | 70 | 0.8375 |
| 2234 | 36080 | 42630 | 10690 | 5100 | 267 | 305 | 474 | 338 | 70 | 0.8500 |
| 2253 | 36080 | 42670 | 10700 | 5260 | 273 | 317 | 500 | 363 | 71 | 0.8625 |
| 2353 | 38220 | 43200 | 10760 | 5290 | 274 | 317 | 515 | 379 | 71 | 0.8750 |
| 2472 | 39640 | 46550 | 11260 | 5360 | 275 | 321 | 535 | 380 | 75 | 0.8875 |
| 2513 | 39680 | 47160 | 11550 | 5430 | 280 | 338 | 568 | 396 | 80 | 0.9000 |
| 2688 | 40010 | 47180 | 12110 | 5520 | 286 | 342 | 584 | 404 | 81 | 0.9125 |
| 2729 | 40540 | 47710 | 12390 | 5530 | 293 | 367 | 597 | 420 | 82 | 0.9250 |
| 2768 | 41790 | 50590 | 12390 | 5680 | 298 | 371 | 601 | 421 | 85 | 0.9375 |
| 2984 | 42500 | 51800 | 12450 | 5770 | 317 | 383 | 634 | 438 | 91 | 0.9500 |
| 3262 | 46510 | 55200 | 13260 | 5790 | 324 | 391 | 669 | 479 | 92 | 0.9625 |
| 3499 | 47780 | 55250 | 13680 | 6430 | 381 | 404 | 687 | 537 | 92 | 0.9750 |
| 4289 | 54080 | 57520 | 14330 | 6600 | 418 | 416 | 708 | 637 | 95 | 0.9875 |
| 5223 | 65090 | 58120 | 16390 | 7270 | 576 | 441 | 922 | 638 | 128 | 1.0000 |
| <u>1480</u> | <u>26363</u> | <u>29655</u> | <u>7533</u> | <u>3573</u> | <u>201</u> | <u>234</u> | <u>311</u> | <u>247</u> | <u>50</u> | — |

IV. Applications

Wires made in accordance with the present process are susceptible of a variety of applications including, but not limited to the applications detailed below. Exemplary applications of wires in accordance with the present process are set forth below, and shown generally in FIGS. 27-30(b).

A. Guide Wires

Figure 27:
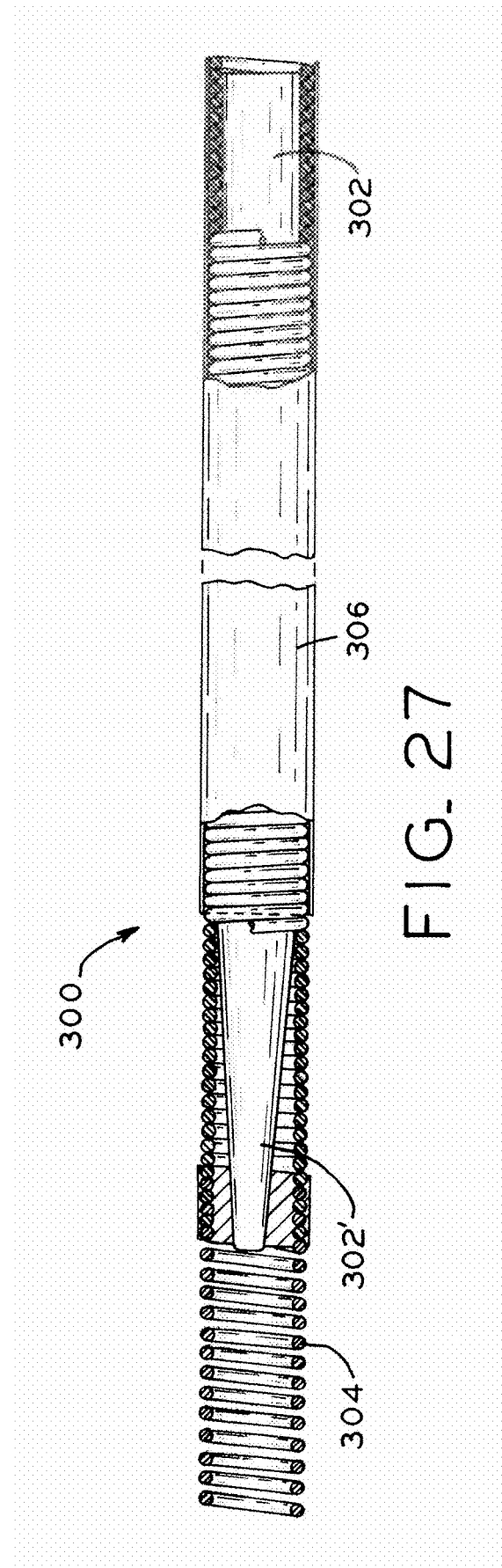
FIG. 27 is a partial section view of a guide wire in accordance with an embodiment of the present process.

Referring to FIG. 27, a percutaneous transluminal coronary angioplasty (PTCA) guide wire 300 is shown which comprises a metallic elongate wire 302 manufactured in accordance with the present process with tapered end 302'. Wire 302 is received within a coil wire 304, which in turn is received within a housing 306.

PTCA guide wires are used to access distal locations within the human body to treat vessel lesion in including, for example, atherosclerosis, or in order to facilitate implantation of a defibrillation electrode. In order to reach these locations, guide wires must flex sufficiently to navigate the anatomy en route to the target lesion or organ.

Figure 28:
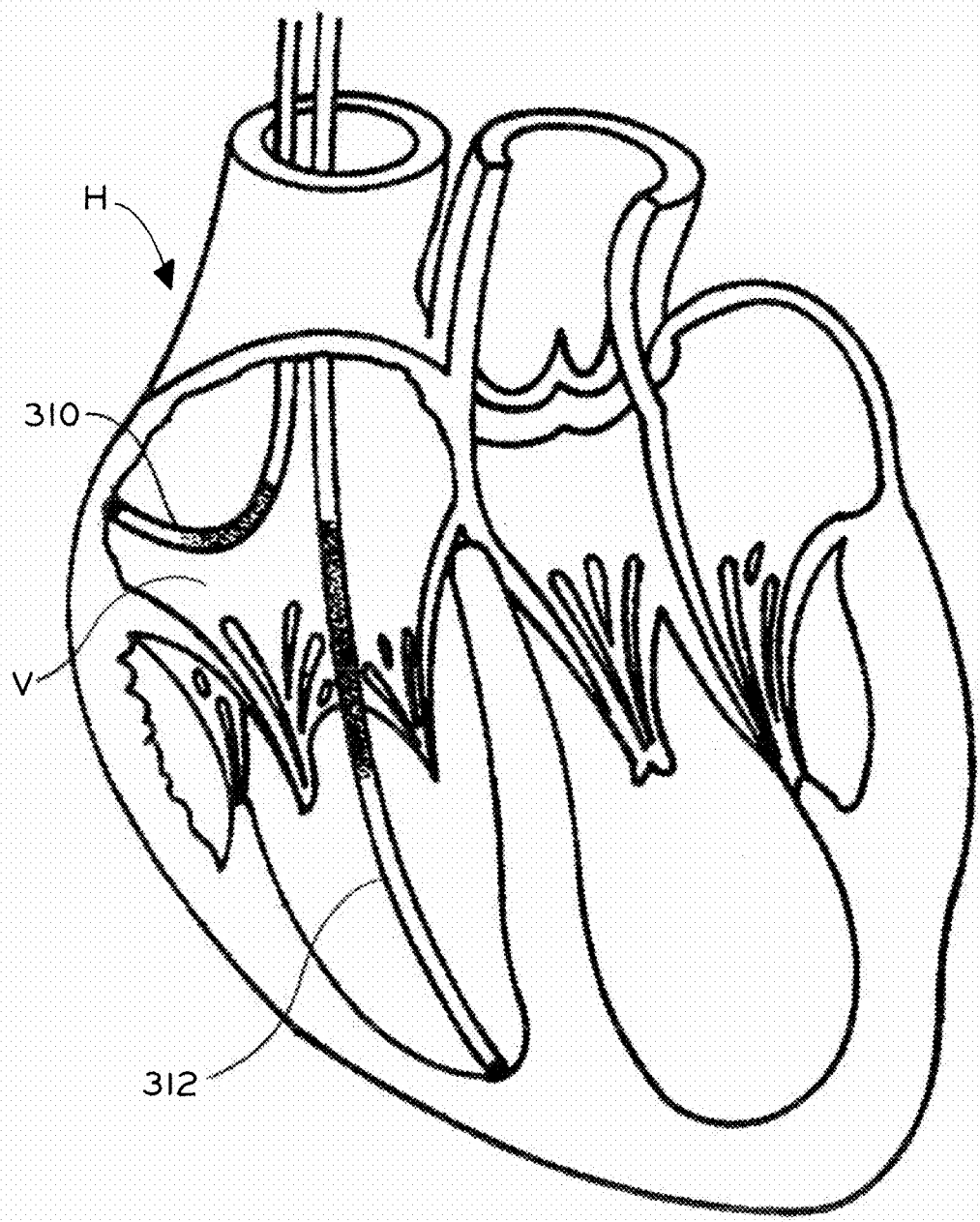
FIG. 28 is a partial section view of a heart, illustrating cardiac pacing leads received therein.

The elastic properties of the guide wire may be important in guide wire design because the wire should conform to the tortuous vessel anatomy as it is used to access various targeted locations for treatment within the body, such as the right ventricle of the heart as shown in FIG. 28.

The guide wire should successfully navigate the anatomy without suffering a material failure.

The present process provides a wire that possesses a high degree of flexibility due to a relatively high yield to ultimate strength ratio which is greater than 0.85, thereby imparting a relatively high yield strain to the guide wire.

In some cases, a physician will manually shape the tip section of a guide wire in order to facilitate navigation of specific vessel anatomy. In this case, a material must possess the ability to both accept plastic deformation, in order to take a specific shape, and maintain good resilience to successfully move through the anatomy.

Wire 302 prepared in accordance with the present process provides a combination of relatively high yield strength and ductility, thereby increasing the ability of wire 302 to withstand both pre-procedural, physician-planned plastic deformation and subsequent procedural elastic deformation en route to the target lesion.

B. Implantable Cardiac Pacing Wires

Figure 29:
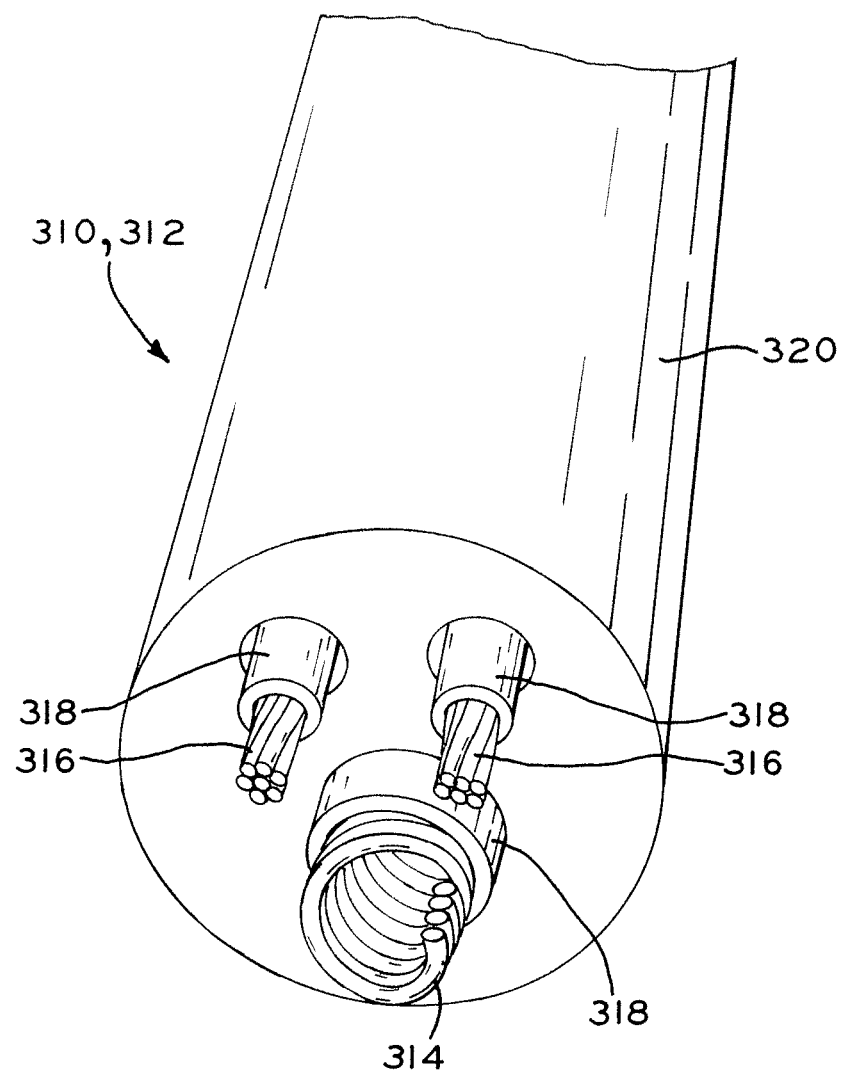
FIG. 29 is a section, perspective view of a cardiac pacing lead including wire made in accordance with the present process.

Referring to FIGS. 28 and 29, a first cardiac pacing lead wire 310 and second cardiac pacing lead wire 312 made in accordance with the present process are shown. Wires 310, 312 are utilized either singularly or in plurality in the form of a conductive braid, strand or microcable which is used to deliver therapeutic electrical signals to the heart.

Referring to FIG. 29, the cardiac pacing lead wires 310, 312 may comprise a combination of coiled wires 314 and/or microcable elements 316 which are overmoulded and/or separated by an electrically insulating polymer sleeve 318 such as medical-grade polyurethane or silicone rubber. Sleeves 318 and wires 314, 316 are received within a housing 320.

Referring to FIG. 28, the lead is implanted within the right atrium and/or ventricle V of the heart H in order to deliver an electrical control signal thereby stimulating or otherwise providing pacing, defibrillation or cardiac resynchronization therapy in order to treat bradycardia, tachycardia, or other arrhythmias of the heart.

Within the spirit of this disclosure, dependent upon the intended therapy and patient physiology, lead wires 310, 312, or similar systems utilizing wires made in accordance with the invention may also be implanted with electrical connection to the outside of the heart the left atrium and the left ventricle. Clinical outcomes and required material characteristics are generally similar to those described earlier.

It is advantageous that pacing lead wires 310, 312 be substantially resistant to cyclic mechanical fatigue damage which is generally associated with the spatial displacement of the lead system with each beat of the heart at an average rate of up to 2 Hz.

Such displacements of the heart and therefore the lead system create geometry-controlled cyclic strains in the metallic wires that make up the conductive portion of the lead wire itself, accumulating up to 60 million cycles per year due to the heart rhythm alone.

In addition to chronic cyclic mechanical loading, cardiac lead wires 310, 312 may undergo some plastic deformation due to loads imparted to the system during implantation. Thus, lead wires 310, 312 will benefit from being capable of withstanding implant-load-related deformation and post-implant geometry-controlled cyclic deformation. Enhancement of lead wires 310, 312 may be realized by selection of metallic wire materials possessing high levels of fatigue endurance and ductility.

Advantageously, wires 310, 312 provide a high level of fatigue endurance strain in geometry-controlled loading and ductility and may therefore provide enhanced long term device performance when placed into any of a variety of cardiac lead designs.

Wire made in accordance with the present process may also be used for leads for gastric, neurological, or other biological electrical stimulation.

C. Wire-based stents

Referring to FIGS. 30(a), a tissue scaffold or vessel stent device 370 is shown which is made from one or more wires 372 made in accordance with the present process, which are braided, knitted, or otherwise formed together to produce the generally cylindrical cross-sectional shape of device 370.

Referring to and FIG. 30(b), a tissue scaffold or vessel stent device 370' is shown which is made from one or more wires 372' made in accordance with the present process, which are knitted together to form the generally cylindrical cross-sectional shape of device 370'.

Upon release from the delivery catheter, stents move to some degree, dependent on the relative vessel and device compliance, with the artery due to fluctuations in blood pressure, arterial vessel smooth muscle contraction and dilation, and due to general anatomical movement. Such mechanical displacement results in cyclic straining of wires 372, 372' comprising the structure of stent 370, 370' structure.

Non bioerodable tissue scaffolds or stents are generally implanted permanently, and therefore should be able to withstand millions of mechanical load cycles without losing structural integrity due to mechanical fatigue.

Stents 370, 370', which are constructed from wires 372, 372' made in accordance with the present process, possess a high degree of resistance to fatigue damage and thus offer optimized performance as compared to conventional stents made with wires having lower fatigue strength.

While this invention has been described as having a preferred design, the present process can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A metallic wire comprising an implant grade, non-shape memory metal or metal alloy having a diameter less than 1.0 mm, and a mean grain size of less than 500 nanometers throughout said non-shape memory metal or metal alloy of said metallic wire, as measured along all arbitrarily defined axes of the respective grains.

2. The wire of claim 1, said wire having a fatigue endurance such that the wire survives one million cycles at a strain amplitude between 0.35% and 0.65%.

3. The wire of claim 1, comprising a Co/Ni/Cr/Mo metal alloy having a fatigue endurance such that the wire survives $10^6$ cycles at a strain amplitude between 0.45% and 0.65%.

4. The wire of claim 1, comprising a 304L stainless steel having a fatigue endurance such that the wire survives $10^6$ cycles at a strain amplitude between 0.4% and 0.45%.

5. The wire of claim 1, comprising a 316L stainless steel having a fatigue endurance such that the wire survives $10^6$ cycles at a strain amplitude between 0.35% and 0.4%.

6. The wire of claim 1, comprising a Co/Cr/Fe/Ni/Mo metal alloy having a fatigue endurance such that the wire survives $10^6$ cycles at a strain amplitude between 0.4% and 0.5%.

7. The wire of claim 1, having an axial ductility of between 6% and 17.9% strain to rupture, as measured by a monotonic tensile test with a gauge length exceeding 250× said diameter of the wire at a temperature of 298 ±5K.

8. The wire of claim 7, comprising a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of between 0.85 and 0.97.

9. The wire of claim 1, having an axial ductility of between 10% and 17.9% strain to rupture, as measured by a monotonic tensile test with a gauge length exceeding 250× said diameter of the wire at a temperature of 298 ±5K.

10. The wire of claim 9, comprising a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of between 0.85 and 0.97.

11. A method of forming a wire made of an implant grade, non-shape memory metal or metal alloy, comprising the steps of:
providing a wire made of the implant grade, non-shape memory metal or metal alloy, the wire having a diameter $D_1$;
subjecting the wire to cold work conditioning to impart one of: i) between 50% and 99.9% cold work and ii) between 0.69 and 6.91 units of true strain by drawing the wire to a diameter $D_2$ less than diameter $D_1$, wherein % cold work is determined by the following formula:

$$cw = \left[1 - \left(\frac{D_2}{D_1}\right)^2\right] \times 100\%$$

and true strain is determined by the following formula:

$$ts = \ln\left(\left(\frac{D_1}{D_2}\right)^2\right); \text{ and}$$

annealing the wire to create a crystal structure having a finished mean grain size of less than 500 nanometers as measured alone all arbitraril defined axes of the respective grains.

12. The method of claim 11, wherein the wire comprises a metal alloy selected from the group consisting of i) a Co/Ni/Cr/Mo metal alloy; ii) a 304L stainless steel;
iii) a 316L stainless steel; and iv) a Co/Cr/Fe/Ni/Mo metal alloy.

13. The method of claim 11, wherein said annealing step further comprises annealing the wire at a temperature of between 600° C. and 950° C. for a dwell time of between 0.1 and 3600 seconds.

14. The method of claim 11, wherein said annealing step further comprises annealing the wire at a temperature of between 750° C. and 900° C. for a dwell time of between 0.2 and 120 seconds.

15. The method of claim 11, further comprising the additional step, following said annealing step, of subjecting the wire to additional cold work.

16. The method of claim 11, wherein said step of subjecting the wire to cold work conditioning comprises one of: i) performing a single draw of the wire through a die and ii) performing multiple draws of the wire through a die in which the multiple draws are performed sequentially without any annealing step therebetween.

17. The method of claim 16, wherein the wire comprises a metal alloy selected from the group consisting of: i) a Co/Ni/Cr/Mo metal alloy; ii) a 304L stainless steel; iii) a 316L stainless steel; and iv) a Co/Cr/Fe/Ni/Mo metal alloy.

18. The method of claim 16, wherein said annealing step further comprises annealing the wire at a temperature of between 600° C. and 950° C. for a dwell time of between 0.1 and 3600 seconds.

19. The method of claim 16, wherein said annealing step further comprises annealing the wire at a temperature of between 750° C. and 900° C. for a dwell time of between 0.2 and 120 seconds.

20. The method of claim 16, further comprising the additional step, following said annealing step, of subjecting the wire to additional cold work.

21. The method of claim 16, wherein said step of subjecting the wire to cold work conditioning comprises drawing the wire to the diameter $D_2$ of less than 1mm.

22. The method of claim 16, wherein said step of subjecting the wire to cold work conditioning comprises imparting at least one of: i) between 94% and 99.9% cold work and ii) between 2.81 and 6.91 units of true strain.

23. The method of claim 22, wherein said annealing step further comprises annealing the wire at a temperature of between 680° C. and 900° C. for a dwell time of between a fraction of a second and 15 seconds.

24. The wire of claim 16, wherein said annealing step further comprises annealing the wire to create a crystal structure having mean grain size between 100 nanometers and 300 nanometers.

25. The method of claim 12, wherein said annealing step further comprises annealing the wire at a temperature of between 680° C. and 900° C. for a dwell time of between a fraction of a second and 15 seconds.

26. The method of claim 25, wherein said step of subjecting the wire to cold work conditioning comprises imparting at least one of: i) between 94% and 99.9% cold work and ii) between 2.81 and 6.91 units of true strain.

27. The wire of claim 1, wherein said mean grain size is between 100 nanometers and 300 nanometers.

28. The wire of claim 1, comprising a Co/Ni/Cr/Mo metal alloy having a fatigue endurance such that the wire survives $10^7$ cycles at a strain amplitude between 0.45% and 0.65%.

29. The wire of claim 1, comprising a Co/Ni/Cr/Mo metal alloy having a fatigue endurance such that the wire survives $10^8$ cycles at a strain amplitude between 0.45% and 0.65%.

30. The wire of claim 1, comprising a 304L stainless steel having a fatigue endurance such that the wire survives $10^7$ cycles at a strain amplitude between 0.4% and 0.45%.

31. The wire of claim 1, comprising a 304L stainless steel having a fatigue endurance such that the wire survives $10^8$ cycles at a strain amplitude between 0.4% and 0.45%.

32. The wire of claim 1, comprising a 316L stainless steel having a fatigue endurance such that the wire survives $10^7$ cycles at a strain amplitude between 0.35% and 0.40%.

33. The wire of claim 1, comprising a 316L stainless steel having a fatigue endurance such that the wire survives $10^8$ cycles at 0.35% strain amplitude.

34. The wire of claim 1, comprising a Co/Cr/Fe/Ni/Mo metal alloy having a fatigue endurance such that the wire survives $10^7$ cycles at a strain amplitude between 0.4% and 0.45%.

35. The wire of claim 1, comprising a Co/Cr/Fe/Ni/Mo metal alloy having a fatigue endurance such that the wire survives $10^8$ cycles at a strain amplitude between 0.4% and 0.45%.

36. A metallic wire comprising an implant grade, non-shape memory metal or metal alloy having a thickness less than 1.0 mm, and a mean grain size of less than 500 nanometers throughout said non-shape memory metal or metal alloy of said metallic wire, as measured along all arbitrarily defined axes of the respective grains.

37. The wire of claim 36, wherein said mean grain size is between 100 nanometers and 300 nanometers.

38. The wire of claim 36, said wire having a fatigue endurance such that the wire survives one million cycles at a strain amplitude between 0.35% and 0.65%.

39. The wire of claim 36, having an axial ductility of between 6% and 17.9% strain to rupture, as measured by a monotonic tensile test with a gauge length exceeding 250× said thickness of the wire at a temperature of 298 ±5K.

40. The wire of claim 39, comprising a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of between 0.85 and 0.97.

41. The wire of claim 36, having an axial ductility of between 10% and 17.9% strain to rupture, as measured by a monotonic tensile test with a gauge length exceeding 250× said thickness of the wire at a temperature of 298 ±5K.

42. The wire of claim 41, comprising a non-shape memory metal alloy selected from the group consisting of a Co/Ni/Cr/Mo metal alloy, a 316L stainless steel, and a Co/Cr/Fe/Ni/Mo metal alloy having a yield to ultimate strength ratio of between 0.85 and 0.97.

43. The method of claim 11, wherein said step of annealing the wire creates a crystal structure having a mean grain size of less than 500 nanometers throughout the non-shape memory metal or metal alloy of the wire.

44. The method of claim 11, wherein said annealing step further comprises annealing the wire at a temperature of between 600° C. and 850° C.

45. The method of claim 11, wherein said annealing step further comprises annealing the wire at a temperature of between 750° C. and 810° C.

46. The method of claim 11, wherein said annealing step further comprises annealing the wire at a temperature of about 750° C. for about 3600 seconds.

47. The method of claim 15, wherein said step of subjecting the wire to additional cold work comprises imparting between 15% and 70% additional cold work to the wire.

48. The method of claim 15, wherein said step of subjecting the wire to additional cold work comprises imparting between 60% and 70% additional cold work to the wire.

49. The wire of claim 1, said wire comprising a Co/Ni/Cr/Mo metal alloy having a yield strength of at least 1393 MPa and as much as 1646 MPa.

50. The wire of claim 1, said wire comprising a Co/Ni/Cr/Mo metal alloy having an elastic modulus of at least 21.8 Mpsi and as much as 24.5 Mpsi.

51. The wire of claim 1, wherein said diameter of said wire is less than 0.5 mm.

52. The wire of claim 51, wherein said diameter of said wire is at least 0.127 mm.

53. The wire of claim 1, wherein said wire comprises a guide wire.

54. The wire of claim 53, wherein said guide wire is received within a coil wire, and said coil wire is received within a housing.

55. The wire of claim 54, wherein said guide wire comprises a tapered end.

56. The wire of claim 1, wherein:
said wire comprises a Co/Ni/Cr/Mo metal alloy having an elastic modulus of at least 21.8Mpsi and as much as 24.5 Mpsi;
said diameter of said wire is less than 0.5 mm; and
said wire comprises a guide wire.

57. The wire of claim 56, wherein said guide wire comprises a tapered end.

58. The wire of claim 36, said wire comprising a Co/Ni/Cr/Mo metal alloy having a yield strength of at least 1393 MPa and as much as 1646 MPa.

59. The wire of claim 36, said wire comprising a Co/Ni/Cr/Mo metal alloy having an elastic modulus of at least 21.8 Mpsi and as much as 24.5 Mpsi.

60. The wire of claim 36, wherein said diameter of said wire is less than 0.5 mm.

61. The wire of claim 60, wherein said diameter of said wire is at least 0.127 mm.

62. The wire of claim 36, wherein said wire comprises a guide wire.

63. The wire of claim 62, wherein said guide wire is received within a coil wire, and said coil wire is received within a housing.

64. The wire of claim 63, wherein said guide wire comprises a tapered end.

65. The wire of claim 36, wherein:
said wire comprises a Co/Ni/Cr/Mo metal alloy having an elastic modulus of at least 21.8Mpsi and as much as 24.5 Mpsi;
said diameter of said wire is less than 0.5 mm; and
said wire comprises a guide wire.

66. The wire of claim 65, wherein said guide wire comprises a tapered end.

67. The method of claim 11 wherein:
said step of providing a wire comprises providing a wire made of Co/Ni/Cr/Mo metal alloy;
said step of subjecting the wire to cold work conditioning comprises imparting between 92% and 99.9% cold work; and said step of annealing comprises annealing the wire at a temperature of between 810° C. and 900° C. for a dwell time of between 0.8 and 120 seconds.

68. The method of claim 11 wherein:

said step of providing a wire comprises providing a wire made of 304L stainless steel metal alloy;

said step of subjecting the wire to cold work conditioning comprises imparting between 94% and 99.99% cold work; and said step of annealing comprises annealing the wire at a temperature of between 640° C. and 850° C. for a dwell time of between 0.8 and 120 seconds.

69. The method of claim 11 wherein:

said step of providing a wire comprises providing a wire made of 316L stainless steel metal alloy;

said step of subjecting the wire to cold work conditioning comprises imparting between 90% and 99.999% cold work; and said step of annealing comprises annealing the wire at a temperature of between 680° C. and 875° C. for a dwell time of between 0.8 and 120 seconds.

70. The method of claim 11 wherein:

said step of providing a wire comprises providing a wire made of Co/Cr/Fe/Ni/Mo stainless steel metal alloy;

said step of subjecting the wire to cold work conditioning comprises imparting between 92% and 99.9% cold work; and said step of annealing comprises annealing the wire at a temperature of between 810° C. and 890° C. for a dwell time of between 0.5 and 120 seconds.

* * * * *